US012222346B2

(12) United States Patent
Drndic et al.

(10) Patent No.: US 12,222,346 B2
(45) Date of Patent: Feb. 11, 2025

(54) STABLE NANOPORES AND NANOPORE ARRAYS FOR IONIC AND OTHER MEASUREMENTS

(71) Applicant: The Trustees of the University of Pennsylvania, Philadelphia, PA (US)

(72) Inventors: Marija Drndic, Philadelphia, PA (US); Yung-Chien Chou, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 839 days.

(21) Appl. No.: 17/218,365

(22) Filed: Mar. 31, 2021

(65) Prior Publication Data

US 2021/0318288 A1    Oct. 14, 2021

Related U.S. Application Data

(60) Provisional application No. 63/003,434, filed on Apr. 1, 2020.

(51) Int. Cl.
*G01N 33/487* (2006.01)
*B81C 1/00* (2006.01)
*G01N 27/447* (2006.01)

(52) U.S. Cl.
CPC ... *G01N 33/48721* (2013.01); *B81C 1/00087* (2013.01); *G01N 27/44791* (2013.01)

(58) Field of Classification Search
None
See application file for complete search history.

(56) References Cited

U.S. PATENT DOCUMENTS

| | | |
|---|---|---|
| 6,746,594 B2 | 6/2004 | Akeson et al. |
| 7,811,479 B2 | 10/2010 | Drndic et al. |
| 7,813,160 B2 | 10/2010 | Drndic et al. |
| 7,887,720 B2 | 2/2011 | Drndic et al. |
| 8,173,335 B2 | 5/2012 | Drndic et al. |
| 10,876,157 B2 * | 12/2020 | Drndic ............ G01N 33/48721 |
| 2002/0117659 A1 | 8/2002 | Lieber et al. |
| 2004/0099901 A1 | 5/2004 | Ludwig |
| 2005/0196876 A1 | 9/2005 | Chan et al. |
| 2006/0105523 A1 | 5/2006 | Afzali-Ardakani et al. |
| 2007/0161004 A1 | 7/2007 | Brown et al. |
| 2007/0172386 A1 | 7/2007 | Li et al. |

(Continued)

FOREIGN PATENT DOCUMENTS

WO     00/28312 A1   5/2000
WO   2002/099878 A1  12/2002

(Continued)

OTHER PUBLICATIONS

Lv et al., "The Fluctuations of Blocked Ionic Current Reveal the Instantaneous Statuses of DNA in Graphene Nanopore," eprint arXiv: 1302.3671, publication date Feb. 2013, 19 pages.

(Continued)

*Primary Examiner* — J. Christopher Ball
(74) *Attorney, Agent, or Firm* — BakerHostetler

(57) ABSTRACT

Provided are nanopore devices that include a hafnium oxide coating on the pores of the devices. Such devices exhibit improved stability, especially when in a salt solution environment. Also provided are related methods.

23 Claims, 45 Drawing Sheets
(45 of 45 Drawing Sheet(s) Filed in Color)

(56) References Cited

U.S. PATENT DOCUMENTS

| | | |
|---|---|---|
| 2008/0053902 A1 | 3/2008 | Koegler et al. |
| 2008/0171316 A1 | 7/2008 | Golovchenko et al. |
| 2009/0136948 A1 | 5/2009 | Han et al. |
| 2009/0142825 A1 | 6/2009 | Murray et al. |
| 2009/0236609 A1 | 9/2009 | De et al. |
| 2010/0009134 A1 | 1/2010 | Drndic et al. |
| 2010/0035260 A1 | 2/2010 | Olasagasti et al. |
| 2010/0327847 A1 | 12/2010 | Leiber et al. |
| 2011/0227044 A1 | 9/2011 | Kawanaka et al. |
| 2011/0227558 A1 | 9/2011 | Mannion et al. |
| 2012/0037919 A1 | 2/2012 | Xu et al. |
| 2012/0142016 A1 | 6/2012 | Ronaghi et al. |
| 2012/0234679 A1 | 9/2012 | Garaj et al. |
| 2013/0092541 A1 | 4/2013 | Drndic et al. |
| 2013/0180867 A1 | 7/2013 | Rosenstein et al. |
| 2013/0256154 A1 | 10/2013 | Peng |
| 2013/0309776 A1 | 11/2013 | Drndic et al. |
| 2014/0174927 A1 | 6/2014 | Bashir et al. |
| 2015/0232923 A1* | 8/2015 | Drndic ............... C12Q 1/6869 427/535 |
| 2021/0215664 A1* | 7/2021 | Saly .................... C12Q 1/6869 |

FOREIGN PATENT DOCUMENTS

| | | |
|---|---|---|
| WO | 2006/076036 A2 | 7/2006 |
| WO | 2006/102292 A2 | 9/2006 |
| WO | 2008/092760 A1 | 8/2008 |
| WO | 2009/020682 A2 | 2/2009 |
| WO | 2009/035647 A1 | 3/2009 |
| WO | 2009/045473 A2 | 4/2009 |
| WO | 2010/066851 A1 | 6/2010 |
| WO | 2011/046706 A1 | 4/2011 |
| WO | 2011/047582 A1 | 4/2011 |
| WO | 2011/103424 A2 | 8/2011 |
| WO | 2012/005857 A1 | 1/2012 |
| WO | 2012/116161 A1 | 8/2012 |

OTHER PUBLICATIONS

Manrao et al, "Reading DNA At Single-Nucleotide Resolution With A Mutant MspA nanopore and phi29 DNA Polymerase", Nature Biotechnology, Mar. 2012, 30(4), 349-353.

Meller, A et al., "Single molecule measurements of DNA transport through a nanopore", Electrophoresis 2002, 23, 2583-2591.

Merchant CA, et al. "DNA translocation through grapheme nanopores", Nano Lett. Aug. 11, 2010;10(8):2915-21.

Merchant, MA et al. DNA Translocation Through Graphene Nanopores. Jul. 23, 2010, Nano letters. 2010, vol. 10, No. 8; pp. 3163-3167.

Meunier, V., Krsti 'P. S., "Enhancement of the Transverse Conductance in DNA Nucleotides", The Journal of Chemical Physics, Jan. 2008, 128, 041103.

Meyer JC, et al. "The structure of suspended graphene sheets", Nature. Mar. 1, 2007;446(7131):60-3.

Nelson et al, "Detection of Nucleic Acids with Graphene Nanopores: Ab Initio Characterization of a Novel Sequencing Device", Nano Letters, Sep. 8, 2010, 10(9), 3237-3242.

Novoselov KS, et al. "Electric field effect in atomically thin carbon films", Science. Oct. 22, 2004;306(5696):666-9.

Novoselov KS, et al. "Room-temperature quantum Hall effect in grapheme", Science. Mar. 9, 2007;315(5817):1379. Epub Feb. 15, 2007.

Polansky et al, "Nanopore in metal-dielectric sandwich for DNA position control", Applied Physics Letters, Oct. 2007, 91(15), 153103.

Postma, H. W. Ch., "Rapid Sequencing of Individual DNA Molecules in Graphene Nanogaps", Nano Letters, Jan. 4, 2010, 10(2), 420-425.

R. Wang et al. "Light-induced amphiphilic surfaces", Nature 1997, 388, 431-432.

Rosenstein, JK et al. Integrated nanopore sensing platform with sub-microsecond temporal resolution. Nature Methods. 2012. vol. 9. pp. 487-494.

Saha et al, "DNA Base-Specific Modulation of Microampere Transverse Edge Currents Through a Metallic Graphene Nanoribbon With a Nanopore", Nano Letters, Jan. 11, 2012, 12(1), 50-55.

Schneider GF, et al. "DNA translocation through graphene nanopores", Nano Lett. Aug. 11, 2010;10(8):3163-7.

Sigalov et al., "Detection of DNA Sequences Using an Alternating Electric Field in a Nanopore Capacitor", Nanoletters, 2008, vol. 8, No. 1, 56-63.

Simmons JM, et al. "Effect of ozone oxidation on single-walled carbon nanotubes", J Phys Chem B. Apr. 13, 2006;110(14):7113-8.

Siwy ZS, et al. "Engineered voltage-responsive nanopores", Chem Soc Rev. Mar. 2010;39(3):1115-32. Epub Dec. 4, 2009.

Skinner GM, et al. "Distinguishing single- and double-stranded nucleic acid molecules using solid-state nanopores", Nano Lett. Aug. 2009;9(8):2953-60.

Smeets RM, et al. "Nanobubbles in solid-state nanopores", Phys Rev Lett. Aug. 25, 2006;97(8):088101. Epub Aug. 24, 2006.

Smeets, Rmm et al. Salt Dependence of Ion Transport and DNA Translocation Through Solid-State Nanopores. Nano letters. Dec. 13, 2005, vol. 6, No. 1; pp. 89-95; p. 90.

Storm AJ, et al. "Fabrication of solid-state nanopores with single-nanometre precision", Nat Mater. Aug. 2003;2(8):537-40.

Storm AJ, et al. "Translocation of double-strand DNA through a silicon oxide nanopore", Phys Rev E Stat Nonlin Soft Matter Phys. May 2005;71(5 Pt 1): 051903. Epub May 6, 2005.

Storm et al., "Fabrication of Solid-State Nanopores with single-nanometer precision", Nature Materials, Aug. 2003, vol. pp. 537-540.

Tabard-Cossa et al, "Noise Analysis and Reduction in Solid-State Nanopores", Nanotechnology, Jun. 29, 2007, 18(30), 305505.

Tanaka, H., and Kawai, T., "Partial Sequencing of a Single DNA Molecule With a Scanning Tunnelling Microscope", Nature Nanotechnology, Jul. 5, 2009, 4, 518-522.

Tsutsui et al, "Electrical Detection of Single Methylcytosines in a DNA Oligomer", Journal of the American Chemical Society, Jun. 15, 2011, 133(23), 9124-9128.

Tsutsui et al, "Identifying Single Nucleotides By Tunnelling Current", Nanotechnology, Apr. 2010, 5, 286-290.

Tsutsui et al, "Single-Molecule Sensing Electrode Embedded In-Plane Nanopore", Scientific. Reports, Jul. 28, 2011, 1,46.

Tuchband et al, "Insulated gold scanning tunneling microscopy probes for recognition tunneling in an aqueous environment", Review of Scientific Instruments, Janaury 2012, 83(1), 015102-1-015102-4.

U.S. Patent Application Filed on Aug. 16, 2012 by Drndic et al., U.S. Appl. No. 13/587,141.

Varghese N, et al. "Binding of DNA nucleobases and nucleosides with grapheme", Chemphyschem. Jan. 12, 2009;10(1):206-10.

Venkatesan BM, et al. "Highly Sensitive, Mechanically Stable Nanopore Sensors for DNA Analysis", Adv Mater. Jul. 20, 2009;21(27):2771.

Venkatesan, B. M., and Bashir, R., "Nanopore Sensors for Nucleic Acid Analysis", Nature Nanotechnology, Oct. 2011, 6, 615-624.

Venkatesan, B. M., et al. "DNA Sensing Using Nanocrystalline Surface-Enhanced Al2O3 Nanopore Sensors", Adv. Funct. Mater., Apr. 2010, 20:1266-1275.

Wang S, et al. "Wettability and surface free energy of graphene films", Langmuir. Sep. 15, 2009;25(18):11078-81.

Wanunu, "DNA Translocation Governed by Interactions with Solid-State Nanopores", Biophysical Journal, Nov. 2008, vol. 95, 4716-4725.

Wanunu, M et al. Nanopore analysis of individual rna/antibiotic complexes. ACS Nano. 2011. vol. 5(12). pp. 9345-9353.

Wanunu, M., "Nanopores: A Journey Towards DNA Sequencing", Physics of Life Reviews, Jun. 2012, 9(2), 125-158.

Wanunu, M., and Meller, A., "Chemically Modified Solid-State Nanopores", Nano Letters, Jun. 2007, 7(6), 1580-1585.

Xie et al, "Local Electrical Potential Detection of DNA By Nanowire-Nanopore Sensors", Nature Nanotechnology, Feb. 2012, 7, 119-125.

Zhang Y. et al., "Formation of metal nanowires on suspended single-walled carbon nanotubes", Appl Phys Lett. Nov. 2000, 77, 3015-3017.

(56) References Cited

OTHER PUBLICATIONS

Zwolak M, et al. "Electronic signature of DNA nucleotides via transverse transport", Nano Lett. Mar. 2005;5(3):421-4.

Zwolak, M. and Di Ventra, M., "Electronic Signature of DNA Nucleotides via Transverse Transport", Nano Letters,. Mar. 2005, 5(3), 421-424.

Aarik, J. et al., "Atomic layer deposition of TiO2 thin films from TiI4 and H2O", Appl Surf Sci Jun. 2002, 193, 277.

Astier Y, et al. Toward single molecule DNA sequencing: direct identification of ribonucleoside and deoxyribonucleoside 5'-monophosphates by using an engineered protein nanopore equipped with a molecular adapter. J Am Chem Soc. Feb. 8, 2006;128(5):1705-10.

Balan et al., "Suspended Solid-State Membranes on Glass Chips with Sub 1-pF Capacitance for Biomolecule Sensing Applications", Sci. Rep. 5, 17775, 2015.

Branton et al, "The Potential and Challenges of Nanopore Sequencing", Nature Biotechnology, Oct. 2008, 26, 1146-1153.

Burns MA et al. "Nanopore sequencing technology: research trends and Applications", Trends Biotechnol. Dec. 2006;24(12):580-6. Epub Oct. 19, 2006.

Chang et al, "Electronic Signatures of all Four DNA Nucleosides in a Tunneling Gap", Nano. Letters, Feb. 8, 2010, 10(3), 1070-1075.

Chang et al, "Tunnel Conductance of Watson-Crick Nucleoside-Base Pairs from Telegraph Noise", Nanotechnology May 6, 2009, 20, 185102.

Chang et al, "Tunneling Readout of Hydrogen-Bonding Based Recognition", National Nanotechnology, May 2009, 4(5), 297-301.

Chen et al, "Atomic Layer Deposition to Fine-Tune the Surface Properties and Diameters of Fabricated Nanopores", Nano Letters, Jun. 25, 2004, 4(7), 1333-1337.

Chen et al,, "First-Principles Study of High Conductance DNA Sequencing With Carbon Nanotube Electrodes", Phys. Rev. B., Mar. 2012, 85, 115436.

Chen, P. et al., "Atomic Layer Deposition to Fine-Tune the Surface Properties and Diameters of Fabricated Nanopores", Nano Lett Jun. 2004, 7, 1333-1337.

Chen, P. et al., "Probing Single DNA Molecule Transport Using Fabricated Nanopores", Nano Lett. Oct. 2004, 4, 2293-2298.

Cherf et al, "Automated Forward and Reverse Ratcheting of DNA in a Nanopore at Five Angstrom Precision", Nat. Biotechnol. Feb. 2012, 30, 344-348.

Cho, S. et al., "Gate-tunable graphene spin valve", Appl Phys Lett 2007, 91, 123105.

Clarke J, et al. "Continuous base identification for single-molecule nanopore DNA sequencing", Nat Nanotechnol Apr. 2009, 4(4):265-70. doi: 10.1038/nnano.2009. 12. Epub Feb. 22, 2009.

Danelon et al, "Fabrication and Functionalization of Nanochannels by Electron-Beam-Induced Silicon Oxide Deposition", Sep. 2006, 22, 10711-10715.

Deamer, D. W.and , Akeson, M., "Nanopores and Nucleic Acids: Prospects for Ultrarapid Sequencing", Trends Biotechnology, Apr. 2000, 18, 147-151.

Dekker, C., "Solid-State Nanopores", Nature. Nanotechnology, Apr. 2007, 2, 209-215.

Fischbein MD et al. "Sub-10 nm device fabrication in a transmission electron microscope", Nano Lett. May 2007;7(5):1329-37. Epub Apr. 17, 2007.

Fischbein, M.D. et al., "Electron Beam Nanosculpting of Suspended Graphene Sheets" Appl Phys Lett 2008, 93, 113107.

Garaj S, et al. "Graphene as a subnanometre trans-electrode membrane", Nature. Sep. 9, 2010;467(7312):190-3. Epub Aug. 18, 2010.

Gracheva ME, et al. "Multilayered semiconductor membranes for nanopore ionic conductance modulation", ACS Nano. Nov. 25, 2008;2(11):2349-55.

Gracheva ME, et al. "p-nSemiconductor membrane for electrically tunable ion current rectification and filtering", Nano Lett. Jun. 2007;7(6):1717-22. Epub May 22, 2007.

Grant et al, "Transmission Electron Microscopy 'windows' for Nanofabricated Structures", Nanotechnology, Jul. 16, 2004, 15(9), 1175-1181.

Gu LQ, et al. "Single molecule sensing by nanopores and nanopore devices", Analyst. Mar. 2010; 135(3):441-51. Epub Dec. 22, 2009.

Han MY, et al. "Energy band-gap engineering of grapheme nanoribbons", Phys Rev Lett. May 18, 2007;98(20):206805. Epub May 16, 2007.

Harrer et al, "Electrochemical Protection of Thin Film Electrodes in Solid State Nanopores", Nanotechnology, Jul. 8, 2011, 22(27), 275304.

Hashimoto A, et al. "Direct evidence for atomic defects in graphene layers", Nature. Aug. 19, 2004;430(7002):870-3.

He et al, "Identification of DNA Basepairing via Tunnel-Current Decay", Nano Letters, Nov. 28, 2007, 7(12), 3854-3858.

He et al, "Transverse Tunneling Through DNA Hydrogen Bonded to an Electrode", Nano Lett. Aug. 2008, 8(8), 2530-2534.

Healy K, et al. "Solid-state nanopore technologies for nanopore-based DNA analysis", Nanomedicine (Land). Dec. 2007;2(6):875-97.

Healy, "Fabrication and Characterization of Nanopores With Insulated Transverse Nanoelectrodes for DNA Sensing in Salt Solution", Electrophoresis, Dec. 2012, 33(23), 3488-3496.

Healy, K., "Nanopore-Based Single-Molecule DNA Analysis", Nanomedicine, Aug. 2007, 2(4), 459-481.

Huang et al, "Recognition Tunneling Measurement of the Conductance of DNA Bases Embedded in Self-Assembled Monolayers", Journal of Physical Chemistry C Nanomater Interfaces, Dec. 9, 2010, 114(48), 20443-20448.

Huang et al, , "Identifying Single Bases in a DNA Oligomer With Electron Tunnelling", Nature Nanotechnology, Dec. 2010, 5(12), 868-873.

Ivanov et al, "DNA Tunneling Detector Embedded in a Nanopore", Nano Letters, Jan. 12, 2011, 11(1), 279-285.

Jiang et al, "Fabrication of nanopores with embedded annular electrodes and transverse carbon nanotube electrodes" Journal of Physics: Condensed Matter, Oct. 29, 2010, 22, 454114.

Kasianowicz JJ, et al. "Characterization of individual polynucleotide molecules using a membrane channel", Proc Natl Acad Sci U SA. Nov. 26, 1996;93(24):13770-3.

Kim KS, et al. "Large-scale pattern growth of graphene films for stretchable transparent Electrodes", Nature. Feb. 5, 2009;457(7230):706-10. Epub Jan. 14, 2009.

Krapf, D et al. Fabrication and Characterization of Nanopore-Based Electrodes With Radii Down to 2 nm. Nano letters. Dec. 8, 2005, vol. 6, No. 1, pp. 105-109.

Krems et al, "Effect of Noise on DNA Sequencing via Transverse Electronic Transport", Biophysical Journal, Oct. 7, 2009, 97(7), 1990-1996.

Lagerqvist et al, "Fast DNA Sequencing via Transverse Electronic Transport", Nano Letters, Apr. 2006, 6(4), 779-782.

Li et al., "Ion-beam sculpting at nanometer length scales", Nature, Jul. 12, 2001, vol. 412, pp. 166-169.

Li J, et al. "DNA molecules and configurations in a solid-state nanopore microscope", Nat Mater. Sep. 2003;2(9):611-5. Epub Aug. 24, 2003.

Li J, et al. "Ion-beam sculpting at nanometre length scales", Nature. Jul. 12, 2001;412(6843): 166-9.

Li X, et al. "Large-area synthesis of high-quality and uniform graphene films on copper foils", Science. Jun. 5, 2009;324(5932):1312-4. Epub May 7, 2009.

Liang, X and Chou, S.Y., "Nanogap Detector Inside Nanofluidic Channel for Fast Real-Time Label-Free DNA Analysis", Nano Letters, May 2008, 8(5), 1472-1476.

Liu H, et al. "Translocation of single-stranded DNA through single-walled carbon nanotubes", Science. Jan. 1, 2010;327(5961):64-7.

Liu Z, et al. "Open and closed edges of graphene layers", Phys Rev Lett. Jan. 9, 2009;102(1):015501. Epub Jan. 5, 2009.

Lu et al., "In Situ Electronic Characterization of Graphene Nanoconstrictions Fabricated in a Transmission Electron Microscope", Nano Letters, 2011, 11(12), 5184-5188.

Choi et al, "Nanotechnology for Early Cancer Detection," Sensors, vol. 10, No. 1, Jan. 6, 2010, pp. 428-455.

(56) References Cited

OTHER PUBLICATIONS

Meller et al., "Rapid Fabrication of Uniformly Sized Nanopores and Nanopore Arrays for Parallel DNA Analysis", Adv. Mater., 2006, 18, 3149-3153.
Neely et al, "A single-molecule method for the quantitation of microRNA gene expression," Nat Methods, vol. 3, No. 1, Jan. 2006, pp. 41-46.
Wanunu et al, "Rapid electronic detection of probe-specific microRNAs using thin nanopore sensors," Nature Nanotechnol ePub, vol. 5, No. 11, Oct. 24, 2010, pp. 807-814.

* cited by examiner

Hetero pores HfO$_2$/SiN$_x$

ALD HfO$_2$ 30 cycles; ~3nm
RIE etch, 10 nm SiN$_x$ left
Thickness 10 + 3 = 13 nm TEM F200 drilling ~ 4 nm pore
HfO$_2$ recrystallization region ~ 20nm wide Piranha cleaning 10 mins $G_{1M\_KCl}$ ~ 158 nS @ 100 mV
$d_{calc}$ = 23 nm (w/ t = 13 nm)

STABLE NANOPORES AND NANOPORE ARRAYS FOR IONIC AND OTHER MEASUREMENTS

CROSS-REFERENCE TO RELATED APPLICATIONS

This application claims priority to and the benefit of U.S. Provisional Application No. 63/003,434, "Stable Nanopores And Nanopore Arrays For Ionic And Other Measurements" (filed Apr. 1, 2020), the entirety of which application is incorporated by reference herein for any and all purposes.

GOVERNMENT RIGHTS

This invention was made with government support under HG009189 and 1542707 awarded by the National Institutes of Health and the National Science Foundation. The government has certain rights in the invention.

TECHNICAL FIELD

The present disclosure relates to the field of solid-state nanopore devices.

BACKGROUND

Nanopores are useful in various applications, including DNA sequencing and molecular filtration. Solid-state nanopores are preferable over their biological counterparts for applications requiring durability and operation under a wider range of external parameters yet few studies have focused on optimizing their robustness.

Solid-state nanopores, however, are not always stable over time, as their size and other characteristics can change, especially with exposure to salt solutions. Accordingly, there is a need in the field for improved solid-state nanopore devices.

SUMMARY

In meeting the described challenges, the present disclosure provides etch-resistant nanopore components, comprising: a first membrane, the first membrane having a pore extending therethrough, the pore defining an edge and defining an inner wall; and a coating of hafnium oxide surmounting at least a portion of the edge and the inner wall of the pore, the pore having, inclusive of the coating of hafnium oxide, a narrowest cross-sectional dimension of from about 1 nm to about 100 nm.

Also provided are methods, comprising: translocating a macromolecule through the pore of a component according to the present disclosure.

Further provided are methods, comprising: forming a pore extending through a first membrane, the pore defining an edge and an inner wall; and applying a hafnium oxide coating so as to surmount at least a portion of the edge of the pore, the inner wall of the pore, or both, the pore having, inclusive of the coating of hafnium oxide, a narrowest cross-sectional dimension of from about 1 nm to about 100 nm. As described elsewhere herein, the hafnium oxide can be applied such that the hafnium oxide does not completely occlude the pore.

Additionally disclosed are methods, comprising: measuring a first ionic conductance value measured across a nanopore to an estimated diameter of the nanopore and correlating the first ionic conductance value to a first estimated diameter of the nanopore.

Further provided are methods, comprising: forming a pore extending through a first membrane, the pore defining an edge and an inner wall and the pore further defining a narrowest cross-sectional dimension; contacting the first membrane with a salt solution under conditions sufficient to effect an etching of the pore that increases the narrowest cross-sectional dimension; and applying a hafnium oxide coating so as to surmount at least a portion of the edge and at least a portion of the inner wall.

Further provided are components, comprising: a first membrane, the first membrane defining one or more pores formed therein, an amount of hafnium oxide surmounting at least a portion of the one or more pores of the first membrane; a second membrane, the second membrane defining a thinned region and defining a pore formed through the thinned region, the first membrane and the second membrane being arranged such that a line can be drawn so as to extend through the thickness of the first membrane and the thickness of the second membrane.

Also disclosed are methods, comprising: translocating a macromolecule through the pore of a component according to the present disclosure, e.g., any one of Aspects 34-35.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In the drawings, which are not necessarily drawn to scale, like numerals may describe similar components in different views. Like numerals having different letter suffixes may represent different instances of similar components. The drawings illustrate generally, by way of example, but not by way of limitation, various aspects discussed in the present document. In the drawings.

Figure 1A:
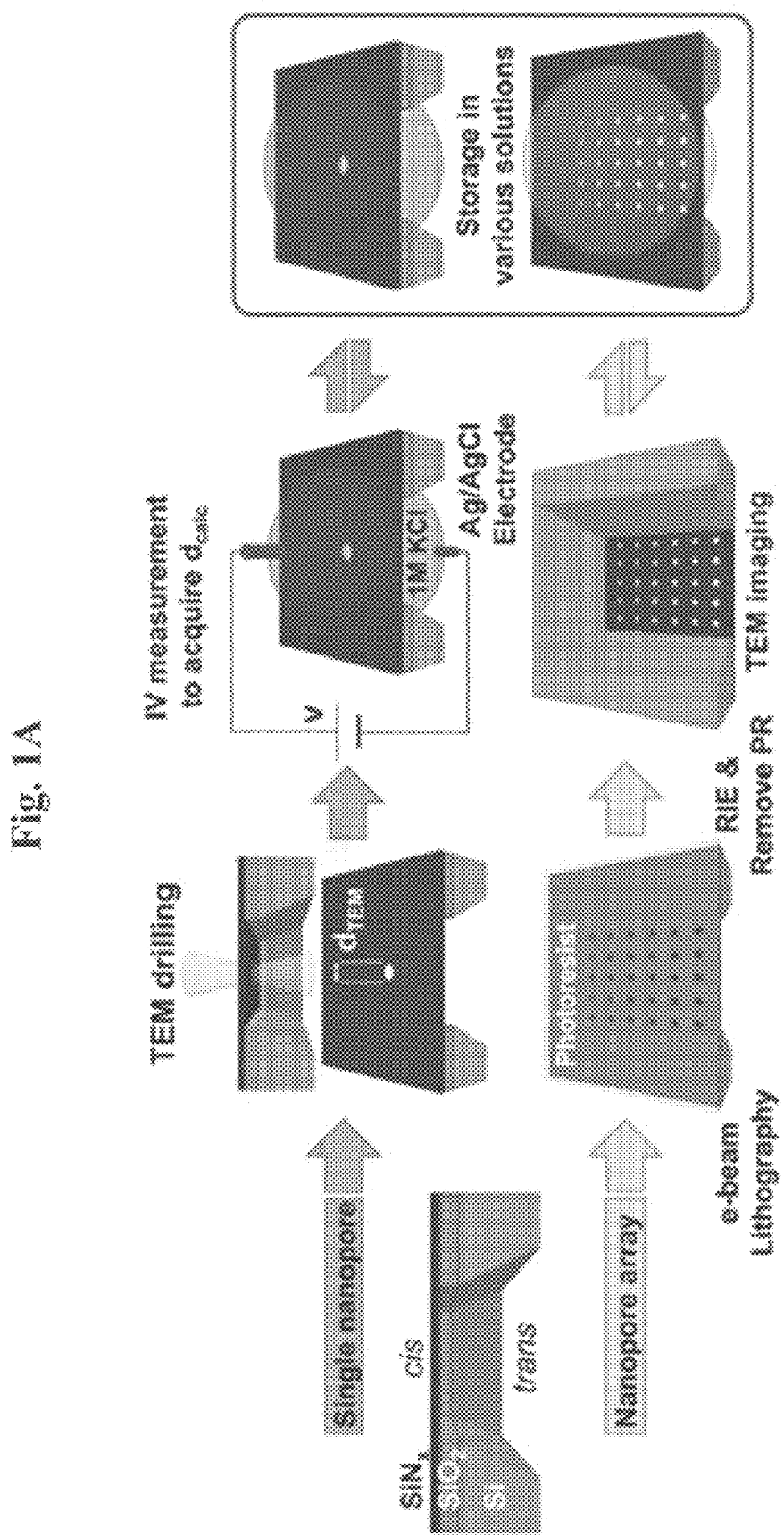
FIG. 1. Schematic and images of two nanopore fabrication methods. (a) Schematic showing the fabrication process of (blue arrow) individual nanopores using TEM drilling and (green arrow) nanopore arrays using electron beam lithography (EBL) and reactive ion etching (RIE). After fabrication, TEM-drilled nanopores are first measured to acquire initial conductance, then stored in various salt solutions for a period of time, then ionic measurements are repeated to record the following conductance. Nanopore arrays as fabricated are inspected with TEM to acquire initial diameter, $d_{TEM}$. Repeated TEM inspections are conducted after storage in salt solutions to acquire corresponding $d_{TEM}$. (b) Optical image of $SiN_x/SiO_2/Si$ chip with a suspended $SiN_x$ membrane. (c) TEM image of a single $SiN_x$ nanopore with $d_{TEM}$~5 nm. (d) TEM image of a nanopore array with $d_{TEM}$~55 nm. (Inset) Low-magnification TEM image demonstrates nanopore array covered the whole suspended $SiN_x$ membrane with N~150,000. (e) Schematic of final pore shape for the two processes described in (a). (Left) TEM drilling results in an hourglass-shaped pore due to the Gaussian-like nature of the electron beam (see FIG. 3), while (right) RIE creates a more cylindrical pore (see FIG. 4).

To further accommodate our observation of decreasing increment of conductance over time, we propose another geometric model assuming constant pore thickness, $t_{eff}$, with varying diameter etch rate over time, when the diameter of pore is smaller than $d_{EELS}$. The fitting line was the result of calculated conductance with diameter etch rates varying every two days, starting with ε=1.9 nm/day, and later decreased to ε=1.15 nm/day after 10 days. Assuming the diameter of pore exceeds $d_{EELS}$ after 12 days, ε is then set to be constant, 1 nm/day. Inset shows our acquired G value up to 78 days of storage in 1M KCl (see Table 2), overlaid with the fitting line from Model 2.

FIG. 3. TEM imaging of pores before and after storage in various salt solutions with structural (ADF) and chemical (EELS) characterization. (a) Images of (top row) various TEM-drilled pores in a 20-nm-thick $SiN_x$ membrane. The bottom row are images of the same pores with the same orientation after 2 days of storage in (i-ii) 1 M KCl, (iii-iv) 1 M KCl (membrane containing no $SiO_2$), (v-vi) 1 M LiCl, and (vii) 1 M $MgCl_2$ (as in FIG. 2c). While pores etch, they maintain their original shape (i.e., circular or elliptical) and expand isotropically. (b) ADF image of a single TEM-drilled pore and a (c) 3D map of ADF intensity (pore vi in FIG. 3a, outlined by purple dashed square). (d) 2D EELS spatial intensity maps of the (green) Si $L_{2,3}$, (yellow) N K, and (red) O K edges at ~100, 400, and 530 eV, respectively. The bottom row shows contour maps as a function of normalized EELS signal intensity. Due to electron beam exposure, TEM-drilled pores display a Si-rich, N-deficient region around the pore edge with a diameter of 20-30 nm.

FIG. 4. TEM imaging, time-dependent etching in 1 M KCl, and EELS data from a nanopore array chip made by EBL and RIE. (a) TEM image of the as-fabricated $SiN_x$ nanopore array, fabricated via electron beam lithography (EBL) and reactive ion etching (RIE). (b) Two TEM images of two different nanopores within this array with diameters close to the mean diameter of the distribution, chosen from the array right after fabrication, and (c) after the array was stored in 1 M KCl for 167 hours. A red dashed circle in (b) outlines the pore region and the same circle is plotted in (c) to visually illustrate how the typical pores grew after etching, together with (d) TEM intensity line scan profiles of these two different pores shown along the orange (0 hour) and blue (167 hours) arrows in (b) and (c), respectively. We show two representative pores with diameters close to the mean of the distributions, to visually illustrate the average pore expansion in the array. (e) Normalized boxplot of $d_{TEM}$ distributions from a series of nanopore array images over time for 900 randomly chosen nanopores. For each histogram/time, the 900 pores were chosen randomly from the center (>5 μm away from the edge) of the membrane (see FIG. 10 for more details). Inset shows five histograms of the measured $d_{TEM}$ distributions over time after 0, 1, 4, 7 and 12 days. (f) ADF image of a single RIE pore and a (g) 3D map of ADF intensity. (h) 2D EELS spatial intensity maps of the (green) Si $L_{2,3}$, (yellow) N K, and (red) O K edges at ~100, 400, and 530 eV, respectively. The bottom row shows contour maps as a function of normalized EELS signal intensity. Pores formed through EBL and RIE exhibit a more confined Si-rich region and $SiO_2$-rich pore edge.

FIG. 5. Fabrication of pores with electron beam thinning and resistance of $HfO_2$ coating to KCl etching. (a) TEM images of a 20-nm-thick $SiN_x$ membrane (left) before and (right) after 46 hours of storage in 1 M KCl solution. The dashed green lines indicate a thinned $SiN_x$ region (containing no visible pores) formed with electron beam exposure. After KCl storage, a pore forms inside the thinned region while existing pore expanded as expected. (b) Time-dependent plot of $d_{calc}$ for a (black line) bare TEM-drilled $SiN_x$ pore and (blue line) $HfO_2$-coated $SiN_x$ pore. Unlike the bare pore, the coated pore does not exhibit same degree of expansion/etching over a period of 6 days.

FIG. 6. Chemical and structural characteristics of $HfO_2$-coated pores. (a) ADF image of a TEM-drilled $SiN_x$ pore coated with 2.5 nm of $HfO_2$ via ALD. (b) 3D pore map based on ADF Z-contrast showing an increase in intensity/thickness at the pore edge. (c) EELS spot spectra taken on the (blue) bulk $SiN_x$ membrane and (yellow) pore edge with prominent Si, N, O, and Hf edges labeled. (d) 2D EELS spatial intensity maps of the (green) Si K, (yellow) N K, (red) O K, and (purple) Hf $M_4$ edges at ~1850, 400, 530, and 1700 eV, respectively. The bottom row shows contour maps as a function of normalized EELS signal intensity. The ALD coating results in shrinkage of the TEM-drilled pore and a $HfO_2$-rich pore edge.

Figure 7A:
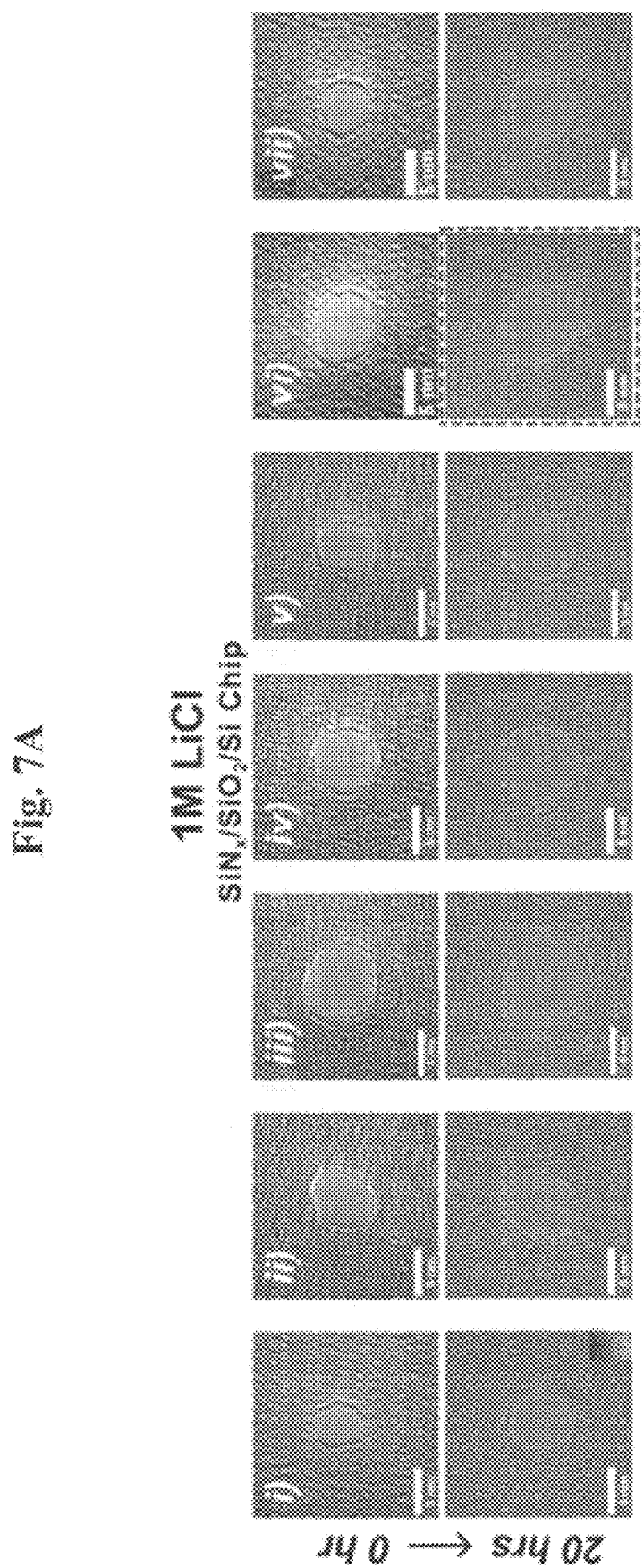
Figure 7B:
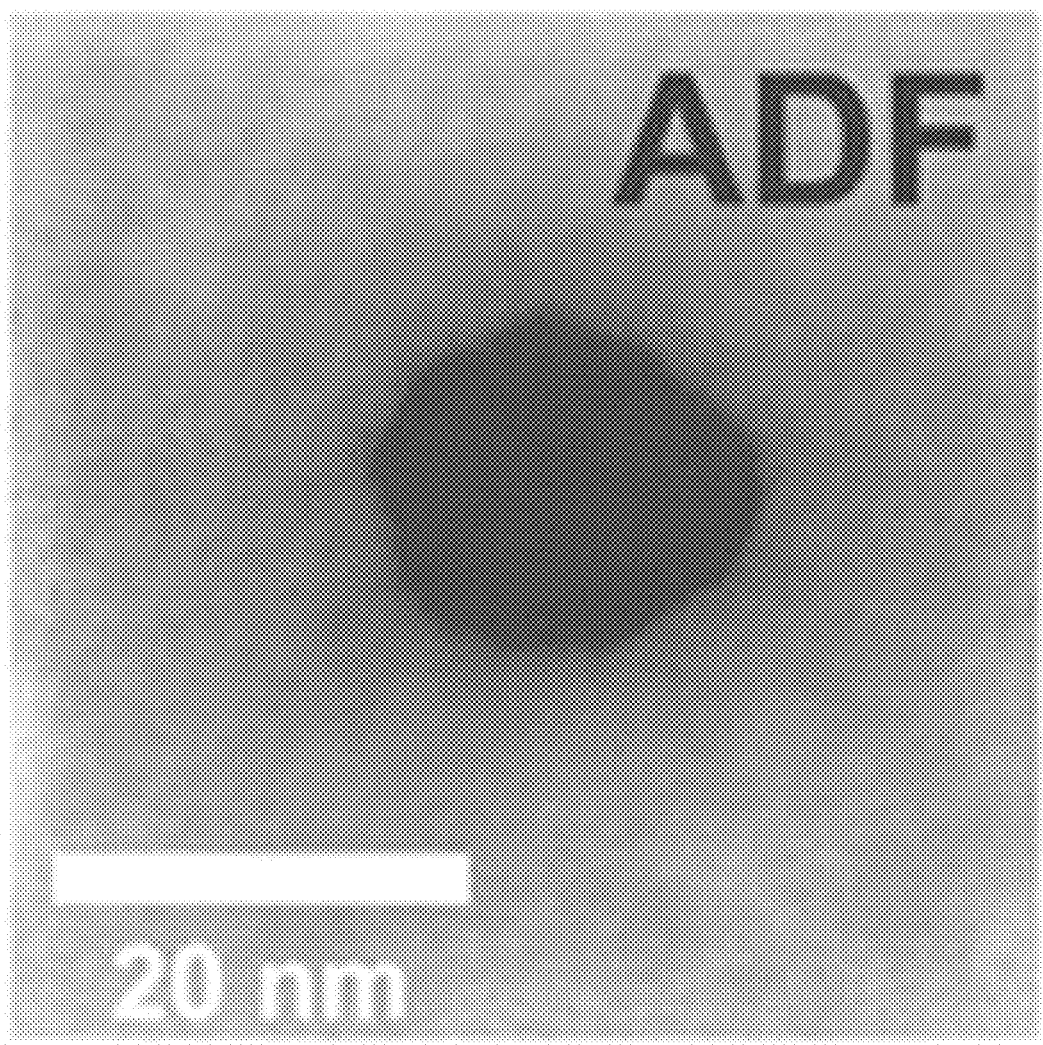
Figure 7C:
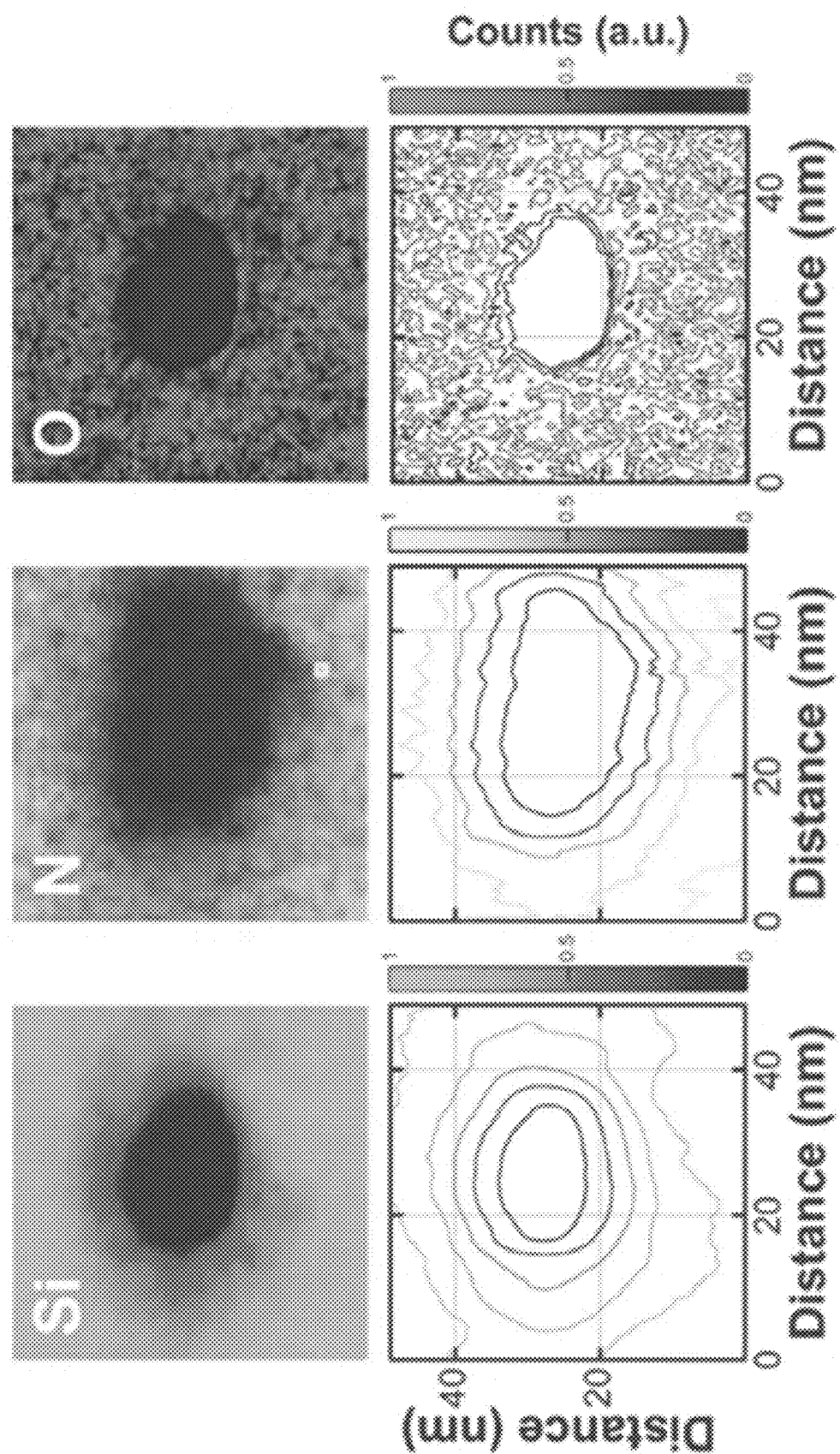

FIG. 7. (a) Series of TEM images of additional seven nanopores, before and after storage in 1M LiCl for 20 hours (not shown in the main text). (b)-(c) Additional EELS 2D spatial composition map was conducted on pore (vi), marked by a purple dashed square in FIG. 7 (a). Contour maps of Si $L_{2,3}$ edge (green) and N K edge (yellow) indicate that the thinned region has a diameter approximately $d_{EELS}$~30 nm. From the O K edge (red) signals, we observe a uniformly distributed layer of native oxide.

Figure 8:
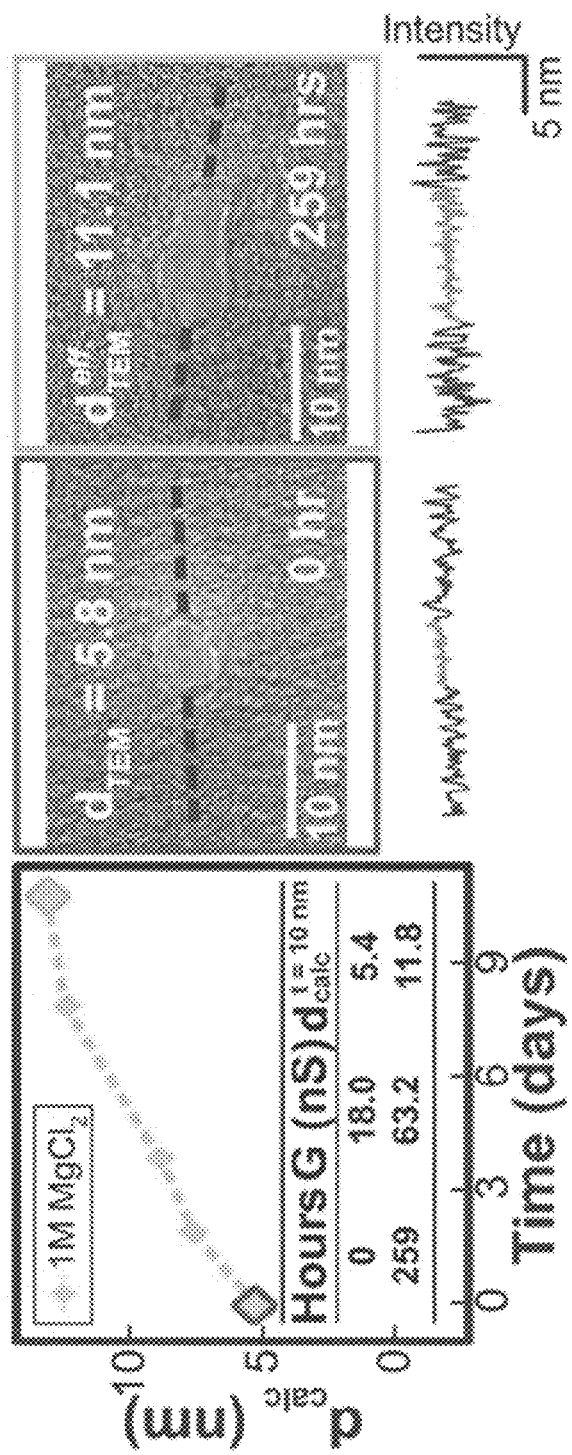

FIG. 8. $d_{calc}$ vs. time for a ~5-nm-diameter pore stored in 1M $MgCl_2$ over 11 days. Corresponding TEM images and TEM line scan profiles for the as-fabricated pore (blue box) and after storage in 1M $MgCl_2$ over 11 days (green box). The calculated pore diameter is listed in the inset. This pore expanded from ~5 nm diameter to ~12 nm diameter. Because this membrane was relatively thin (10 nm), there is little contrast in the TEM line scan between the membrane (blue) and the pore (red) region (there is a higher signal noise above the membrane region).

Figure 9:
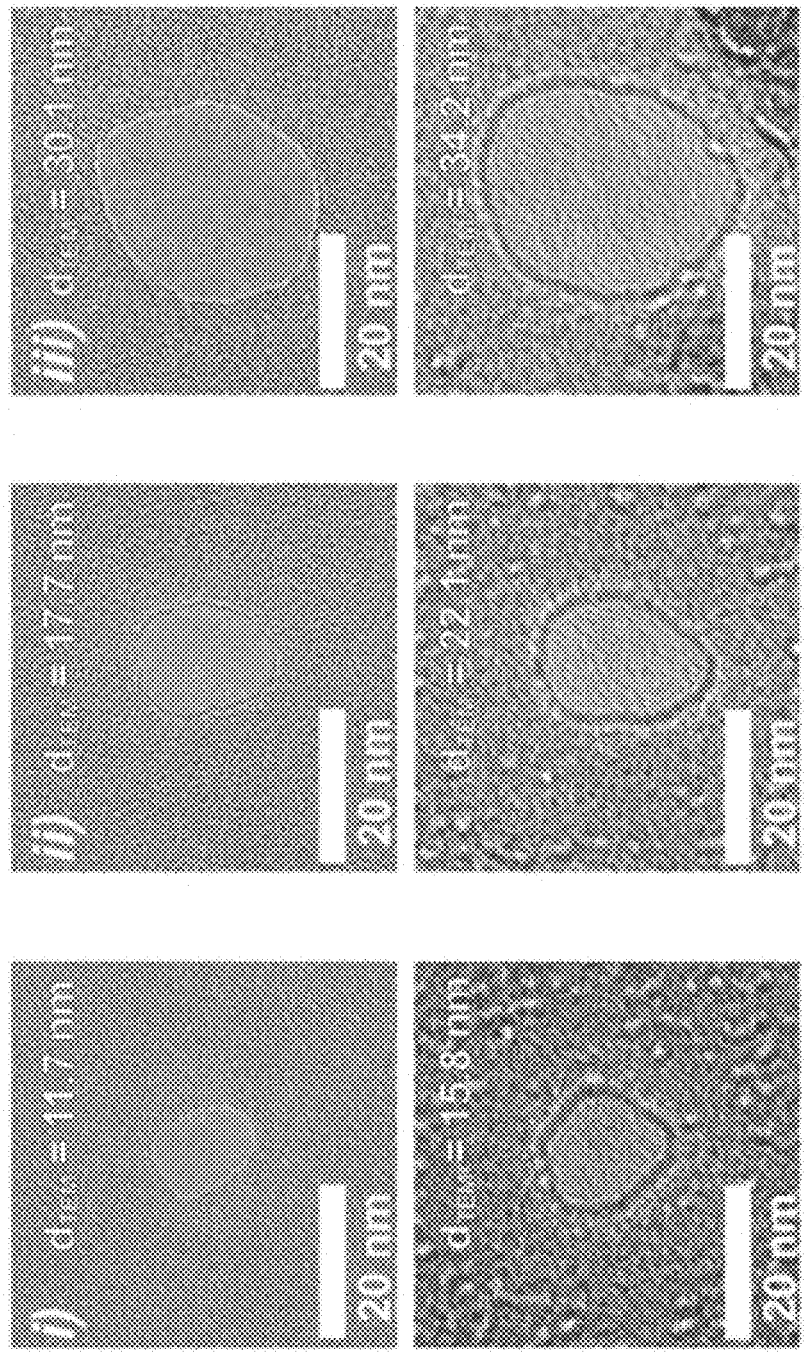

FIG. 9. A commercial, 20-nm-thick silicon nitride membrane chip from SPI Supplies (Model #4163SN-BA) was used to fabricate nanopores via TEM drilling. A series of TEM images of three nanopores is shown, before and after storage in 1M KCl for 48 hours at room temperature and then followed by 1 hour in the same solution heated at 60° C. Corresponding etch rate is then calculated to be A $(d_{TEM})/\Delta t$=2.1±0.1 nm.

Figure 10A:
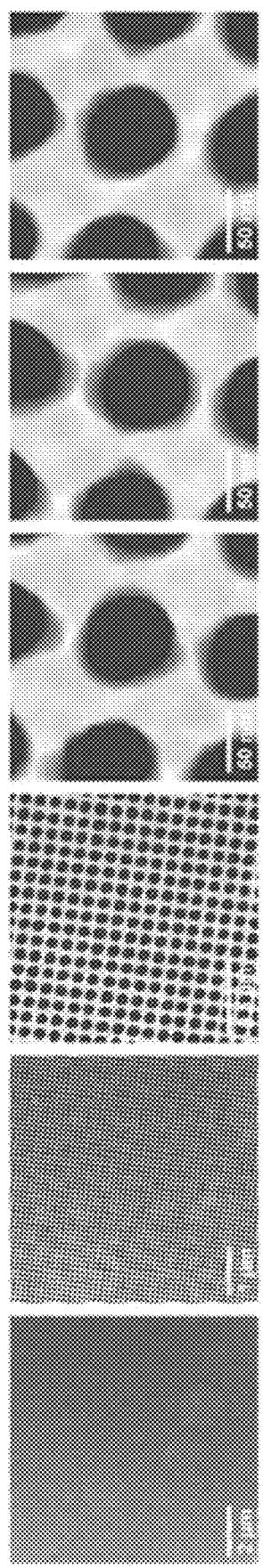
Figure 10B:
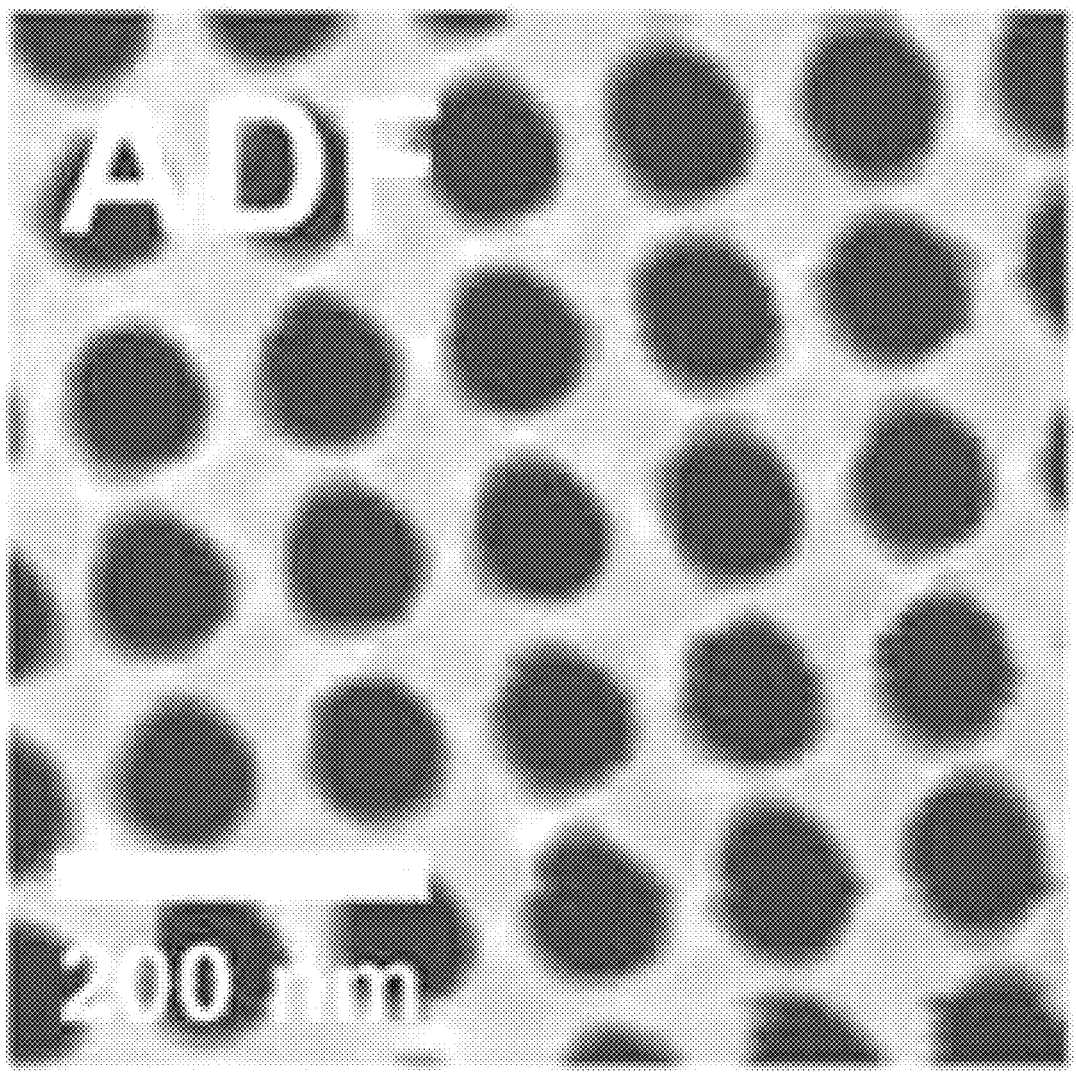
Figure 10C:
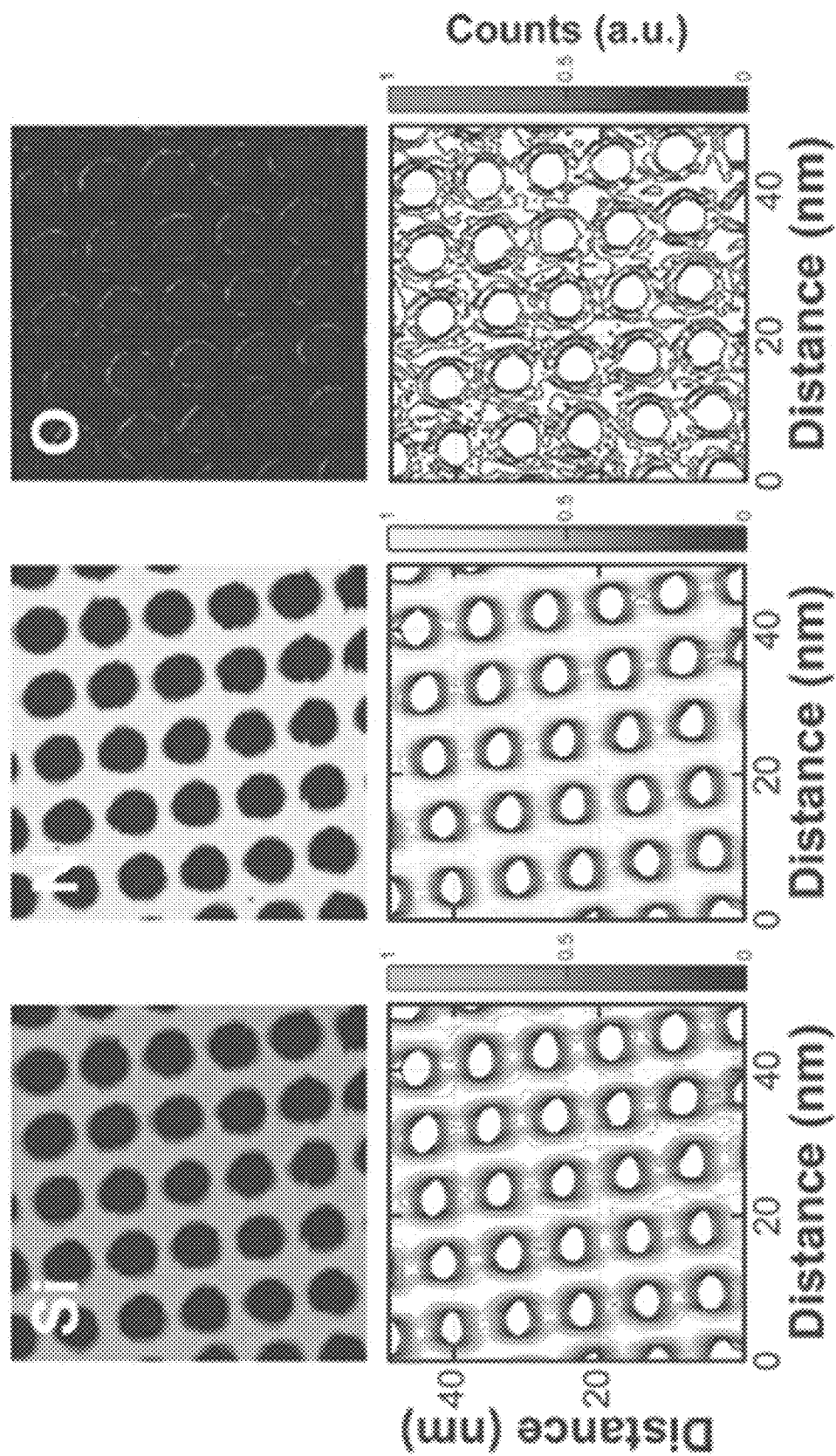

FIG. 10. (a) Series of dark-field (DF) TEM images of a nanopore array after storage in 1M KCl for 167 hours. (b)-(c) Additional EELS 2D spatial composition maps were acquired for a region containing a 5-by-5 array of nanopores. Contour maps of Si $L_{2,3}$ edge (green) and N K edge (yellow)

indicate a more confined, N-deficient region, as opposed to the case of TEM pores. An evenly lit up region of O K edge (red) signals at the pore edge shows that a uniform layer of silicon oxide resides along the pore walls.

Figure 11A:
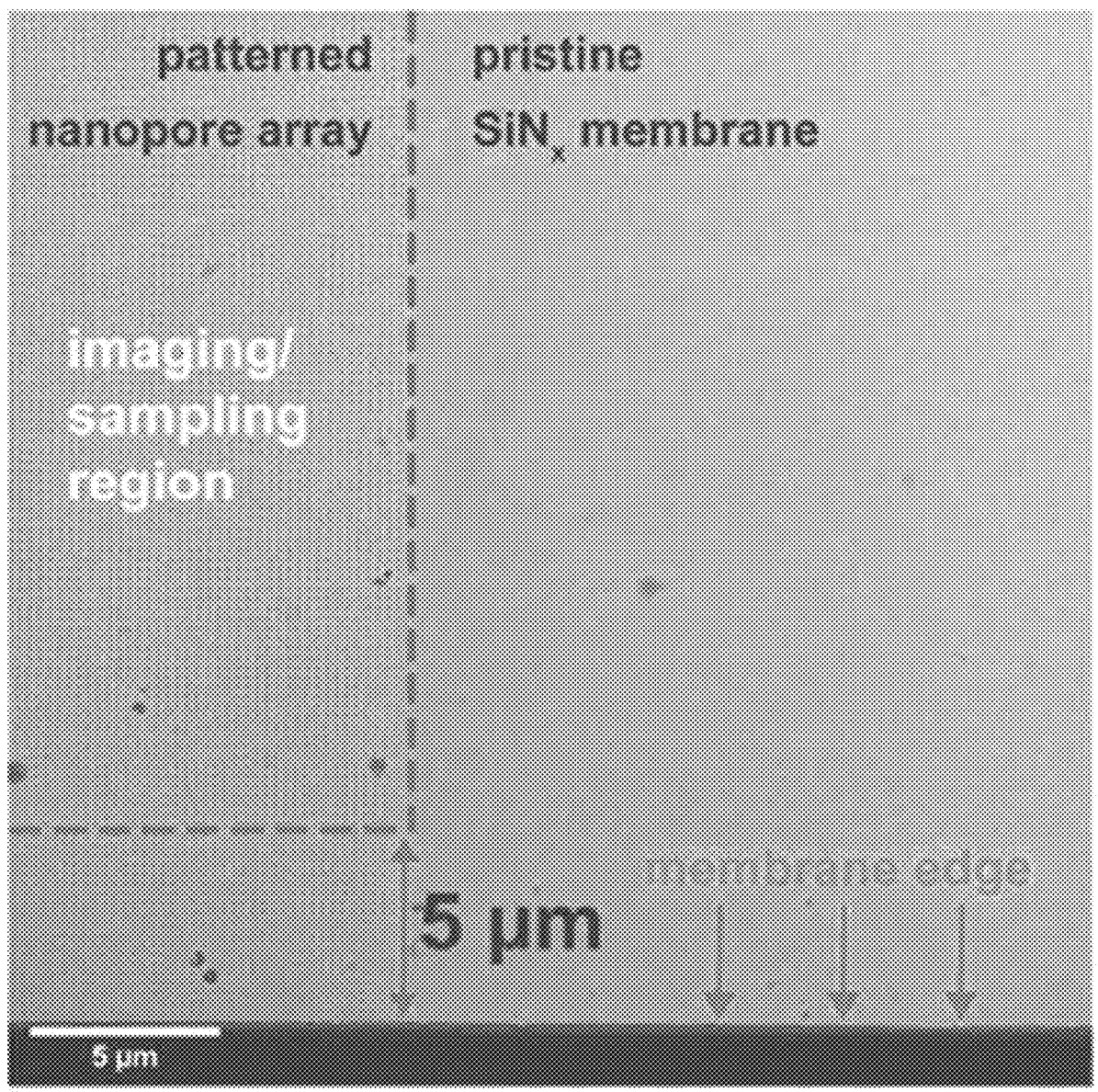
Figure 11B:
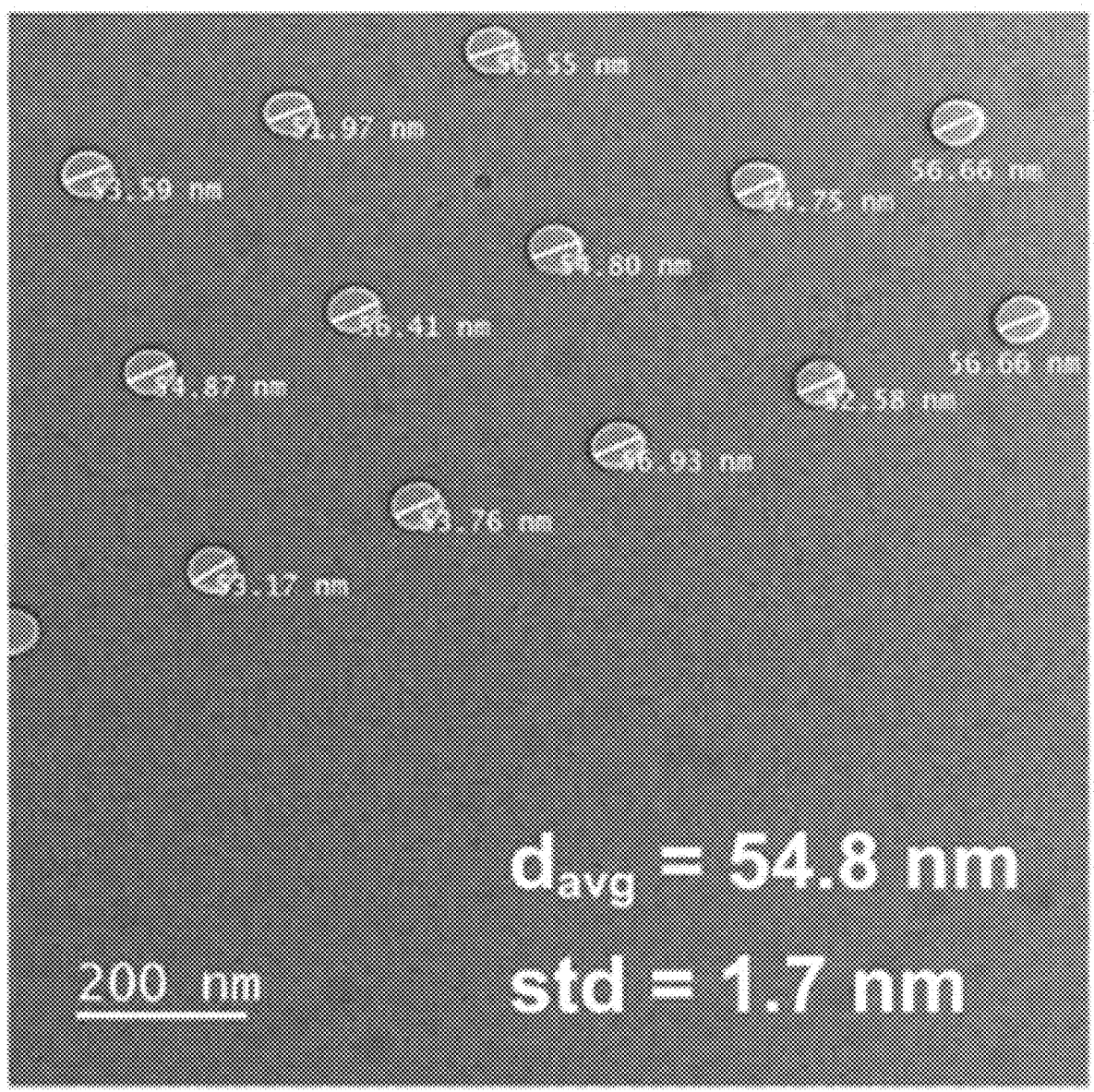

FIG. 11. (a) Low-magnification TEM image of a nanopore array region. Examination and calculation of the distribution of $d_{TEM}$ in FIG. 4e were randomly selected within the imaging/sampling region (enclosed by blue dashed line), which was chosen to be 5 μm away from the membrane edge. (b) a high-magnification TEM image taken within imaging/sampling region was shown here. We then acquire the variation of diameters within nanopore arrays to be, $(d_{TEM})$=54.8±1.7 nm.

Figure 12:
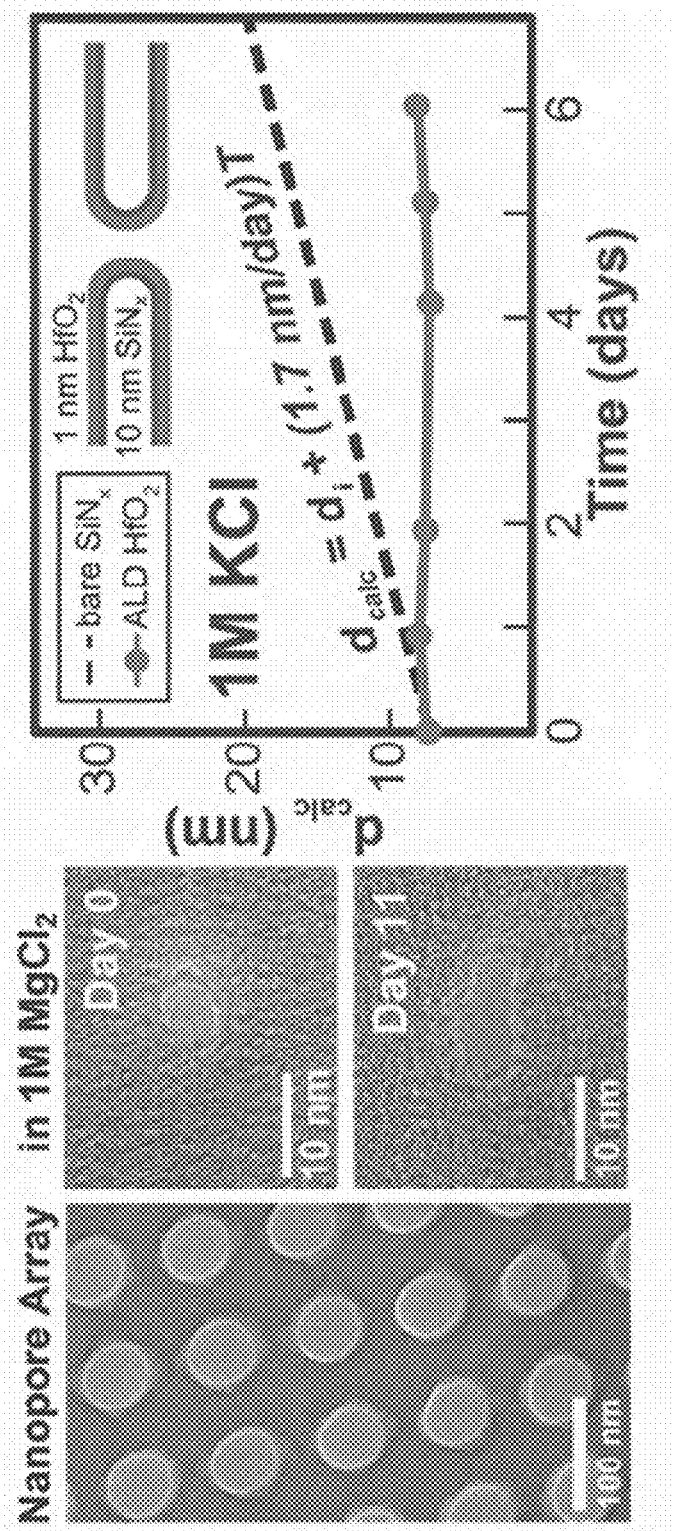

FIG. 12 provides exemplary results. As shown in the left panel, pores that lack a hafnium oxide coating are etched over time when contacted with $MgCl_2$. As shown in the right panel, the disclosed pores can include a coating of hafnium oxide on the edge of the pore and also on the inner wall of the pore; the coating can also extend outwardly over the membrane away from the edge of the pore. As shown in the right panel, the diameter of a hafnium oxide-coated pore remained essentially constant over 6 days of immersion in 1 M KCl, whereas the diameter of a "bare" SiN pore increased over the course of 6 days of immersion in 1 M KCl.

Figure 13:
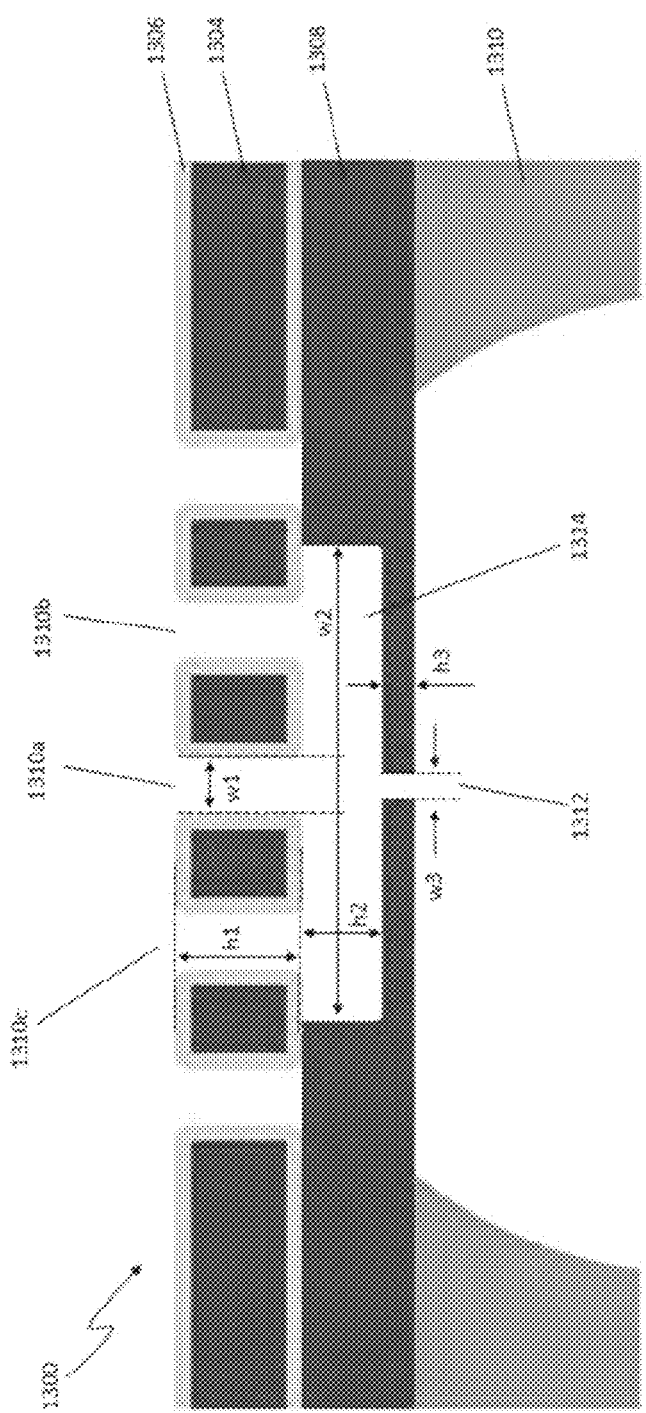

FIG. 13 provides a cross-sectional view of a component according to the present disclosure.

Figure 14:
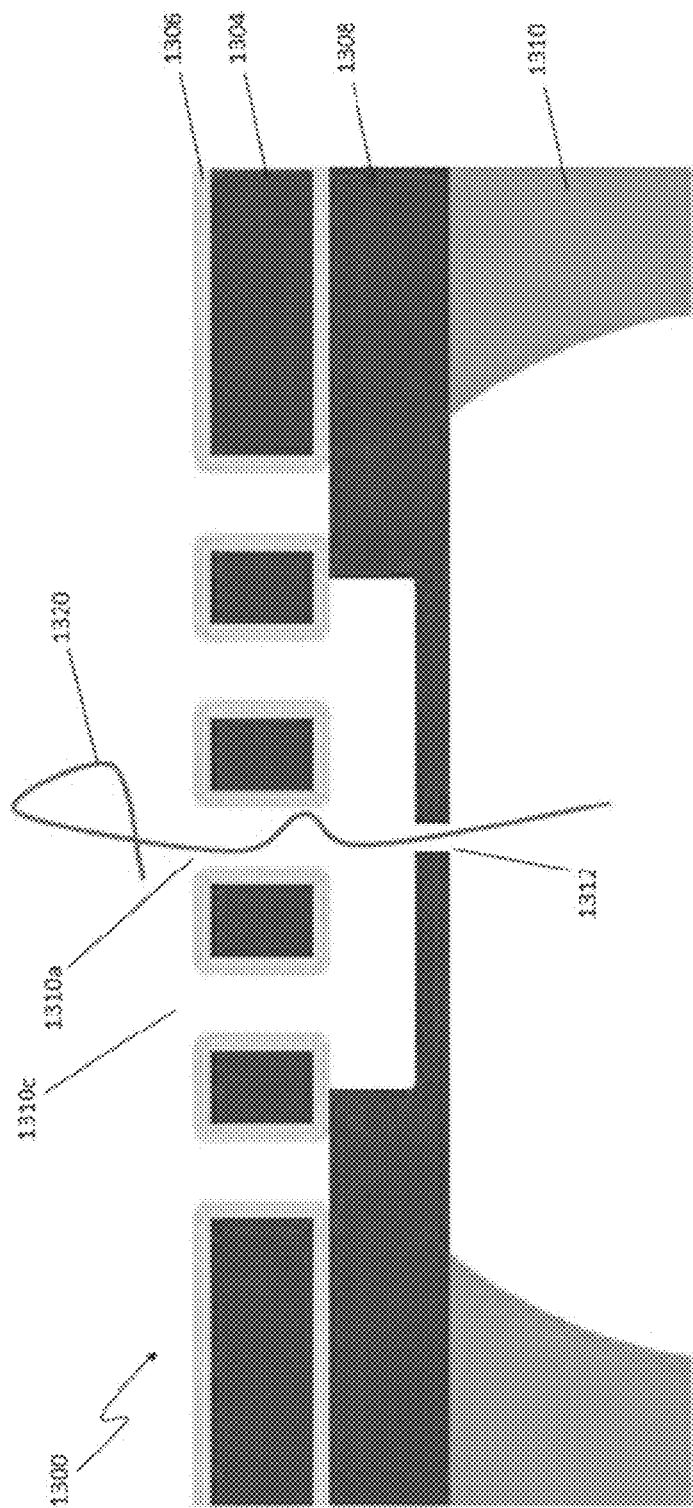

FIG. 14 provides a cross-sectional view of a component according to the present disclosure.

Figure 15:
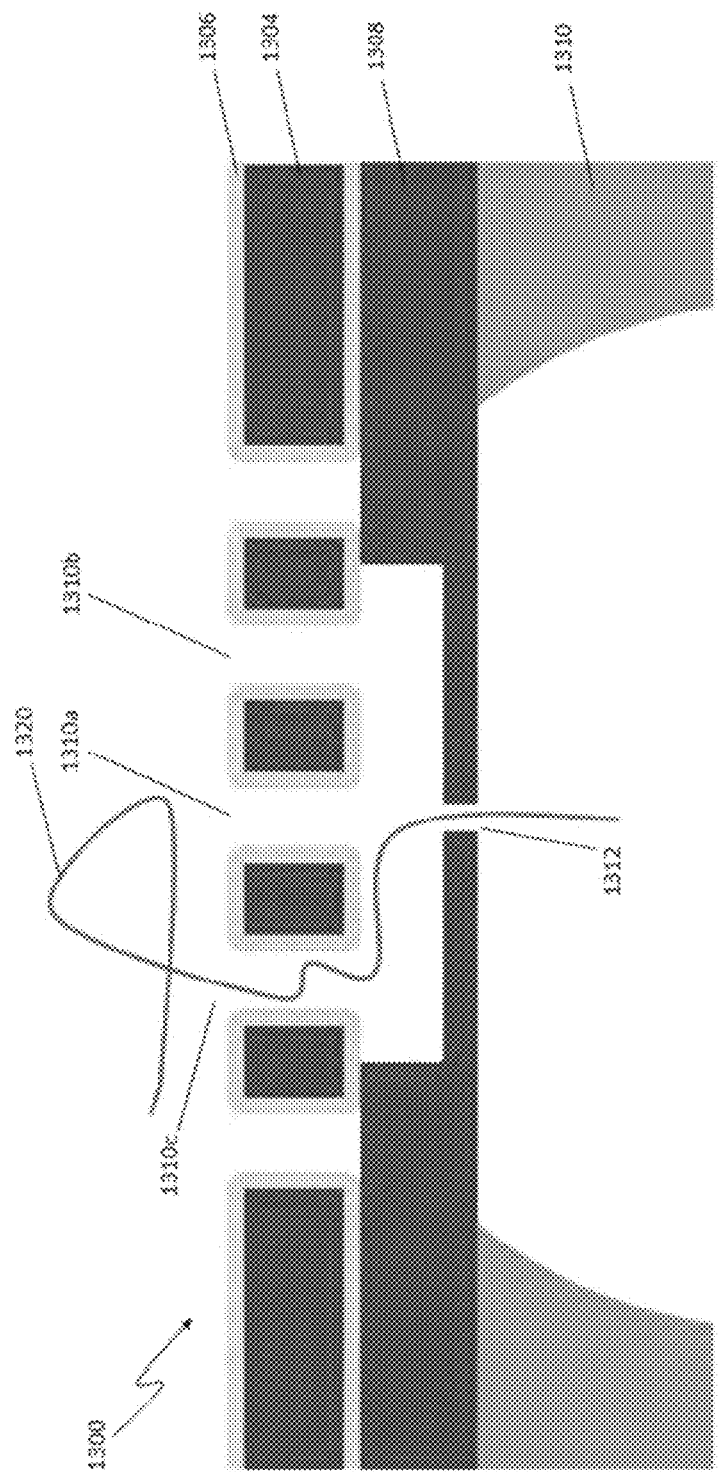

FIG. 15 provides a cross-sectional view of a component according to the present disclosure.

Figure 16:
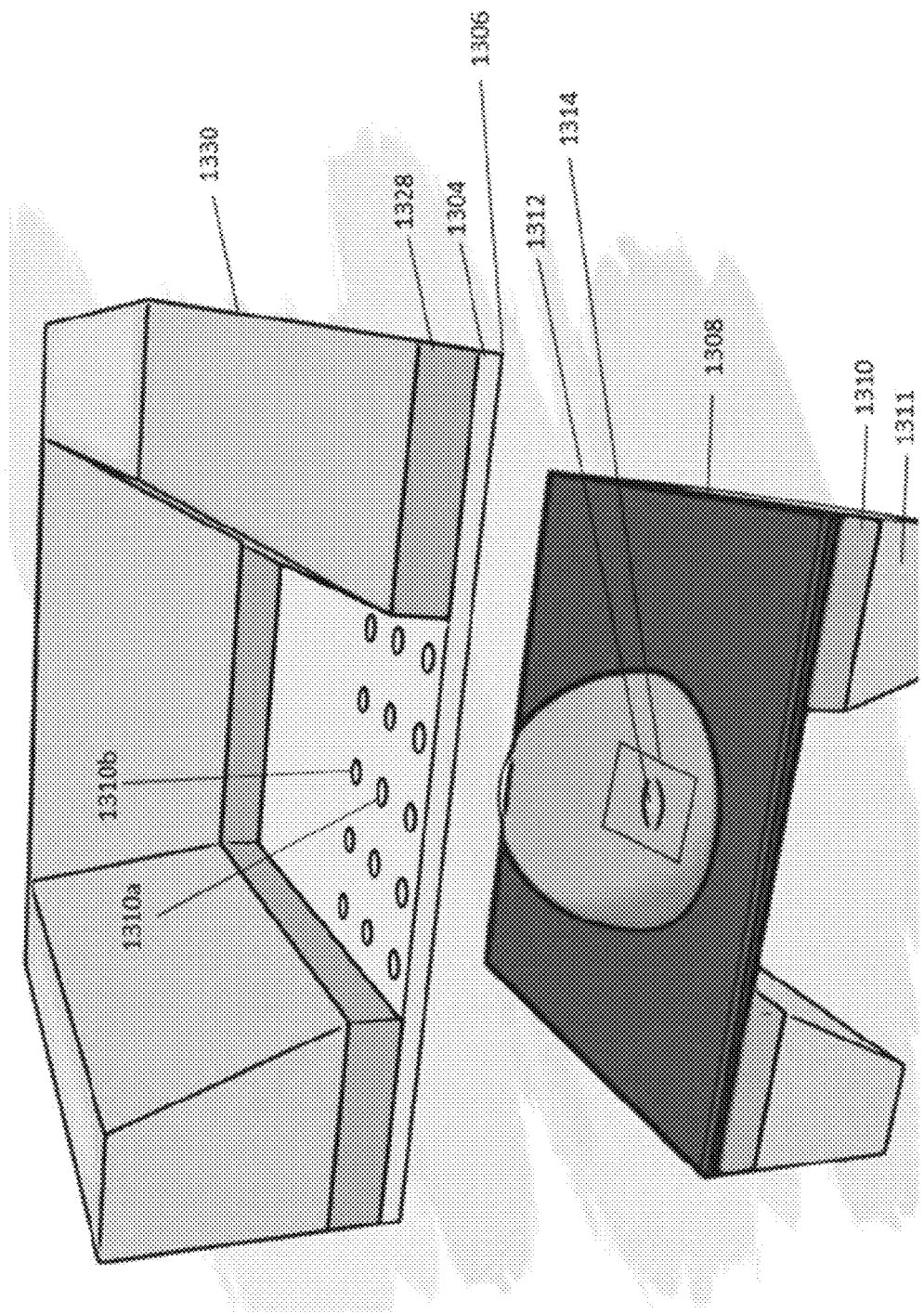

FIG. 16 provides a view of a component according to the present disclosure.

Figure 17:
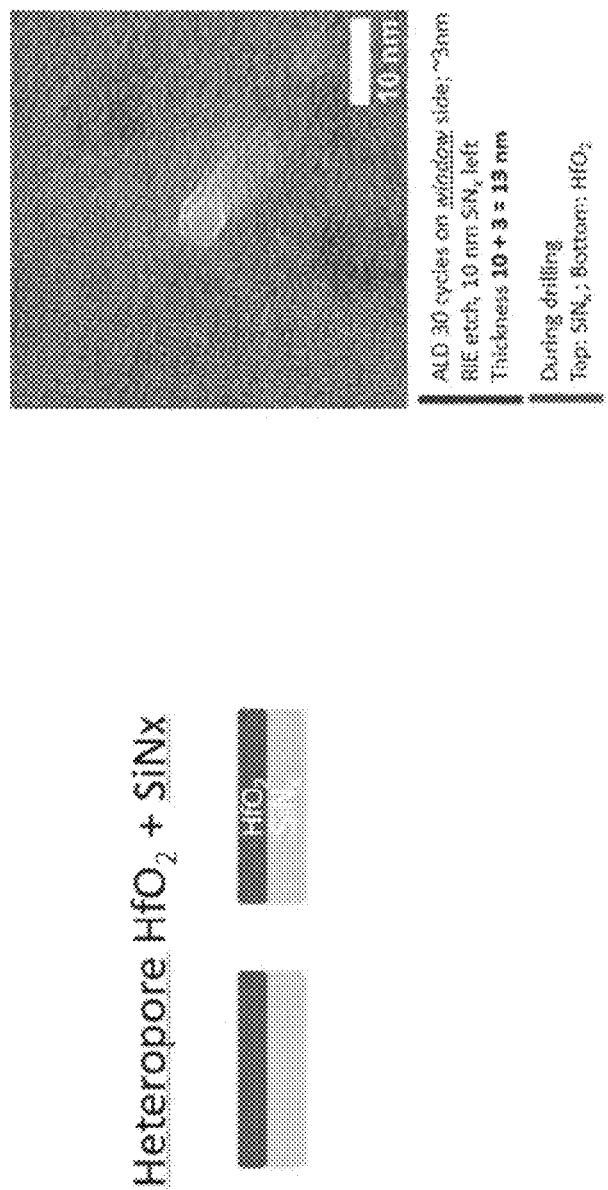

FIG. 17 provides example results of a component according to the present disclosure.

Figure 18:
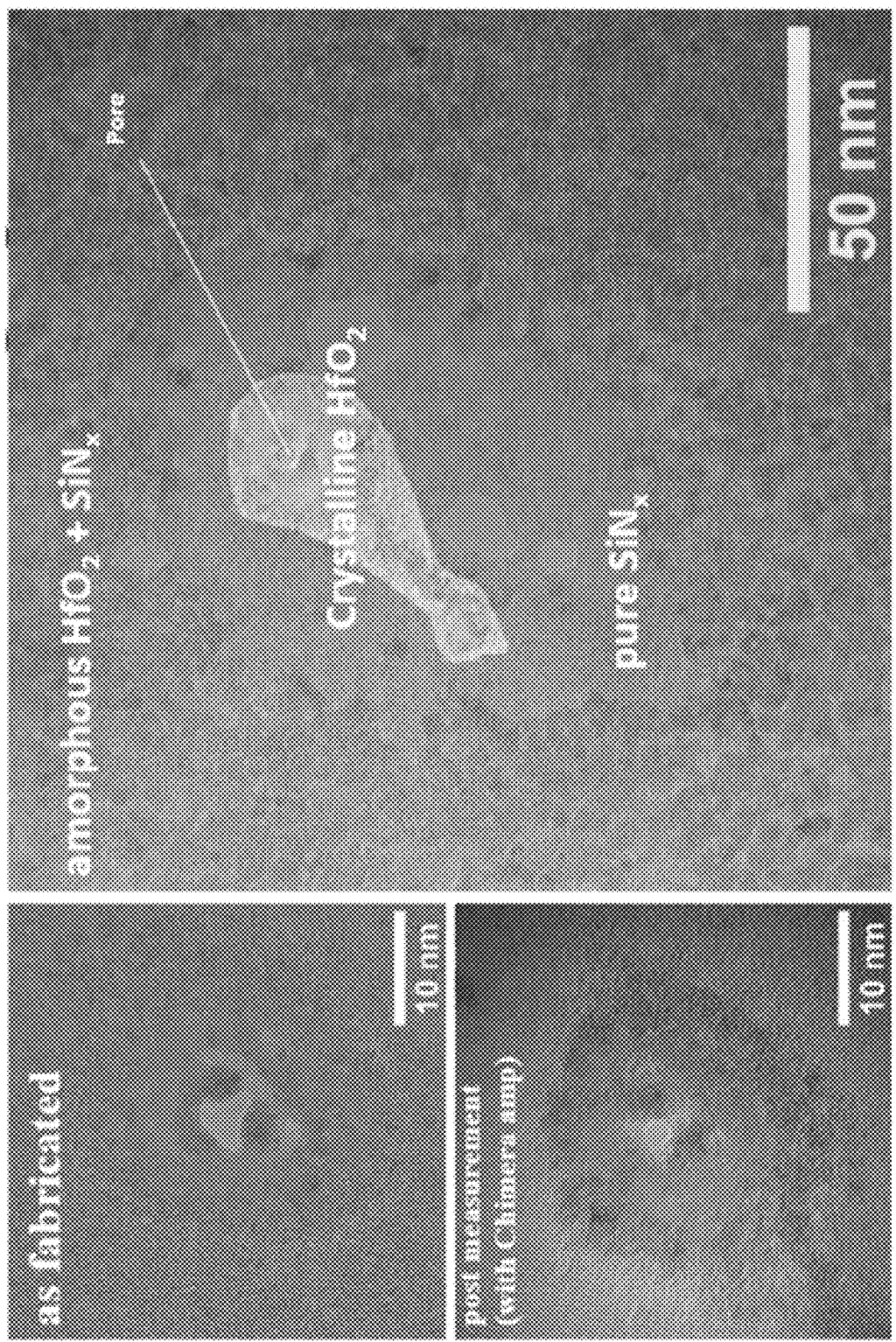

FIG. 18 provides example results of a component according to the present disclosure.

Figure 19:
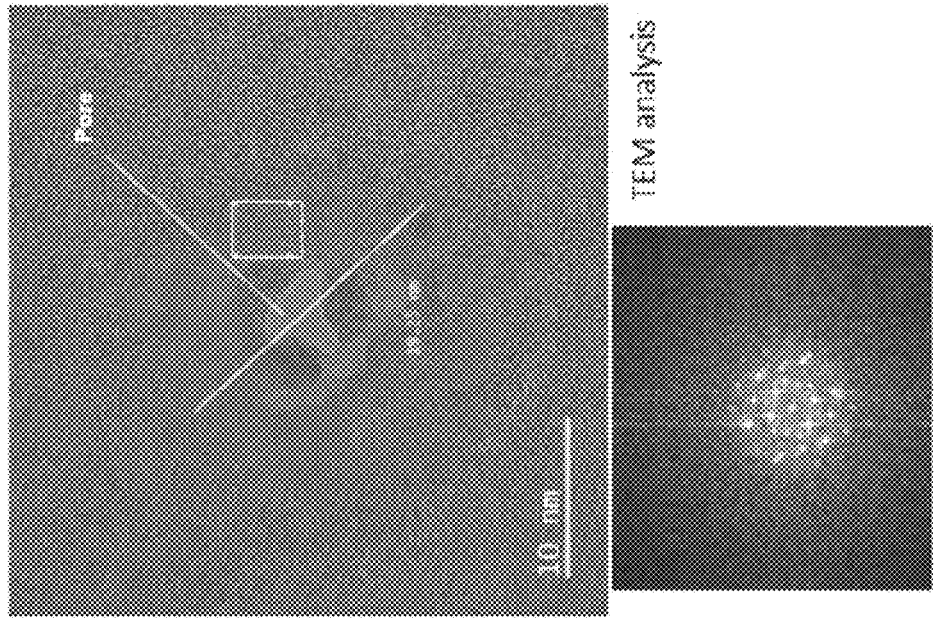

FIG. 19 provides example results of a component according to the present disclosure.

DETAILED DESCRIPTION OF ILLUSTRATIVE EMBODIMENTS

The present disclosure may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention.

Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable, and it should be understood that steps can be performed in any order.

It is to be appreciated that certain features of the invention which are, for clarity, described herein in the context of separate embodiments, can also be provided in combination in a single embodiment. Conversely, various features of the invention that are, for brevity, described in the context of a single embodiment, can also be provided separately or in any subcombination. All documents cited herein are incorporated herein in their entireties for any and all purposes.

Further, reference to values stated in ranges include each and every value within that range. In addition, the term "comprising" should be understood as having its standard, open-ended meaning, but also as encompassing "consisting" as well. For example, a device that comprises Part A and Part B can include parts in addition to Part A and Part B, but can also be formed only from Part A and Part B.

Nanopores are useful in many applications, including DNA sequencing and molecular filtration. Solid-state nanopores are preferable over their biological counterparts for applications requiring durability and operation under a wider range of external parameters yet few studies have focused on optimizing their robustness. We report the lifetime and durability of pores and porous arrays in 10 to 100 nm thick, low-stress silicon nitride ($SiN_x$) membranes. Pores are fabricated using a transmission electron microscope (TEM) and/or electron-beam lithography (EBL) and reactive ion etching (RIE), with diameters from 2 to 80 nm. We store them in various electrolyte solutions (KCl, LiCl, $MgCl_2$) and record open pore conductance over months to quantify pore stability.

Pore diameters increase with time and diameter etch rate increases with electrolyte concentration from ~0.2 to ~3 nm/day for 0.01 to 3 M KCl, respectively. TEM confirms the range of diameter etch rates from ionic measurements. Using electron energy loss spectroscopy (EELS), we observe that a N-deficient region around the edges of TEM-drilled pores. Pore expansion is caused by etching of the $Si/SiO_2$ pore walls, which resembles the dissolution of silicon found in minerals such as silica ($SiO_2$) in salty ocean water. The etching process occurs where the membrane was exposed to the electron beam and can result in pore formation. However, coating pores with a conformal 1-nm-thick hafnium oxide layer prevents expansion in 1M KCl, in stark contrast to bare $SiN_x$ pores (~1.7 nm/day). EELS data reveal the atomic composition of bare and $HfO_2$-coated pores.

Nanopore-based biomolecule, DNA and nanoparticle analysis is a single-molecule and single-particle technique that potentially offers orders of magnitude faster and more economical detection, counting, and analysis than current methods. This includes DNA length measurement, specific sequence detection, single-molecule dynamics, de novo sequencing as well as counting and sizing of nanoscale particles. The basic concept involves using an applied voltage to drive the particle through a nanopore, which separates chambers of electrolyte solution. This voltage also drives a flow of electrolyte ions through the pore, measured as an electric current. When molecules pass through the nanopore, they block the flow of ions, and thus their structure and length can be determined based on the degree and duration of the current reductions.

Silicon nitride ($SiN_x$) pores, first fabricated around 2003 using electron and ion beam drilling of thin $SiN_x$ membranes, have proven robust and useful in biomolecular detection measurements, and are excellent pores for diagnostic and filtering device. Compared to biological protein-based pores, solid-state pores offer a wider range of tunable diameters, more scalable fabrication and higher robustness for environmental applications. Similarly, compared to newer 2D membranes such as graphene, $SiN_x$ has a superior thermal stability and is employed in a wide range of industrial applications. While focus has been on obtaining high signal-to-noise ratios in ionic experiments by thinning pores and optimizing nanopore chips by adding insulating layers, quantifying the durability of these pores has received little attention, and at best, the insights on this topic are scattered within the literature as secondary comments or even contradictory. Because of the particular utility of silicon nitride pores, we focus this study on them and report a quantification and improvements of their lifetime and durability, but it should be understood that silicon nitride is not the only suitable membrane material through which pores can be formed (and which can be coated with hafnium oxide).

In this disclosure, we first demonstrate the fabrication of single nanopores by transmission electron microscope (TEM) drilling, and nanopore arrays by electron beam lithography (EBL) and reactive ion etching, which contain up to hundreds of thousands of nanopores, with high fidelity, in thin $SiN_x$ membranes. By measuring their diameters in two different ways: the first way by calculating diameter, $d_{calc}$, from ionic measurements on single pores; and the second way, by directly measuring the diameter from TEM images of single pores and nanopore arrays, $d_{TEM}$, we quantify the stability of pores placed under typical nanopore operating/storage conditions. We used several salt solutions such as KCl, LiCl, and $MgCl_2$, and characterize the pores over long periods of time (up to ~2 months) and subsequently characterize the effects of salt solutions on $SiN_x$ pore geometry, pore diameter etch rates (up to ~3 nm/day) and ionic transport properties. We confirm quantitative findings from ionic measurements by direct high-resolution transmission electron microscope imaging of both TEM-drilled and EBL fabricated nanopores, confirming the range of pore expansion rates from ionic measurements.

In addition to pore expansion, this etching phenomenon can be exploited for pore formation with selective electron irradiation. As the irradiated section of the $SiN_x$ membrane etches away in salt solution, we observe how a nanopore emerges in the thinnest spot of that region. Electron energy loss spectroscopy (EELS) in an aberration-corrected TEM provides 2D spatial composition maps that give insights into the chemical structure of these pores. TEM-drilled pores exhibit a thinned ring around the pore in which N is depleted, leaving a $Si/SiO_2$-rich region that dissolves in salt solutions at ambient conditions, resulting in slow, long-term pore expansion. For nanopore arrays, we detect $SiO_2$ at the pore walls, but a less extended Si-rich region, as this fabrication process involves top-down etching of the resist-patterned $SiN_x$ membrane. From EELS, we infer that the etching process for both types of pores involves $SiO_2$ dissolution and resembles to the slow dissolution process of silicon found in minerals such as silica ($SiO_2$) and silicates in seawater.

Finally, we tested several surface coatings and present a viable route for mitigating the chemical etching and expansion of nanopores through atomic layer deposition (ALD) of hafnium oxide. We find that a very thin (~1-nm-thick) coating of $SiN_x$ pores with hafnium oxide completely prevents long-term pore expansion, offering a practical solution to fabricating stable and robust nanopores. EELS 2D spatial maps further reveal how ALD coating affects the previous TEM-drilled pore structure.

Results and Discussion
Nanopore Fabrication

FIG. 1 demonstrates the fabrication of single nanopores and nanopore arrays in suspended $SiN_x$ membranes. The 5-mm square silicon platforms (light gray) coated with 5-μm $SiO_2$ (orange), unless noted otherwise (see FIG. 3a), and a 10-nm and 20-nm thick layer of low-stress $SiN_x$ are first produced through conventional microfabrication techniques (FIG. 1a). As shown in the top row of FIG. 1a (blue arrow), single nanopores are formed in TEM imaging mode by focusing the transmission electron beam onto the $SiN_x$ membrane for 5-10 seconds (total dose ~$8.0 \times 10^{11}$ $e^-/nm^2$). Here, we utilize a high-resolution mode TEM operating at 200 kV with a beam current of 20 nA. By providing real-time feedback through TEM imaging, this technique allows the formation and observation of pores with precise diameters, $d_{TEM}$.

The workflow for nanopore arrays fabricated by e-beam lithography is demonstrated schematically in the bottom row of FIG. 1a (green arrow). A similar approach was reported in 2018 for fabricating nanopores in freestanding graphene and $SiN_x$ membranes. $Si/SiO_2/SiN_x$ chips are first coated with a ZEP520A polymer resist. With dots-on-the-fly electron beam lithography (EBL), pore arrays are patterned onto a 50-μm square region. After resist development, reactive ion etching with trifluoromethane and oxygen ($CHF_3/O_2$) is utilized for $SiN_x$ removal in the exposed circular regions to define the pores. By tuning the shot pitch to 100 nm, the highly perforated membrane still retains its structural integrity without collapsing.

Figure 1B:
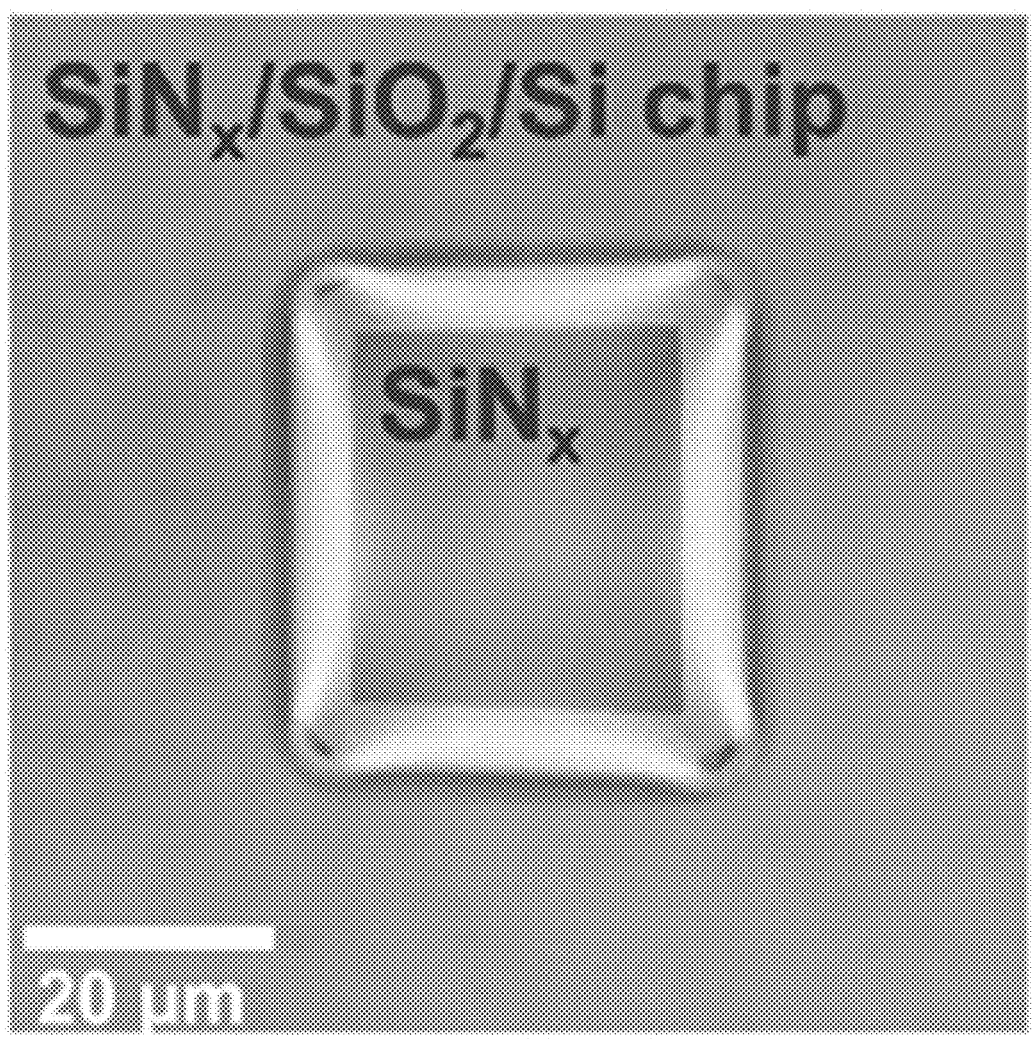
Figure 1C:
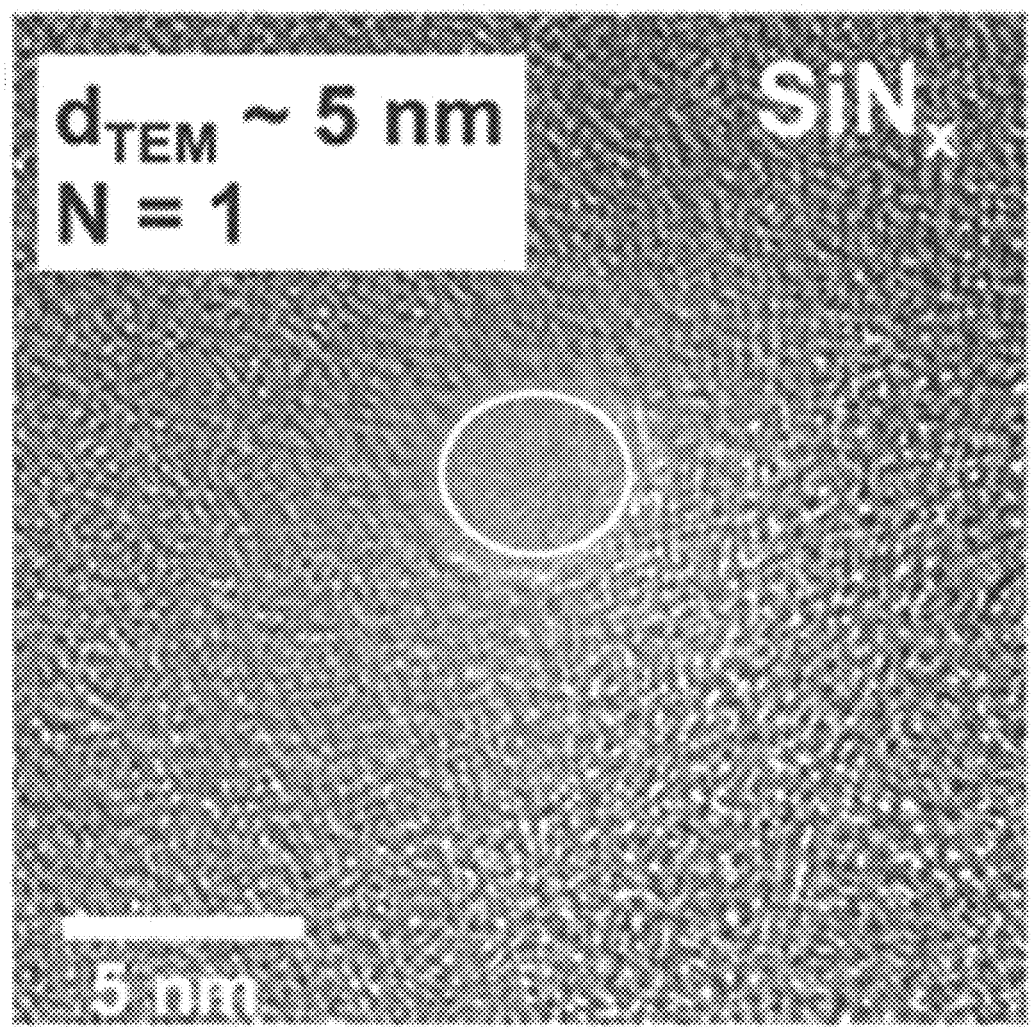
Figure 1D:
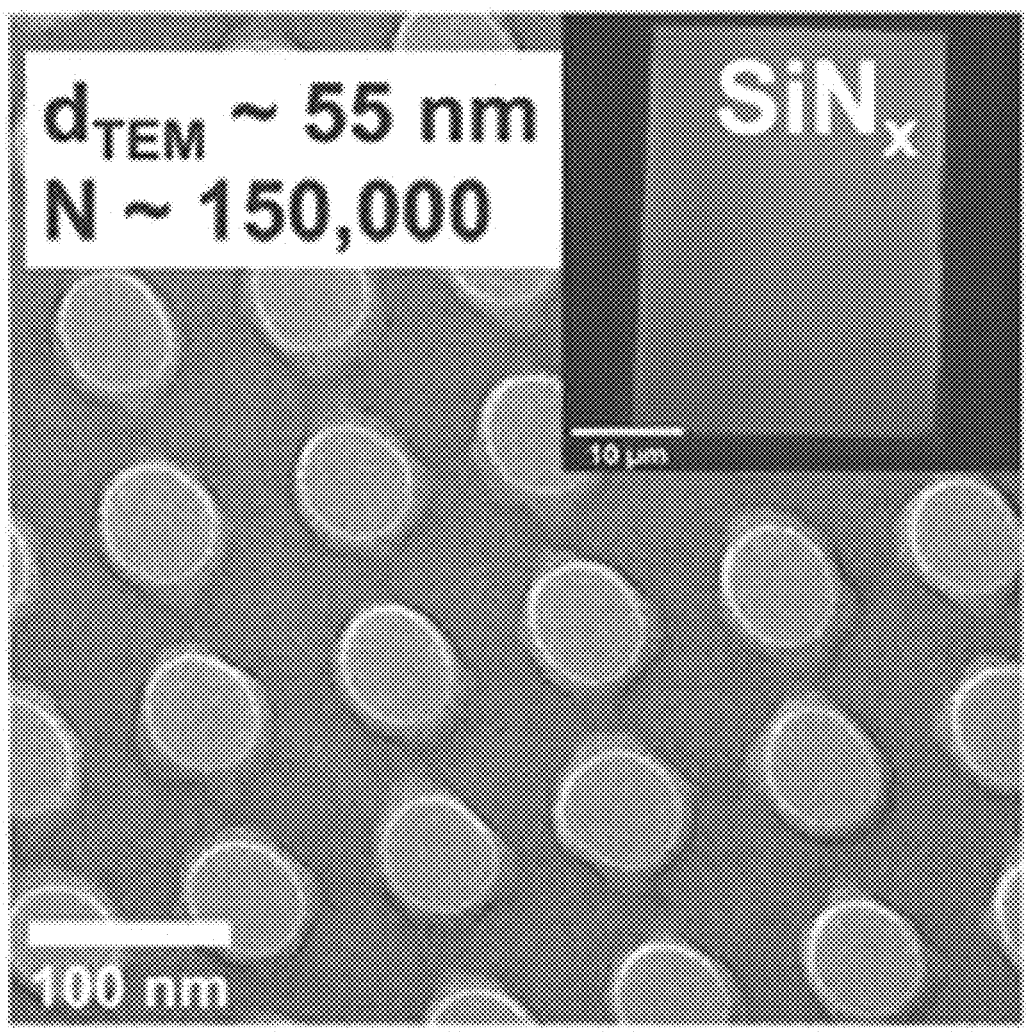
Figure 1E:
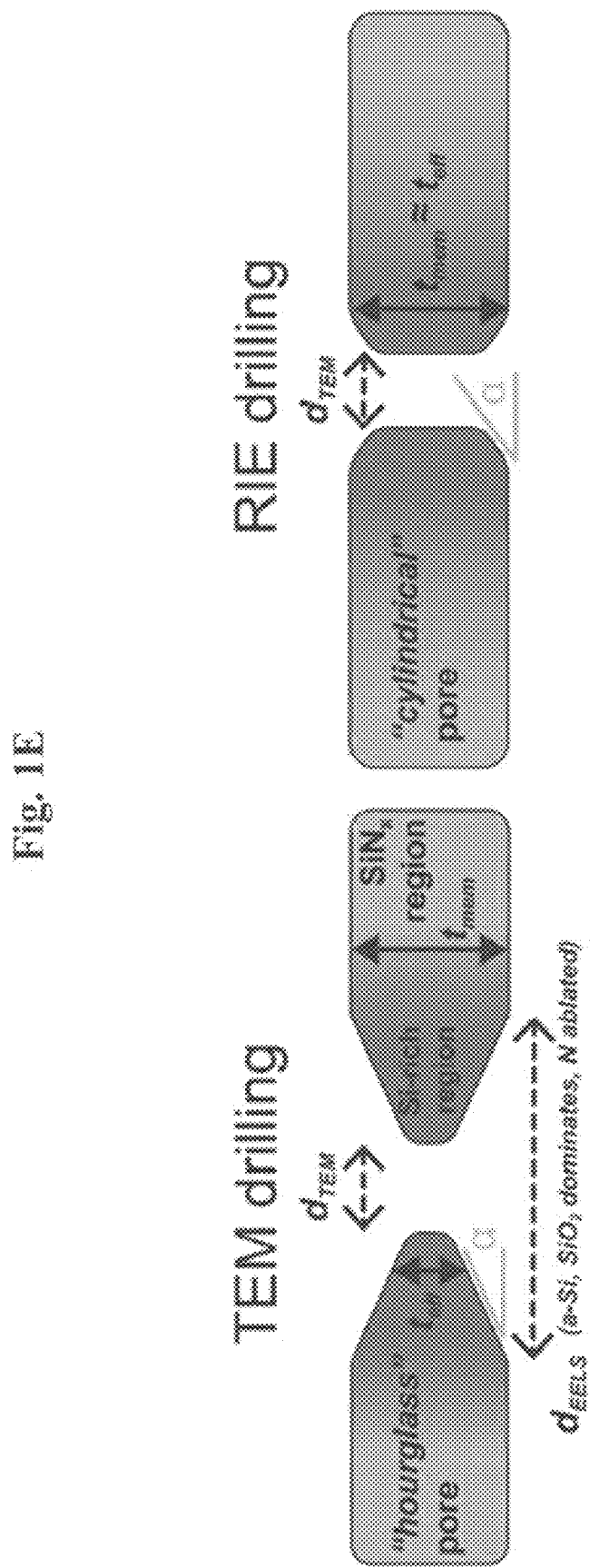

FIG. 1b shows the optical image of a suspended $SiN_x$ window where pores are fabricated. Example TEM images are shown of a single pore ($d_{TEM}$~5 nm) in a $t_{mem}$=10 nm $SiN_x$ membrane (FIG. 1c), and a nanopore array ($d_{TEM}$~55 nm) consisting of N~150,000 pores in a $t_{mem}$=100 nm $SiN_x$ membrane (FIG. 1d). The stoichiometry of these $SiN_x$ membranes was determined using EELS showing a ratio of Si:N~3:4 (x=1.3). The as-fabricated pore diameters ranged from ~2 to 80 nm for single nanopores and ~50 to 60 nm for nanopore arrays. Two common models of pore structure are shown in FIG. 1e. these variations are caused by the nature of fabrication process, which will be later discussed and confirmed by EELS.

While it has been observed among experimentalists that thin nanopores can expand over continuous usage and/or repeated operating conditions (e.g. high voltage and high concentration salt solution for DNA translocations), to the best of our knowledge, we are not aware of any systematic study to quantify these changes.

Definitions of Diameter and Thickness

We define the membrane thickness, $t_{mem}$, measured by ellipsometry after fabrication. We also define the nanopore thickness as "effective thickness", $t_{eff}$, in conjunction with the TEM-measured diameter, to match the measured conductance value from a simple conductance equation, Eq. 1. For approximately cylindrical pores, $t_{eff}=t_{mem}$, as shown in FIG. 1e. For hourglass-shaped pores, $t_{eff}=\frac{1}{3} t_{mem} < t_{mem}$ fit well to the measured ionic conductance of TEM-drilled $SiN_x$ pores. The hourglass-shaped pore structure, in which $t_{eff}=\frac{1}{3} t_{mem} < t_{mem}$, was confirmed by TEM tomography and is also consistent with measured conductance through TEM-drilled pores.

We define two diameters, $d_{TEM}$, measured from TEM images, a top-down view onto the nanopore; $d_{TEM}$ is the diameter corresponding to the smallest constriction within the pore. The error in $d_{TEM}$ is +0.1 nm. The other, $d_{calc}$, is the pore diameter calculated from ionic conductance assuming an effective thickness, $t_{eff}$. We note that both approaches serve as good, but not ideal, estimates of the nanopore diameter and both have corresponding sources of errors and limitations. The value of $d_{TEM}$ corresponds to the pore size when it is in vacuum; the pore can change in size or close over time after exposure to air and ionic solutions. The calculated diameter, on the other hand, represents a more relevant estimation at the time of the ionic measurements, but its value (from Eq. 2) depends on the assumed value of the pore thickness.

Ionic Measurements on Single-Pore Chips with TEM Pores

To prepare nanopores for ionic measurements, both single nanopores and nanopore arrays are cleaned with boiling piranha solution, which removes organic contaminants from the $SiN_x$ surface and aids in pore wetting (FIG. 1a). Etch rates of piranha for silicon and silicon nitride for micromachining processing are typically listed as 0 nm/min or "etch rate known to be slow or zero, but etch rate not measured." No additional piranha cleanings were performed throughout the measurements.

Long-term pore durability over days and weeks is characterized by their stable ionic conductance via two-terminal current-voltage measurements on single pores, and by subsequent TEM imaging of single pores and nanopore arrays. The conductance G for a nanopore with diameter d and effective thickness, $t_{eff}$, can be estimated from:

$$G = \frac{I}{V} = \sigma\left[\frac{4t_{eff}}{\pi d^2} + \frac{1}{d}\right]^{-1} = \frac{\sigma \pi d^2}{4t_{eff} + \pi d}, \quad (Eq.\ 1)$$

where $I$ is the measured ionic current, V is the applied voltage, and σ is the ionic solution conductivity. Current-voltage (I-V) curves were measured in the control 1M KCl (pH 8.0, with measured σ=11.1 S/m.) Every few (2-5) days, the pores were rinsed in DI water to remove residue from the storage solution and then dried with nitrogen gas before measuring their conductance in the control 1M KCl solution. The conductance measurements lasted less than 30 min over which time the pore conductance was constant, and from which the updated nanopore diameter values were calculated from:

$$d_{calc} = \frac{G}{2\sigma}\left(1 + \sqrt{1 + \frac{16\sigma t_{eff}}{G\pi}}\right) \quad (Eq.\ 2)$$

It has been shown that high voltage pulses (up to +20 V) can form and expand nanopores in pristine $SiN_x$ membranes. We therefore limit the applied voltage to 0.1 V to minimize pore expansion due to voltage application and to isolate the effects of electrolyte solution on pore size and performance. By calculating diameters at later times, we obtain diameter etch rates, $\Delta d_{calc}/\Delta t$, from conductance.

Figure 2A:
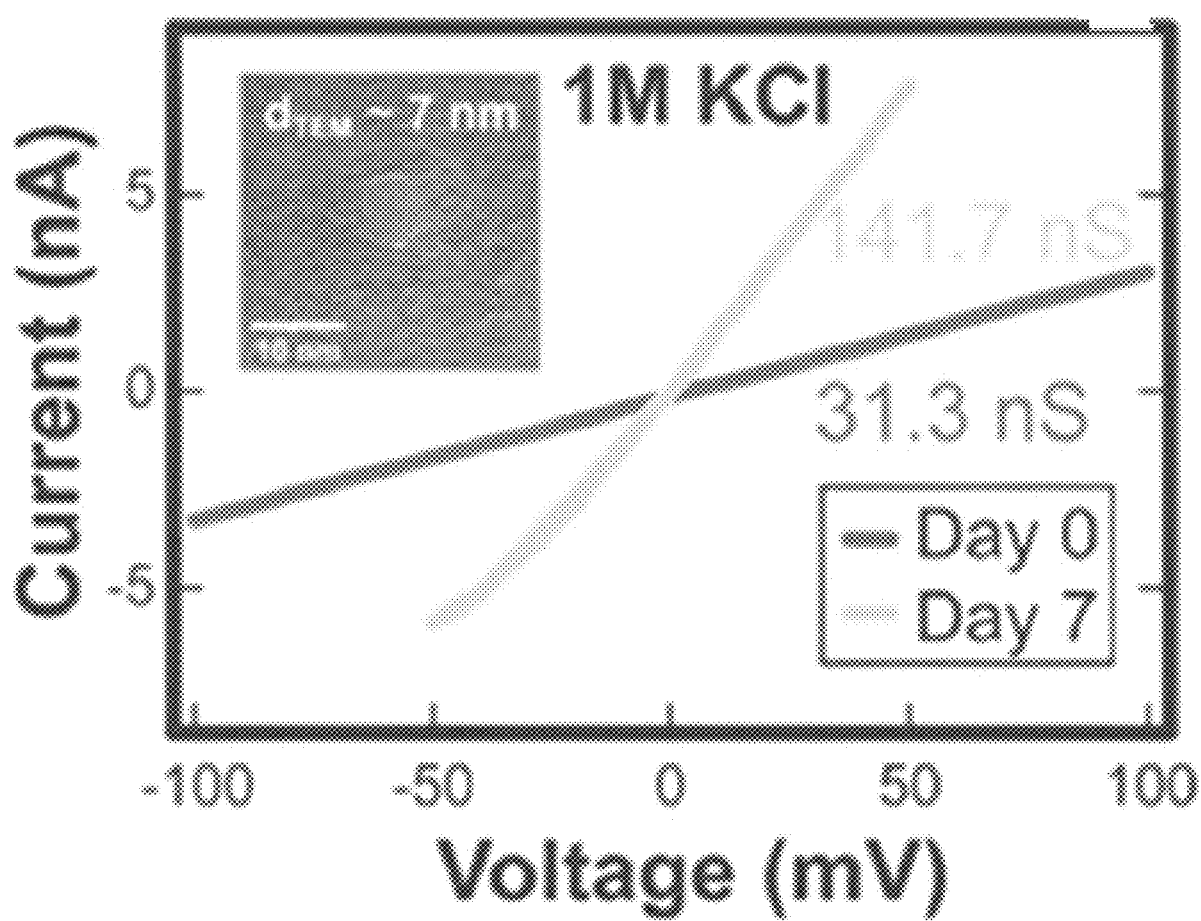
FIG. 2. Ionic conductance measurement data from eight TEM-drilled pores (total of 8 chips, each containing one pore). (a) Current-voltage curves for a single nanopore before and after storage in 1M KCl over a course of 7 days, inset shows the nanopore TEM image, with $d_{TEM}$~7 nm. Following measurement data are shown in (c). (b) G vs. time for one single nanopore is shown in three regions. The pore was stored first in (I) 0.1M KCl, then (II) ethanol/water (v/v=1/1), then back to (III) 0.1M KCl. This pore expanded from $d_{calc}$~3—5 nm (beginning of I) to $d_{calc}$~14-18 nm (end of region III). (c) G vs. time for a total of seven single nanopores. Six different pores are stored in 4 different concentration of KCl, 1M $MgCl_2$ and 1M LiCl. Conductance, G, is measured over a period of time. I-V measurement is performed in the control solution, 1M KCl, pH 8.0, σ=11.1 S/m. Inset shows a different pore, stored in ethanol/water, conductance remains stable over 40 days with (G)=5.6 nS and $d_{calc}$=2.6±0.1 nm. (d) (Top) Proposed geometric model assuming constant pore thickness, $t_{eff}$, and diameter etch rate, E. Given a fixed $t_{eff}$, a range of diameter etch rates (red dashed lines) are calculated to include the measured G (green squares) when the pore was stored in 1M KCl. (Bottom).

An ionic measurement of a single nanopore is shown in FIG. 2a. As shown in the inset TEM image, the initial pore diameter after drilling was $d_{TEM}$~7 nm. After storing in 1M KCl solution for 7 days, the measured conductance increased from 31.3 nS to 141.7 nS. Assuming $t_{eff}=t_{mem}=10$ nm, corresponding d calc increased from 7.6 nm to $d_{calc}$=20.6 nm. If we replace the effective thickness to $t_{eff}=\frac{1}{3} t_{mem}$, we obtain a slightly different calculated diameter increment, from $d_{calc}$=5.2 nm to 16.1 nm. Taking both $t_{eff}$ into account, we then acquire a range of rate, $\Delta d_{calc}/\Delta t=1.6$ to 1.9 nm/day. Following measurement data are shown in FIG. 2c.

Figure 2B:
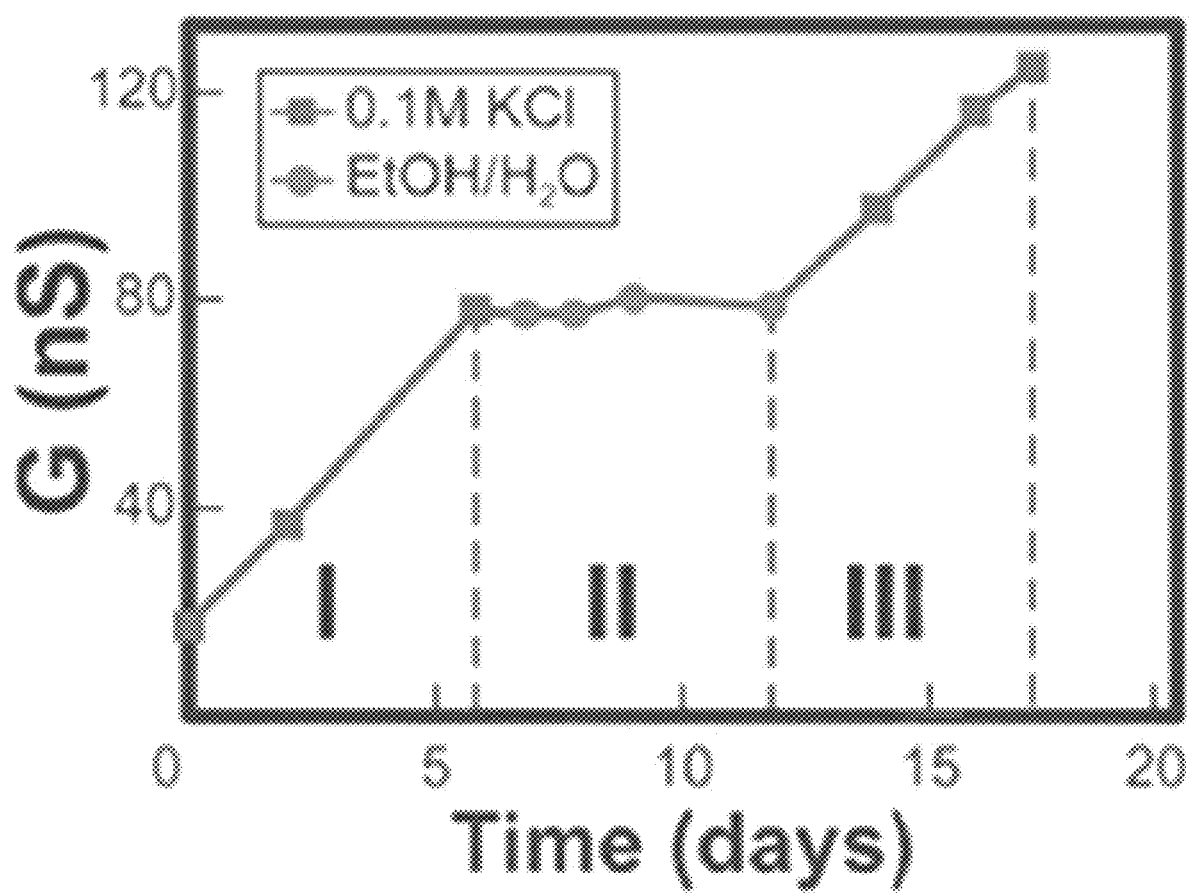
Figure 2C:
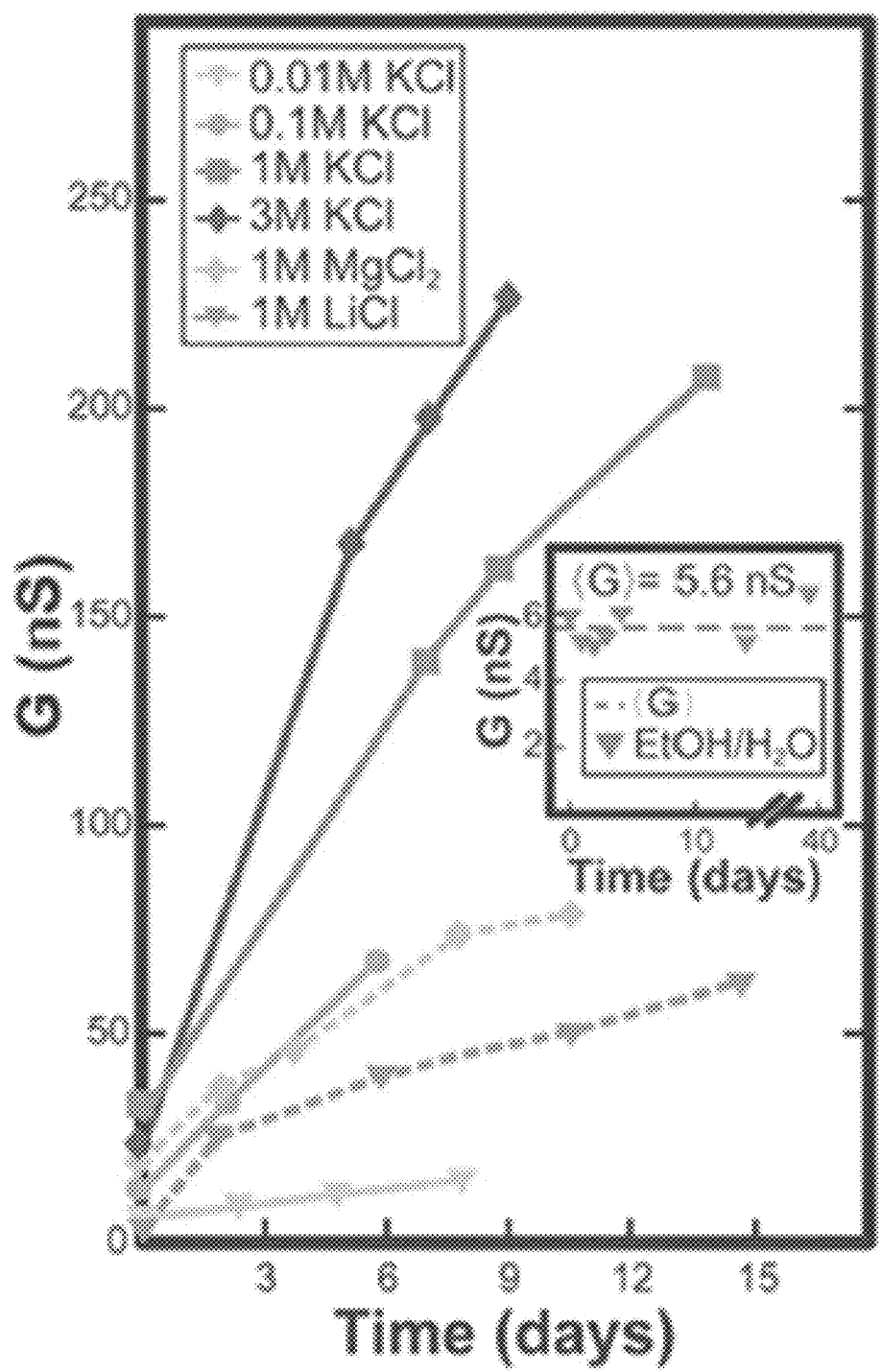

FIG. 2b shows ionic conductance measured in control 1 M KCl solution as a function of storage time (alternatingly stored in between 0.1 M KCl and ethanol/water) for another pore with an initial diameter $d_{TEM}$~3 nm and corresponding $d_{calc}$=3.5 nm (assuming $t_{eff}$~3 nm) and $d_{calc}$=5.3 nm (assuming $t_{eff}$=10 nm). $d_{calc}$ increased approximately linearly when the pore was stored for a week in 0.1 M KCl at an average rate, $<\varepsilon>_{T=7\ days}^{t_{eff}=3\ nm}=0.9\pm0.1$ nm/day and $<\varepsilon>_{T=7\ days}^{t_{eff}=10\ nm}=1.2\pm0.1$, respectively (regions I and III), while the conductance, and therefore pore diameter, remained constant when the pore was stored in ethanol/water for a week (region II).

We define $<\varepsilon>_T^{t_{eff}}=<\Delta d_{calc}/\Delta t>_T^{t_{eff}}$ as the time-averaged diameter change per unit time, i.e., the "average diameter etch rate" over time period T (in days); it was estimated as the average value of calculated diameter etch rates measured from consecutive ionic measurements on single pores. Consecutive ionic measurements were performed on single TEM-drilled pores at Day 0 (t=0) and then up to about Day 78 (for example, Days 1, 7, 9, 14). Individual diameter etch rates $\varepsilon_1$ to $\varepsilon_3$ are estimated from repeated conductance measurements on the same pore over time, relative to the initial I-V measurement on Day 0, as:

$$<\varepsilon>_T^{t_{eff}} = \left(\sum_{n=1}^{N-1}\varepsilon_n\right)/(N-1) = \frac{\sum_{n=1}^{N-1}\left(\frac{d_{calc,n} - d_{calc,o}}{t_n - t_o}\right)}{N-1}, \quad (Eq.\ 3)$$

where $d_{calc,n}-d_{calc,o}$ is the calculated diameter change during the time period $t_n-t_o$, $t_{eff}$ is the assumed effective pore thickness, and N is the total number of ionic I-V measurements (N=4, 5), yielding N−1 rates, $\varepsilon_1$ to $\varepsilon_{N-1}$. Here, $d_{calc,o}$ is the diameter calculated from the initial conductance value at t=0. I-V measurements were performed for up to T=15 days for most pores (FIG. 2c) and up to T=78 days (inset of FIG. 2d). Error for diameter etch rates are quoted as the deviations from mean values. We quote average diameter etch rates but note that the slope of G vs. time decreases in time. We later discuss and model this slowdown of etching at long times.

FIG. 2c shows the same measurements of conductance vs. storage time for six additional different single-pore chips with initial diameters, $d_{calc}$, in the range of ~2 to 8 nm (assuming $t_{eff}=10$ nm). Data are shown for four different concentrations of KCl solution (0.01 M, 0.1 M, 1 M and 3 M), 1 M solutions of LiCl and $MgCl_2$, and (inset) ethanol/water. From measurements on single pores we observe five main characteristics of this etching process:

Conductance Increased Over Time in Salt Solutions.

The pore expands due to interactions between the salt solution and pore wall.

Conductance Increased More Rapidly for Higher Concentrations of KCl

This phenomenon can be explained by a gradual pore wall etching by the salt solution which proceeds faster in more concentrated solutions. It is important to observe that this happens even without external stimulation, e.g. voltage or laser light. From data in FIG. 2c, we extract average diameter etch rates, of $<\varepsilon>_T^{t_{eff}=10\ nm}=0.21\pm0.01$, 1.2±0.1, 1.7±0.2 and 2.9±0.3 nm/day for 0.01M, 0.1M, 1M and 3M KCl solution, respectively. These average rates correspond to the expansions of four different individual pores, soaked in solutions with four different KCl concentrations, and the errors quoted above are the deviation from the mean of diameter etch rates from 3 to 5 consecutive measurements on a single pore over time (up to 15 days).

Conductance Increased Slower in LiCl and MgCl$_2$ than in KCl

For example, from the data for two pores plotted in FIG. 2c, we see that pore diameter also increased in 1M LiCl and 1M MgCl$_2$, at rates of $<\varepsilon>_T^{t_{eff}=10\ nm}=1.3\pm0.6$ and $0.8\pm0.2$ nm/day, respectively, about two times slower than in 1M KCl. The varying diameter etch rates between 1M salt solutions of KCl, LiCl and MgCl$_2$ could result from the differences in the activity of the electrolyte ions in aqueous solutions, indicated by the value of the activity coefficient, γ. The activity coefficient for a specific ion is known to depend on and differ from its counterion in a single electrolyte solution. Anionic activity coefficients, $\gamma_{Cl^-}^2$, for 1M KCl, LiCl and MgCl$_2$ at 298 K have been reported to be 0.664, 0.517 and 0.453, respectively. We empirically observe that the diameter etch rate is proportional to the square of the anionic activity coefficient, $\varepsilon \propto \gamma_{Cl^-}^2$:the ratio of diameter etch rates $\varepsilon_{KCl}:\varepsilon_{LiCl}:\varepsilon_{MgCl_2}=1:0.59:0.47$, is in excellent agreement with the corresponding ratios for $\gamma_{Cl^-}^2$, 1:0.61:0.47. For 1M and 3M KCl, the anionic activity coefficients, $\gamma_{Cl^-}$, are reported to be similar. However, our calculated diameter etch rates are about 1.7 and 2.9 nm/day, and indicate that for higher concentrations the diameter etch rate is higher. A similar trend was reported where a higher concentration KCl solution shortens the time needed to thin the membrane and form a pore.

Conductance Did not Change in Ethanol/Water Solution

For the two pores stored in ethanol/water solution, conductance remained stable. Inset of FIG. 2c illustrates this on one pore with (G)=5.6 nS and $d_{calc}=2.6\pm0.1$ nm, that was characterized for 40 days. Another example is in FIG. 2b (Region II).

We observe a decreasing rate of conductance increment in time, i.e., a decreasing first derivative, $\Delta G/\Delta t$.

The slope of G vs. t decreases in time for all the curves measured. This is most likely due to the change in structure (FIG. 2d) and chemistry (FIG. 3d) around the edge of the pore.

Practical Geometric Models for Conductance, G(t), Vs. Time

Figure 2D:
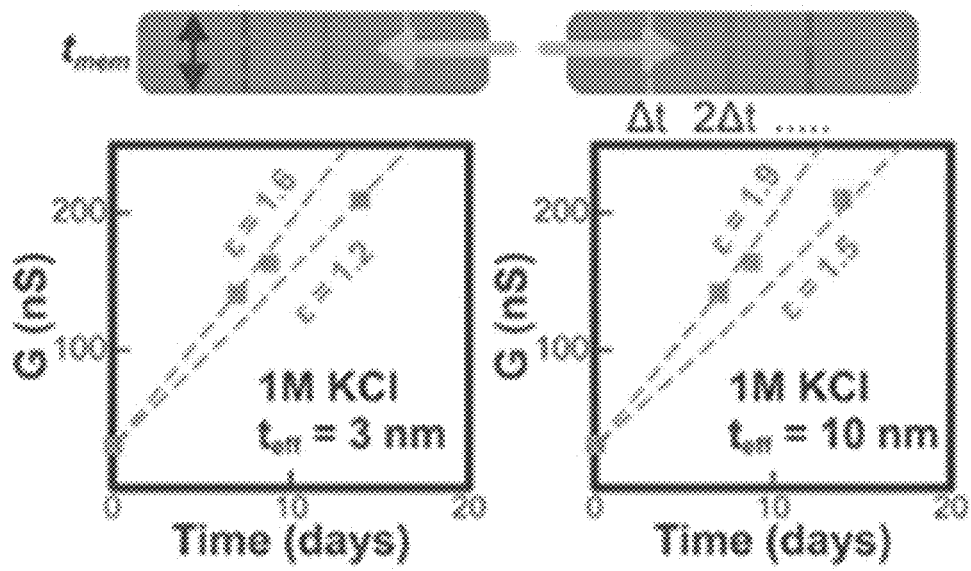
Figure 2D:
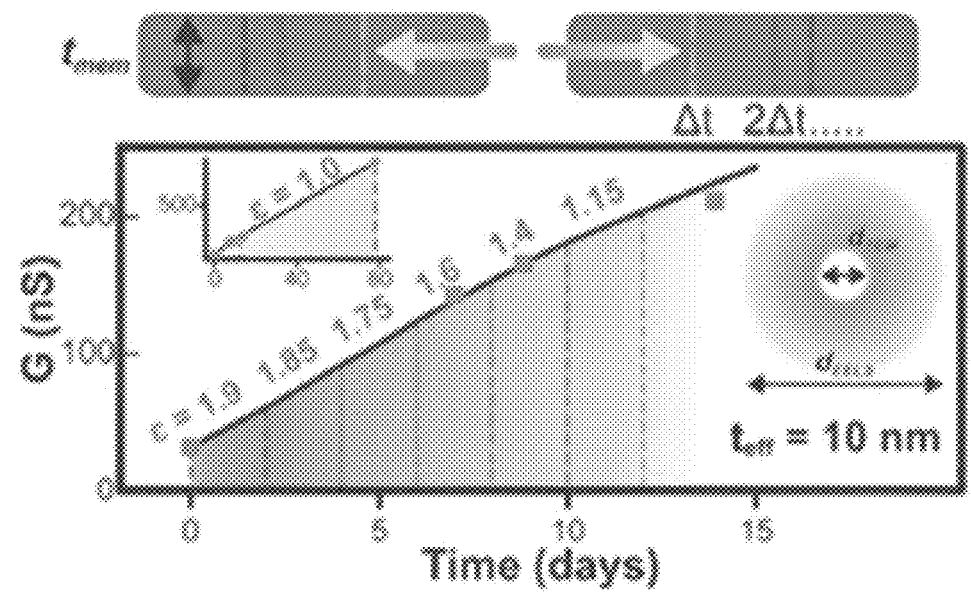

We present two useful geometrical models, illustrated in FIG. 2d, to view this process and to fit to the conductance data, G(t), in FIG. 2c.

Model 1: Constant Pore Thickness ($t_{eff}$=Const.) and Constant Diameter Etch Rate (ε=Const.)

Without precise thickness monitoring for the pore throughout measurement, a good first assumption is that the effective nanopore thickness, $t_{eff}$, falls between $t_{eff}=\frac{1}{3} t_{mem}\sim 3$ nm, and the full membrane thickness, $t_{eff}=t_{mem}=10$ nm, due to the hourglass shape of TEM-drilled pores. We therefore calculated the predicted conductance vs. time lines with the same starting G=31.3 nS as the pore stored in 1M KCl (FIG. 2a), but with different constant diameter etch rates <ε> ranging from 1.2 to 1.9 nm/day for $t_{eff}=3$ nm and 10 nm in FIG. 2d. G as a function of time is given by:

$$G(t) = \frac{\sigma \pi d^2}{4t_{eff} + \pi d} = \frac{\sigma \pi [(d_o + <\varepsilon> t)^2]}{4t_{eff} + \pi [d_o + <\varepsilon> t]^2} = \frac{\sigma}{\pi} \frac{f^2(t)}{B + f(t)} \quad \text{(Eq. 4)}$$

where $f(t)=n\ (d_o+<\varepsilon>t)^2$, $B=4\ t_{eff}$. The measured conductance values corresponding to 1M KCl fall in between lines for $t_{eff}=3$ nm and 10 nm with <ε>T=15 days~1.6 nm/day, which is similar to the previous calculation for the other pore in FIG. 2c.

Under these conditions and from a satisfactory match with the measured conductance over time, it seems reasonable to assume, as the simplest model, that the pore is expanding in diameter while its thickness remains roughly constant. To further directly study the changes in the thickness of suspended membranes, two 20-nm thick SiN$_x$ pristine chips without nanopores were immersed in 1M KCl for more than 7 and 25 days separately. We find that changes in thickness of these two pristine SiN$_x$ membranes are mostly negligible over time and less than 0.5 nm. The thickness was measured with a Filmetrics F40 interference system, both measurements show a goodness of fit of >94%, by comparing the recorded refractive index as a function of wavelength to the known database for Si$_3$N$_4$/SiO$_2$/Si thin film profile measurements. This result directly supports our estimations of diameter etch rate using a fixed initial thickness ($t_{eff}$=const.), and further indicates that the exposed SiN$_x$ around the pore edges plays a key role for the etching process.

Model 2: Constant Pore Thickness ($t_{eff}$=Const.) and Time-Dependent Diameter Etch Rate. ε(t).

The model of increasing pore diameter and constant pore thickness explains the overall magnitude of conductance increase but fails to explain the slowing down of the conductance increase in time, seen by the downward curving of G vs. time (in days) in FIG. 2c. Our observations can be explained by assuming a diameter etch rate, ε(t), that decreases in time and we obtain a better match with our data, compared to the constant ε model (Model 1). FIG. 2d shows such a fit to G(t) by allowing the diameter etch rate to gradually decrease from 1.9 nm/day to 1.15 nm/day over the first 12 days after immersion in 1 M KCl. Over longer periods of time (up to 2.5 months in 1 M KCl), we obtain a decreased diameter etch rate of ~1 nm/day as shown in the inset of FIG. 2d.

Finally, in addition to the changing diameter, we also note that the effective nanopore thickness could also be changing in the range ~3 nm to 10 nm. We tried several additional models and fits but obtain diameter etch rate values bound by Model 1 which already assumes two scenarios for pore thicknesses, 3 nm and 10 nm. More importantly, time-dependent pore thickness fits alone fail to explain the slowing down of the diameter etch rate in time and the shape of G vs. 1, and one needs to invoke a time-dependent at) (Model 2).

Figure 3A:
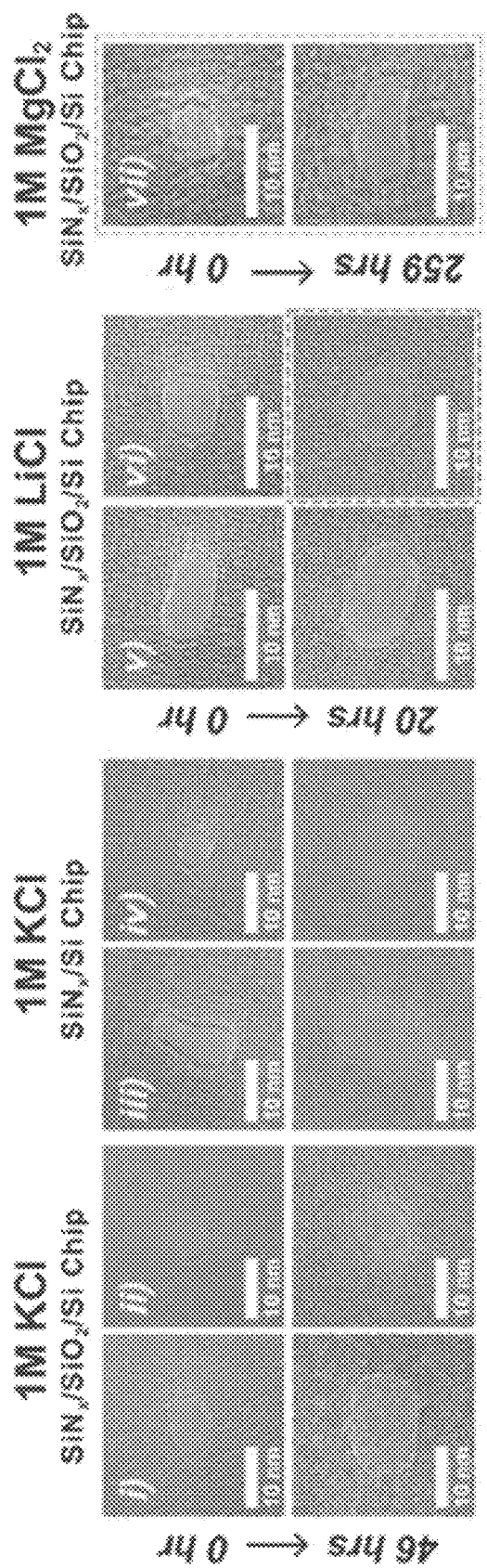

Diameter ($d_{TEM}$) estimation from TEM imaging and EELS analysis of TEM pores. In addition to conductance measurements, we used TEM imaging to characterize single pores before and after storage in ionic solutions (without conductance measurements). TEM images provide direct measurements of $d_{TEM}$ as a function of storage time and allow for calculations of diameter etch rate, $\Delta d_{TEM}/\Delta t$. FIG. 3a shows TEM images of 7 individual pores before and after storage in various 1M salt solutions. The images taken after salt solution exposure have been aligned to the same orientation before exposure to demonstrate any non-uniformities in the etching process. Pores drilled in TEM are typically round due to the circular nature of the electron probe. The presence of occasional astigmatism in the electron beam causes elliptical pores to form (for example, pores iii and v in FIG. 3a). In both cases, storage in salt solution leads to isotropic etching of the pore, allowing it to expand while approximately maintaining its original shape. This isotropic etching is consistent across different ionic solutions, such as KCl (pores i-iv), LiCl (pores v and vi), and MgCl$_2$ (pores vii). We note that the shape and composition of the thinned region at the pore edge strongly influences isotropic or anisotropic expansion of the pore (discussed later in FIG. 3d).

TEM images from pores i and ii (higher strain) and pores iii and iv (lower strain) in FIG. 3a also demonstrate that etching in salt solution occurs regardless of strain in the $SiN_x$ membrane. This is achieved by using two kinds of wafers, $SiN_x/Si$ and $SiN_x/SiO_2/Si$, where the middle, 5-μm-thick $SiO_2$ layer makes the membrane more curved and introduces more strain. Furthermore, we also tested a commercial 20-nm-thick $SiN_x$ membrane (without the middle $SiO_2$ layer in the chip), manufactured by SPI Supplies (See FIG. 9), to examine the etching effect from the salt solution and potentially from a heated environment. We indeed observed similar isotropic pore expansions in 1M KCl salt solution, demonstrating that etching effects are not unique to our membranes.

Pore vii in FIG. 3a is an instance in which we performed both ionic measurements (shown in FIG. 2c) and TEM imaging. From an initial diameter $d_{TEM}$=5.8 nm, the pore later expanded into an elliptical shape (13× 9.4 nm), with an effective diameter $d_{TEM}^{eff}$=11.1 nm, after being immersed for 11 days in 1M $MgCl_2$. We note that the identification and imaging of one small pore in the membrane without pre-fabricated markers on the surface presents many challenges. However, in this particular case, we had an inherent structural feature on the membrane surface that we could use as a guide. From the corresponding I-V measurements, we obtain a similar change of the diameter from $d_{calc}$=5.4 nm to 11.8 nm (see FIG. 8).

Figure 3B:
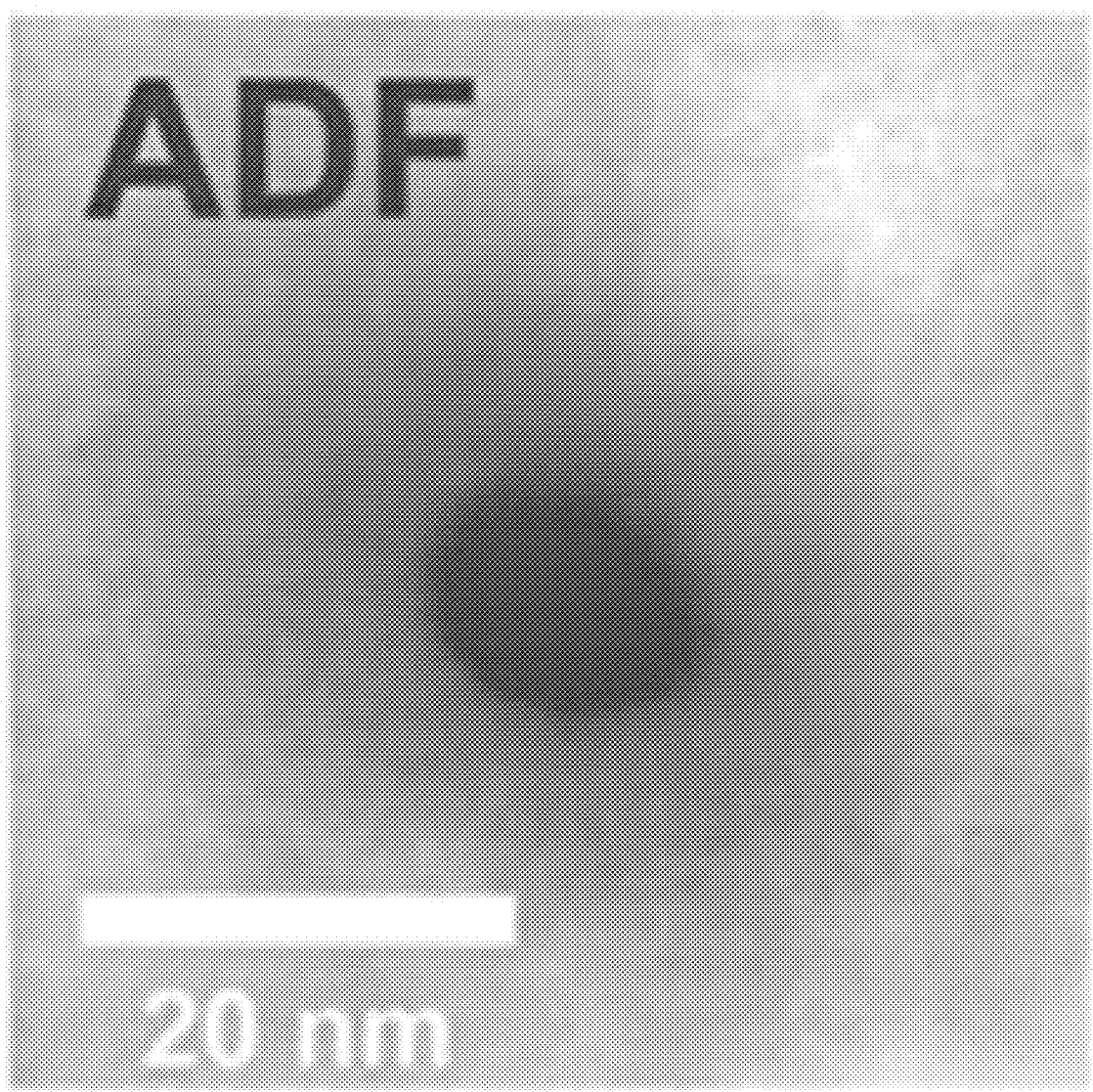
Figure 3C:
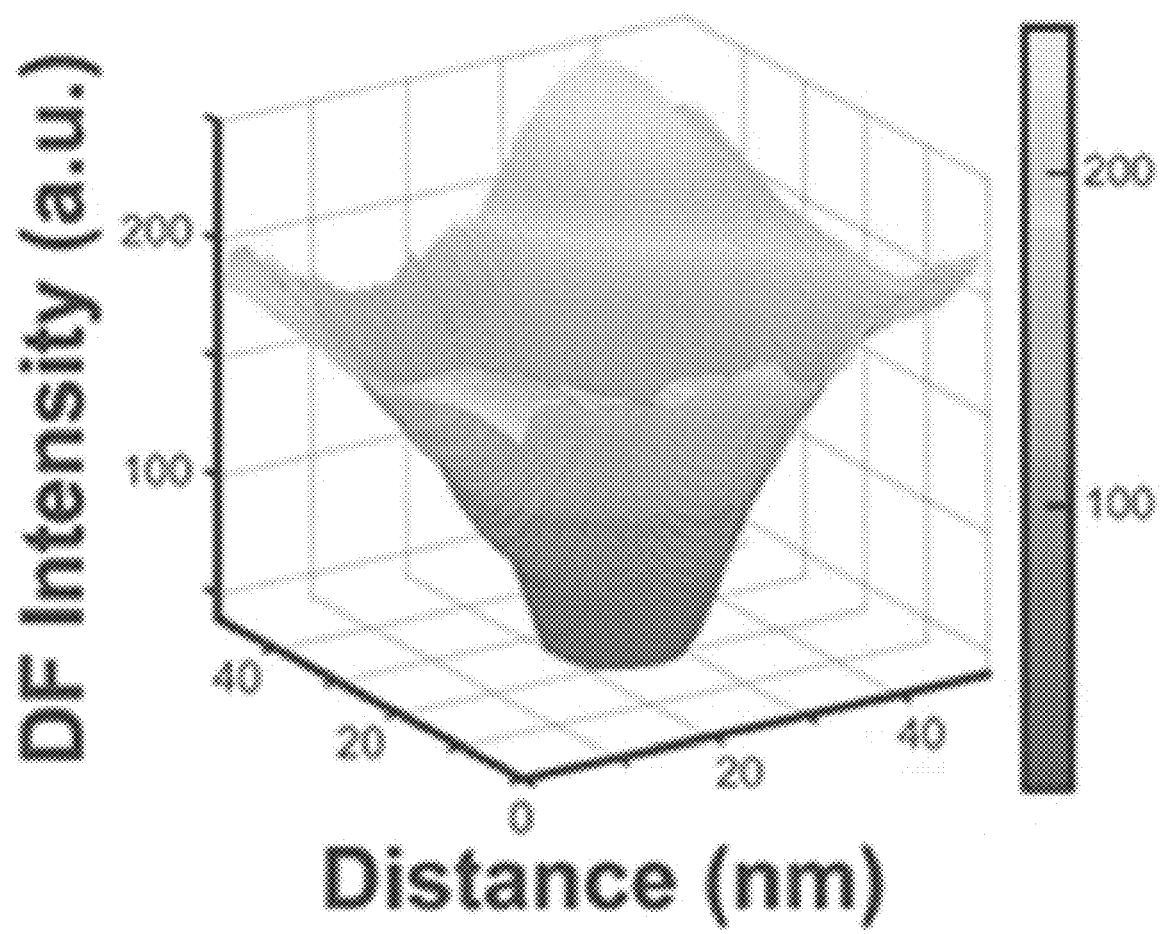
Figure 3D:
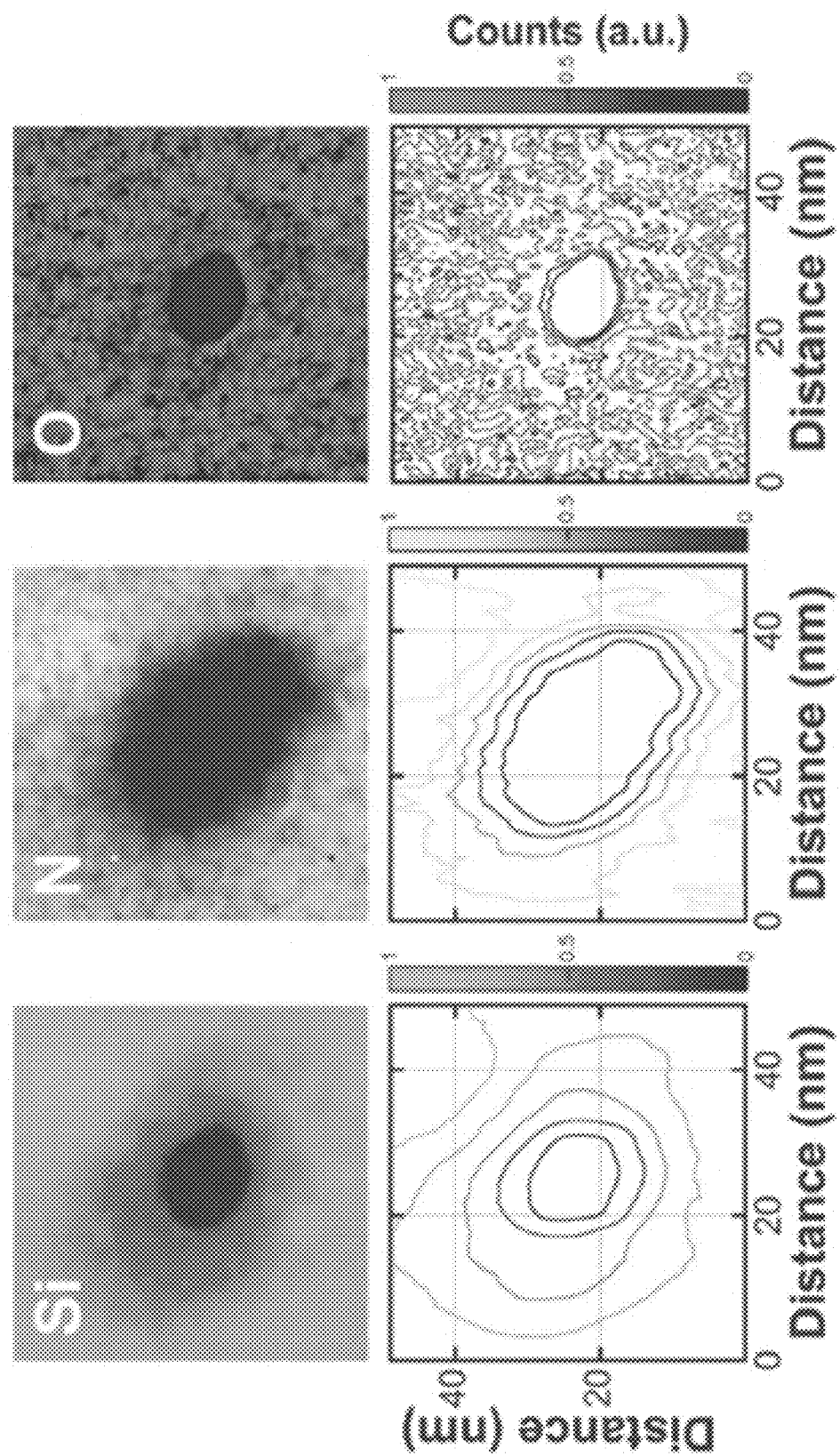

To determine the chemical composition of TEM pores and these adjacent thinned regions, we perform atomic resolution analytical and structural characterization using aberration-corrected TEM. With EELS 2D mapping of core-loss excitations, we are able to probe the underlying chemistry of $SiN_x$ pores. FIG. 3b is an annular dark field (ADF) image of pore vi from FIG. 3a after 20 hours of storage in 1M LiCl solution. Since ADF STEM images contain mass-contrast information from scattered electrons, the dark ring around the edge of the pore in FIG. 3b is indicative of a localized region that has been thinned. The appearance of this thinned area is most likely due to the Gaussian-like nature of the TEM beam, which causes the $SiN_x$ region around the pore to be exposed to electrons during TEM drilling, and is apparent in a 3D map of ADF image intensity (FIG. 3c). We note that the 3D maps in this work (FIGS. 3c, 4g, and 6b) are not directly indicative of pore shape, but rather their relative thickness as a function of spatial position. The first column in FIG. 3d shows an EELS map of the Si $L_{2,3}$ edge (green) for the pore in FIG. 3b and the corresponding 2D contour profiles as a function of electron counts. The Si signature is strong on the bulk $SiN_x$ membrane (i.e., far away from the pore) and gradually decreases in the irradiated thinned region up to the edge of the pore. Conversely, an EELS map of the N K edge (yellow) indicates that the thinned region is largely N-deficient compared to the $SiN_x$ membrane. This demonstrates that TEM beam exposure results in selective removal of N from the $SiN_x$ membrane and is consistent with previous reports. Some estimated a damage radius of ~75 nm in the TEM mode, which can be reduced in STEM mode. In our case, we observe an approximate 20 nm (see FIG. 7) to 30 nm diameter N-deficient region. Crucially, it also suggests that the etching process in TEM-drilled $SiN_x$ nanopores could be primarily driven by interactions between ionic solutions and the amorphous Si pore edge. A uniform signal of the O K edge (red) is seen across both the membrane and thinned region, which we attribute to the formation of a native oxide layer.

While there may be several chemical reactions responsible for pore expansion and etching, the effect of salt solution on silicon and silicon oxide has been studied in great detail previously, especially in the environmental context of various ocean minerals.

For example, silicon oxide is relatively water insoluble compared to other minerals and its concentration and slow release from silica minerals in sea water has been studied over a few decades. Upon dissolution of $SiO_2$ the following equilibrium is established: $SiO_2+2H_2O \leftrightarrow H_4SiO_4$. Additionally, other intermediate etching reactions with $Cl^-$ can take place such as in plasma etching of $SiO_2$. Some tried to explain their recent etching of $SiN_x$ membranes to form pores in salt solutions upon laser illumination. They hypothesized the formation of $SiCl_4$, where the Si—Cl bond in water is unstable and could be replaced by water molecules to form $SiO_2$ which is then dissolved at an increasing rate with increasing temperature. In another recent experiment, others argued that etching of $SiN_x$ is accelerated for Si-rich membranes, and favor the interpretation involving dissolution of $SiO_2$ that is sped up in higher pH and at elevated temperature resulting from laser illumination. While these explanations are plausible, targeted experiments towards articulating specific chemical reactions and rates could be carried out in this specific context of nanopores. These previous works together with our study, point to dissolution of $SiO_2$ and the role of Si-rich regions in $SiN_x$ for pore etching, formation and structure instability.

Diameter ($d_{TEM}$) distribution from TEM imaging and EELS analysis of RIE pores. In contrast to single nanopores, nanopore arrays over micron length scales are easily identified in phase contrast TEM images. We therefore implemented TEM imaging as a direct and primary means to precisely quantify the time-dependent diameters of nanoporous $SiN_x$ arrays after storage in various solutions. Pore etching over time was also directly observed for large scale nanopore arrays.

Figure 4A:
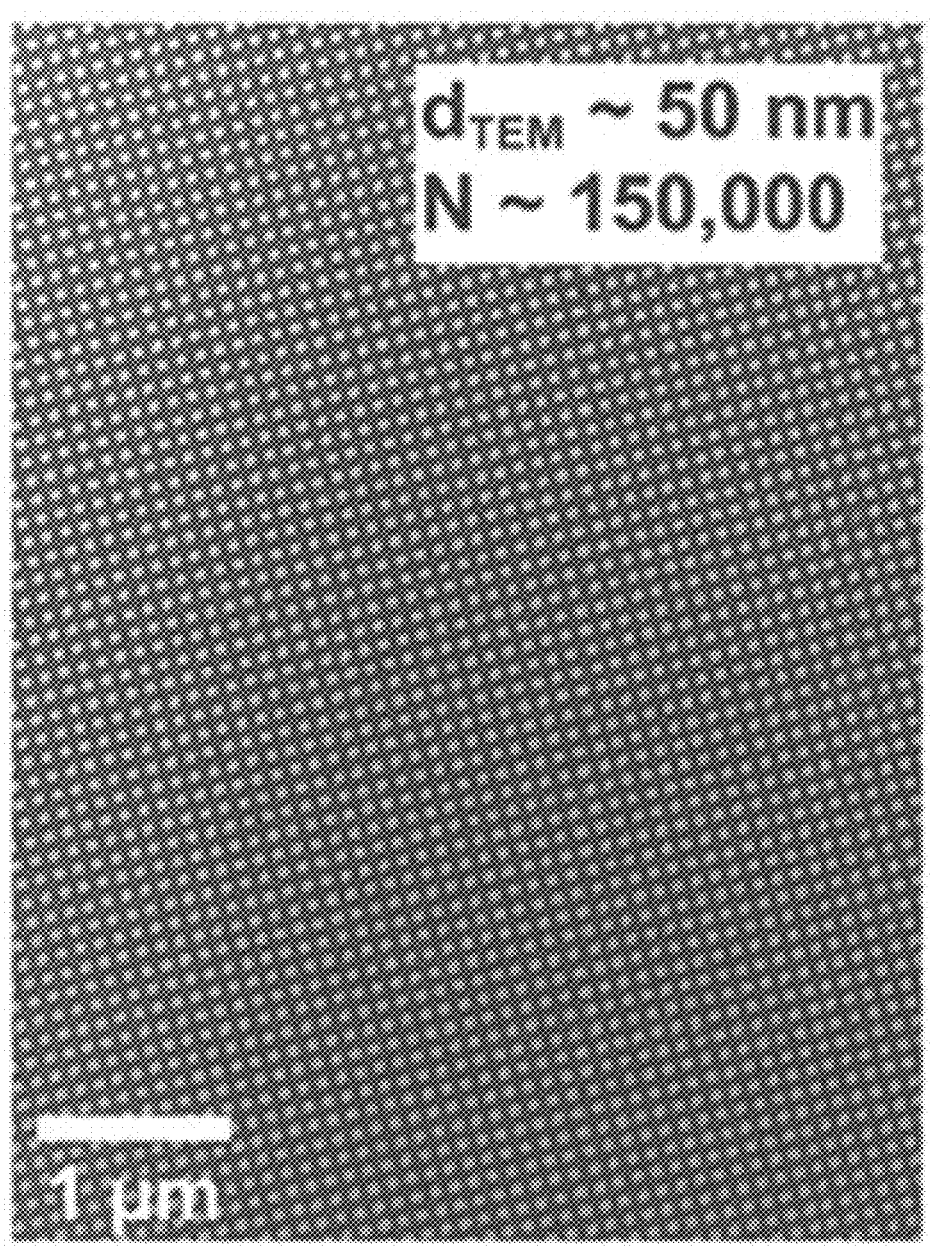
Figure 4B:
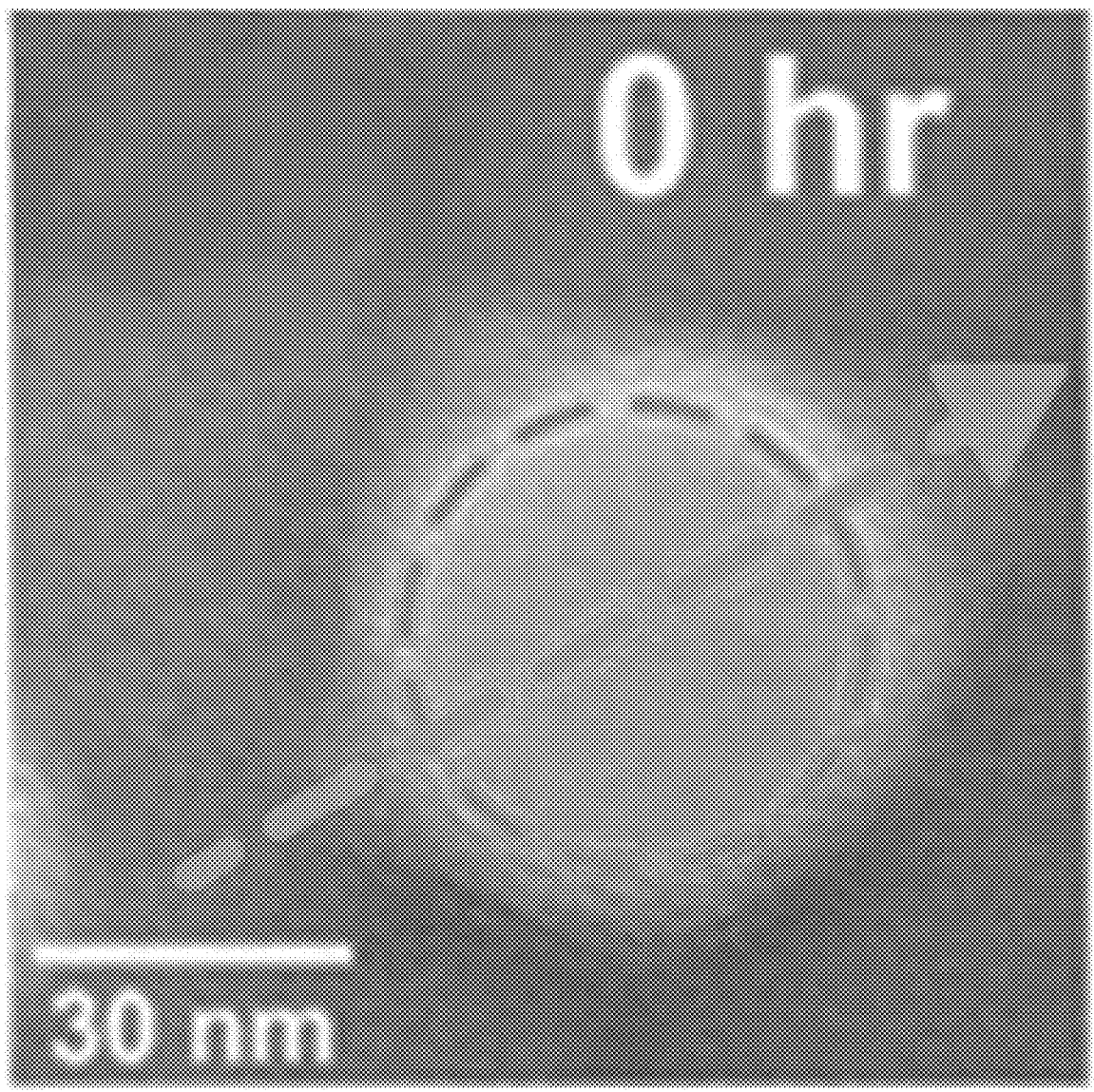
Figure 4C:
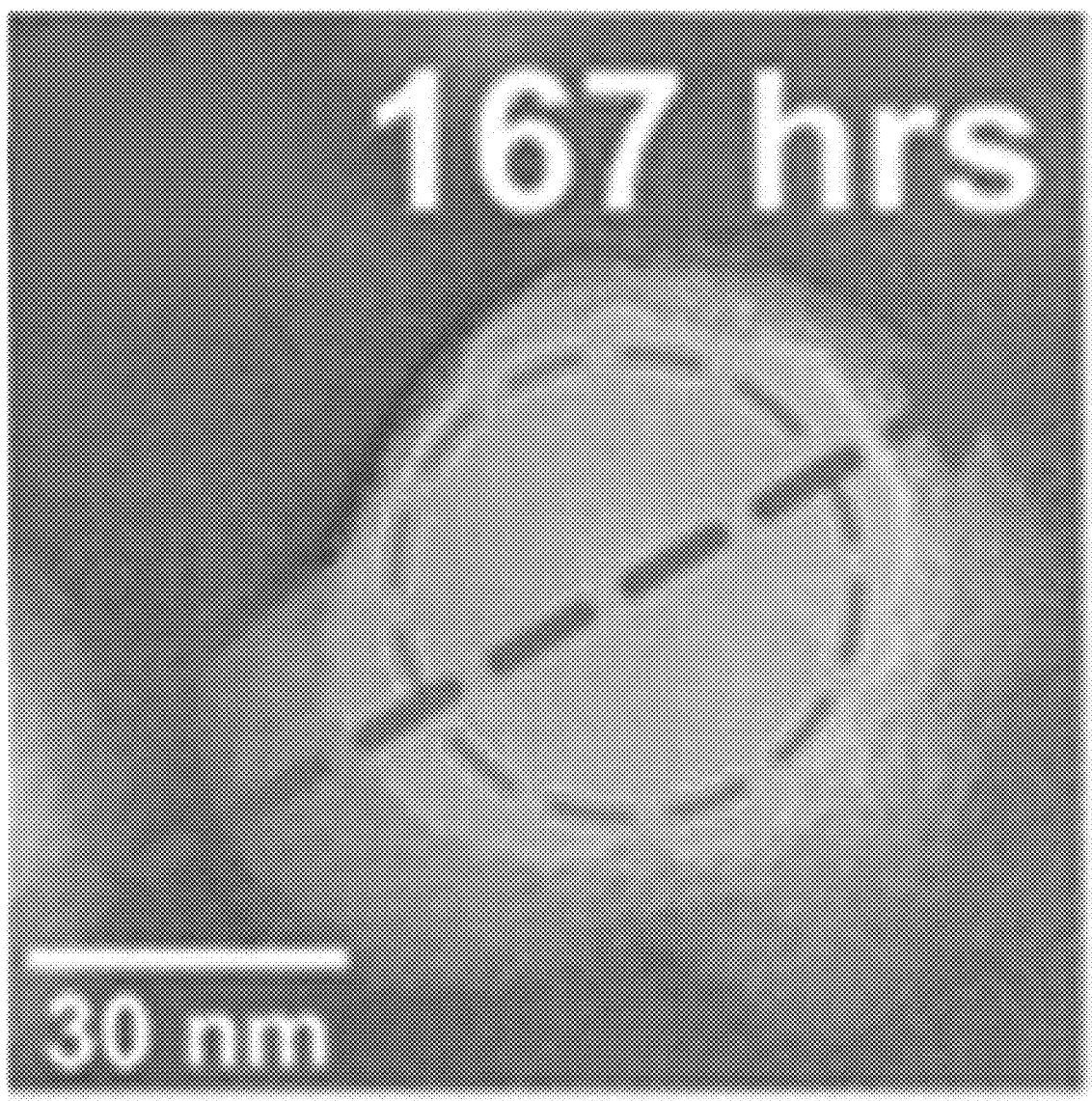
Figure 4D:
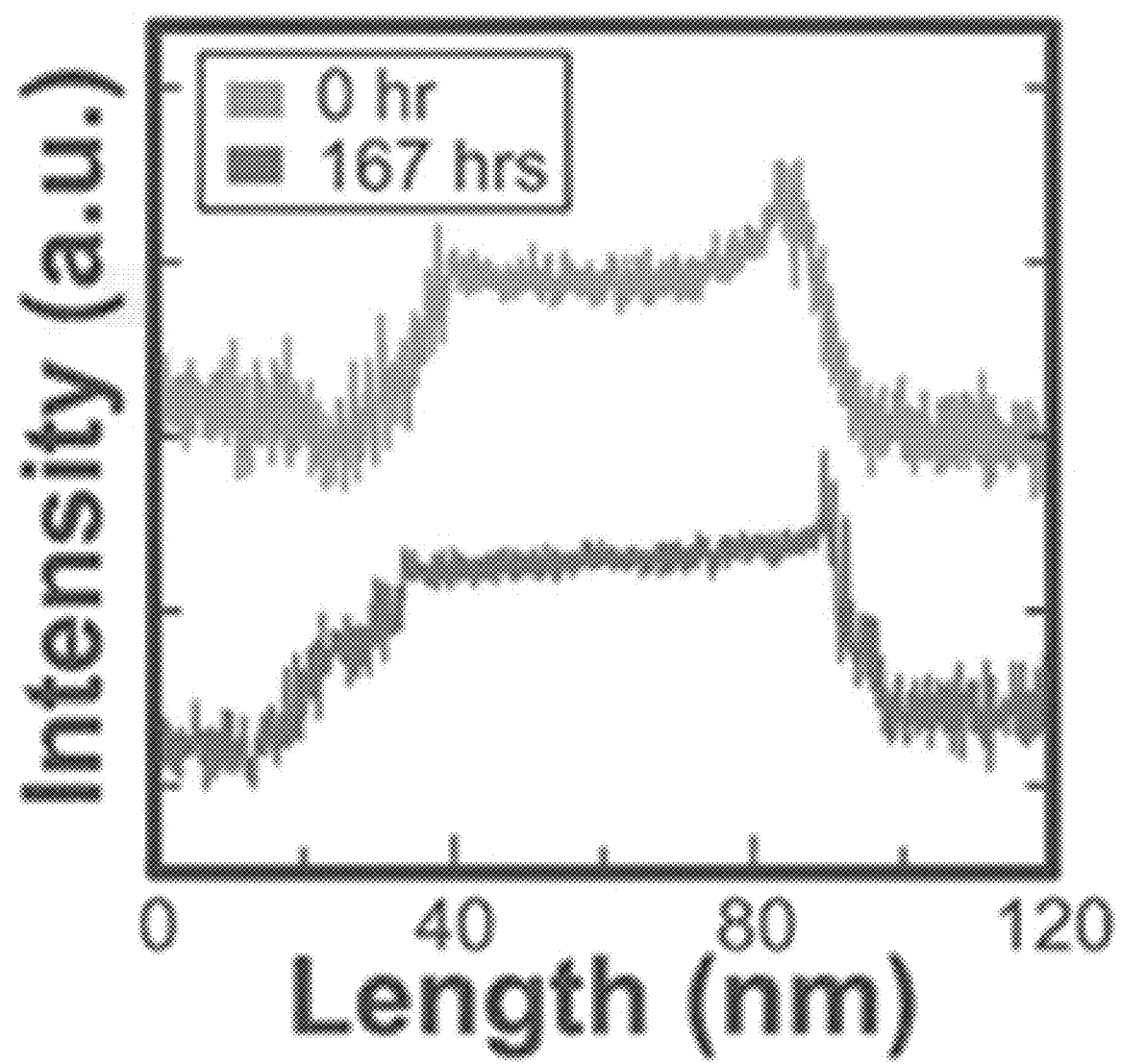

FIG. 4a is a TEM image of the as-fabricated array on a 100-nm thick $SiN_x$ membrane and FIGS. 4b and 4c are high-magnification TEM images of one pore within this array, which were acquired before and after storage for one week in 1M KCl solution. The red dashed circle outlines the edges of the initial pore after fabrication. FIG. 4d further shows the line scans of pores in these two images. These are two different, randomly chosen pores with diameters close to the mean diameter of the distribution. They are representative of the respective distributions and used to visually illustrate the mean pore expansion in the array over time. In these experiments we were not able to track individual nanopores, but rather quantify the overall distribution.

Figure 4E:
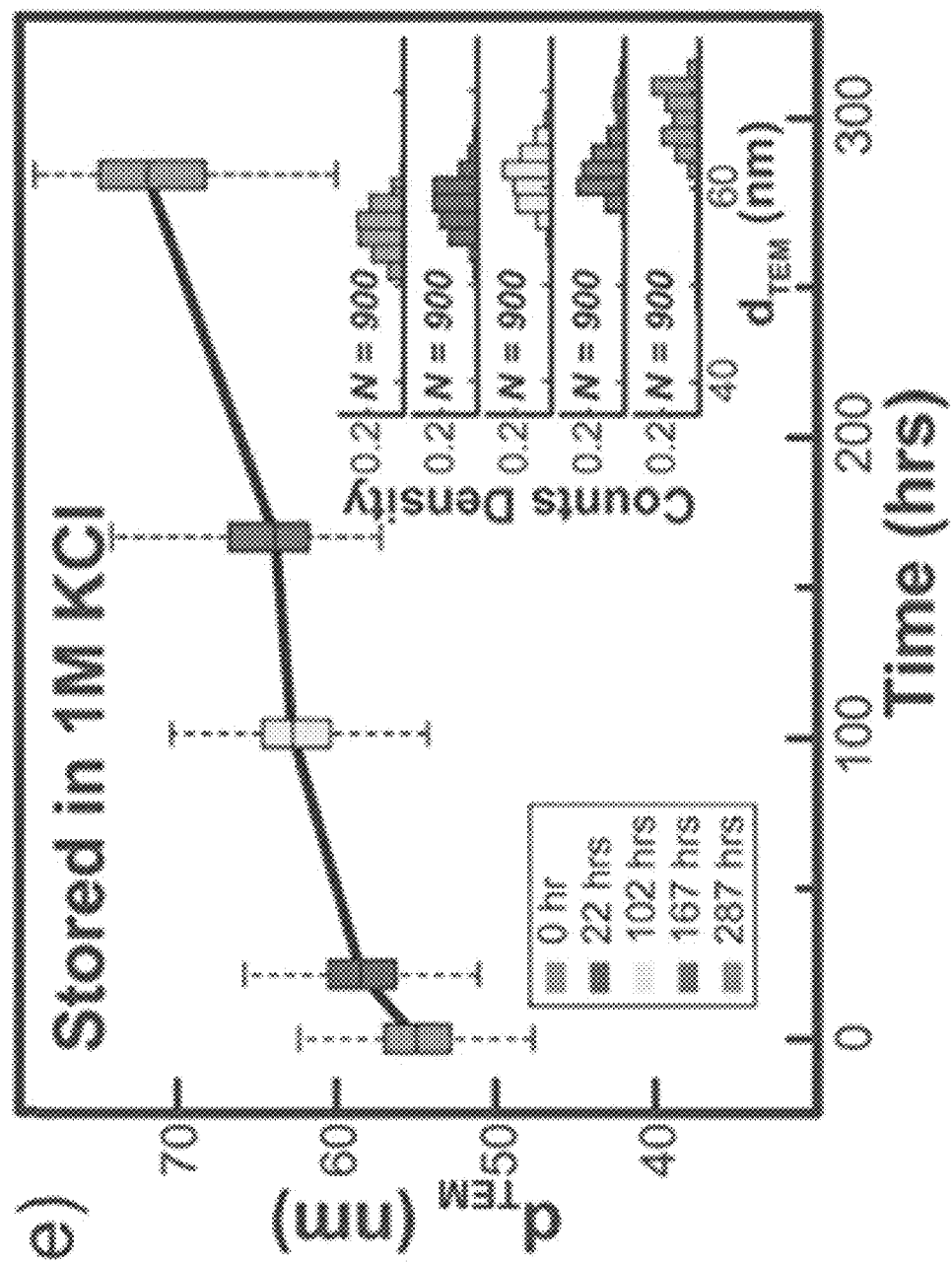

These visual observations from TEM imaging are statistically supported. TEM images were processed using ImageJ software from which distributions of pore diameters, $d_{TEM}$, were characterized (see Methods section). In FIG. 4e, we display the boxplot and histogram of all the TEM-measured nanopore diameters within one array and obtain the diameter etch rates from a randomly chosen subset of 900 pores on the chip. For each measurement, this subset of 900 pores was different but chosen within the same central area of the array. There is an inherent diameter spread across the $SiN_x$ window due to fabrication limits, caused by the dome-shaped membrane structure. We therefore confined our imaging to a 20 μm by 40 μm area of the membrane from the center (see FIG. 11), where the standard deviation of the diameter distribution is less than 1.7 nm. We verified that the increase of average pore diameters observed over time is due to the etching, rather than intrinsic diameter variations from fabrication and how we sampled nanopores over the membrane. The diameter distributions in the inset of FIG. 4e correspond to TEM images after the nanopore array was stored in 1M KCl during ~1, 4, 7 and 12 days. Each distribution was normalized to 1 by summing the total of 900 randomly chosen pores. From the initial ($d_{TEM}$~56 nm) and final average diameters ($d_{TEM}$~69.3 nm) after 287 hrs, we estimate a diameter etch rate $\Delta d_{TEM}/\Delta t=1.7\pm0.9$ nm/day, which agrees well with the value, $\langle\varepsilon\rangle_{T=15\ days}^{t_{eff}=10\ nm}=1.7\pm0.2$ nm/day, obtained from TEM-drilled nanopores via ionic measurements in FIG. 2c.

Figure 4F:
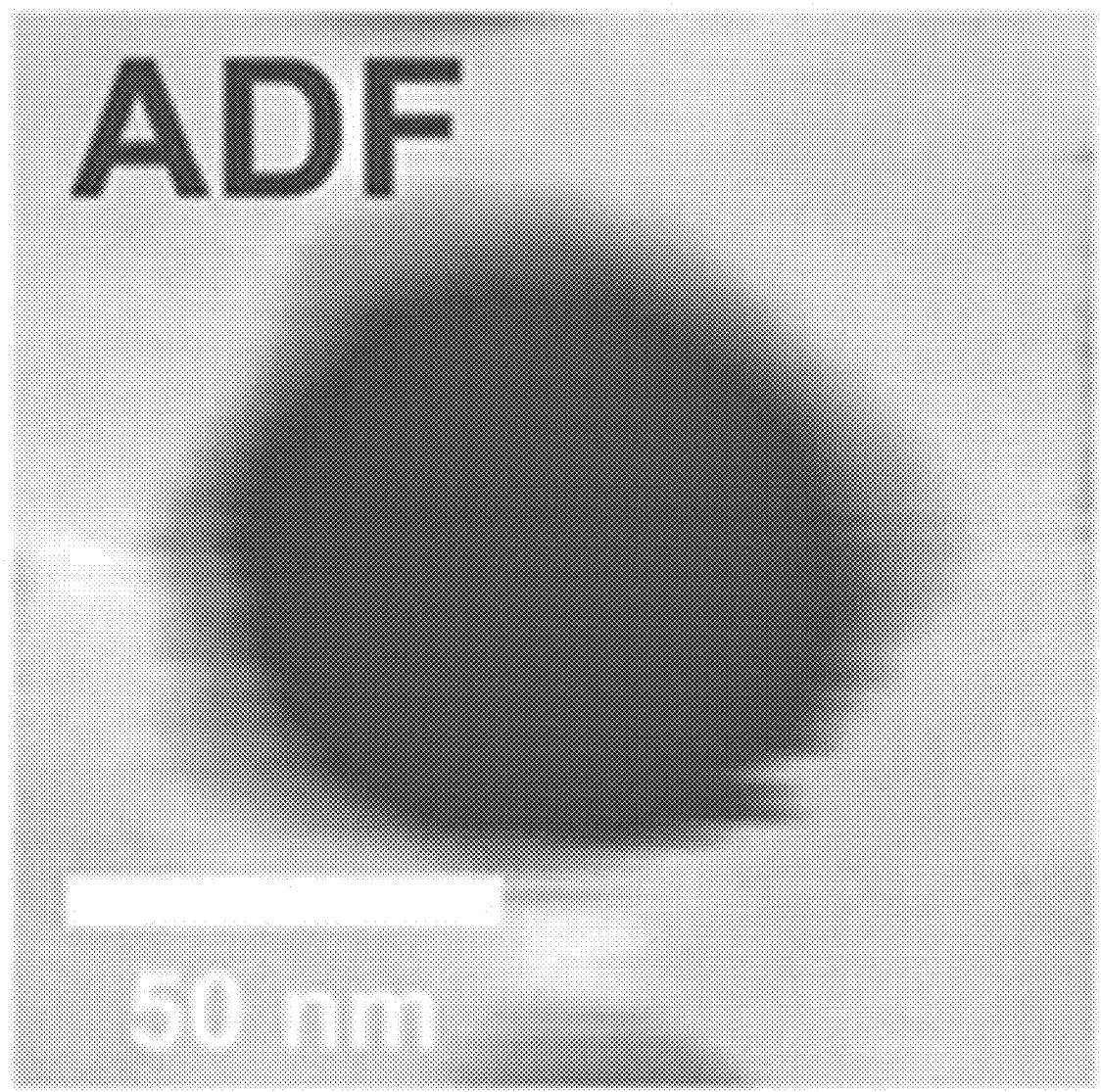
Figure 4G:
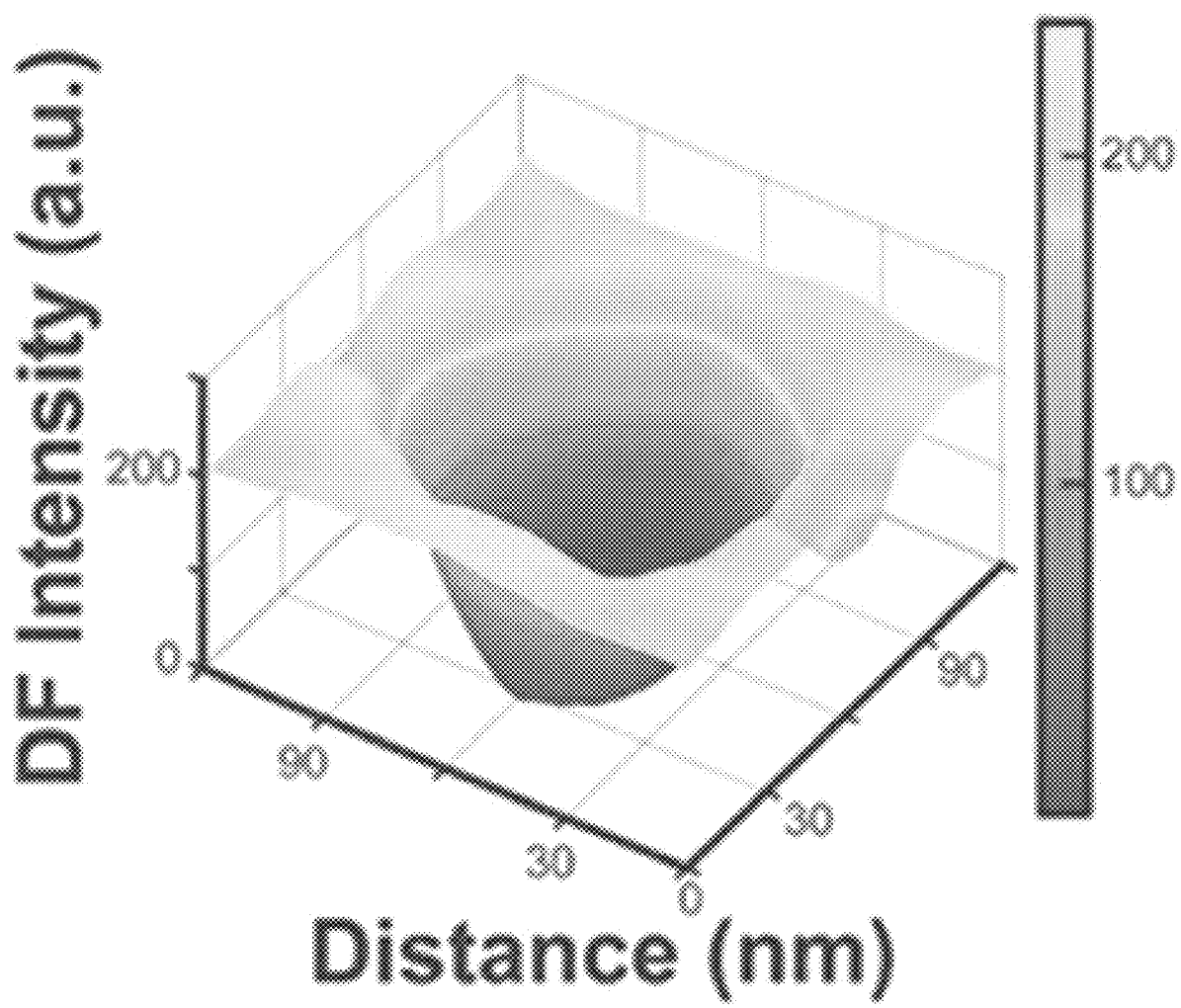
Figure 4H:
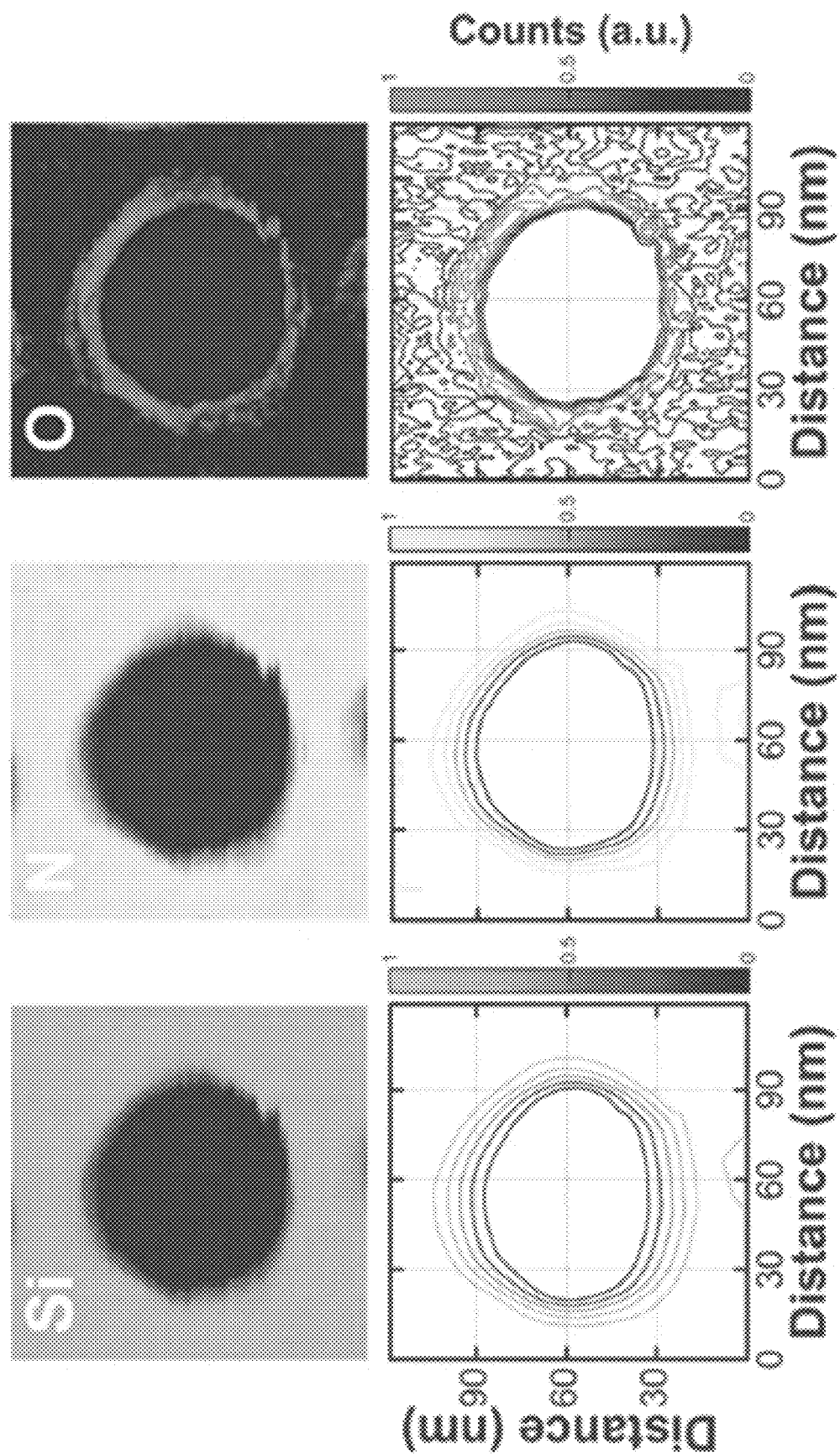

FIG. 4f is an annular dark field (ADF) image of one randomly chosen nanopore from the array in FIG. 4a after 167 hours of storage in 1M KCl solution. In contrast to TEM pores, FIGS. 4g and 4h indicate that nanopores fabricated via EBL and RIE have a more confined N-deficient region, since the photoresist provides a robust protection from unwanted electron beam exposure and RIE results in highly anisotropic etching nature. Similar to results in FIG. 3d, a uniform native oxide layer was observed across the membrane. This oxide also extends to the surface of the cylindrical pore wall (FIG. 4g), leading to a strong O K edge signature in the EELS map (FIG. 4h, red).

Observation of Pore Formation in Electron-Irradiated Membrane Areas in Salt Solution When an intact (non-porous) $SiN_x$ membrane region is exposed to electron irradiation, this region becomes $Si/SiO_2$ rich. This was previously shown by researchers who continuously exposed small, 50×50 nm², regions of the $SiN_x$ membrane to the electron beam in STEM mode, and recorded EELS signals over time as the membrane became gradually thinner. They monitored the Si and N signals and were able to deplete N completely, leaving a thin amorphous Si (a-Si) membrane behind. Corresponding molecular dynamics simulations showed that such membranes can be thermodynamically stable down to ~0.7-nm-thick, and a-Si membranes as thin as 1 to 2 nm were made in this way.

Figure 5A:
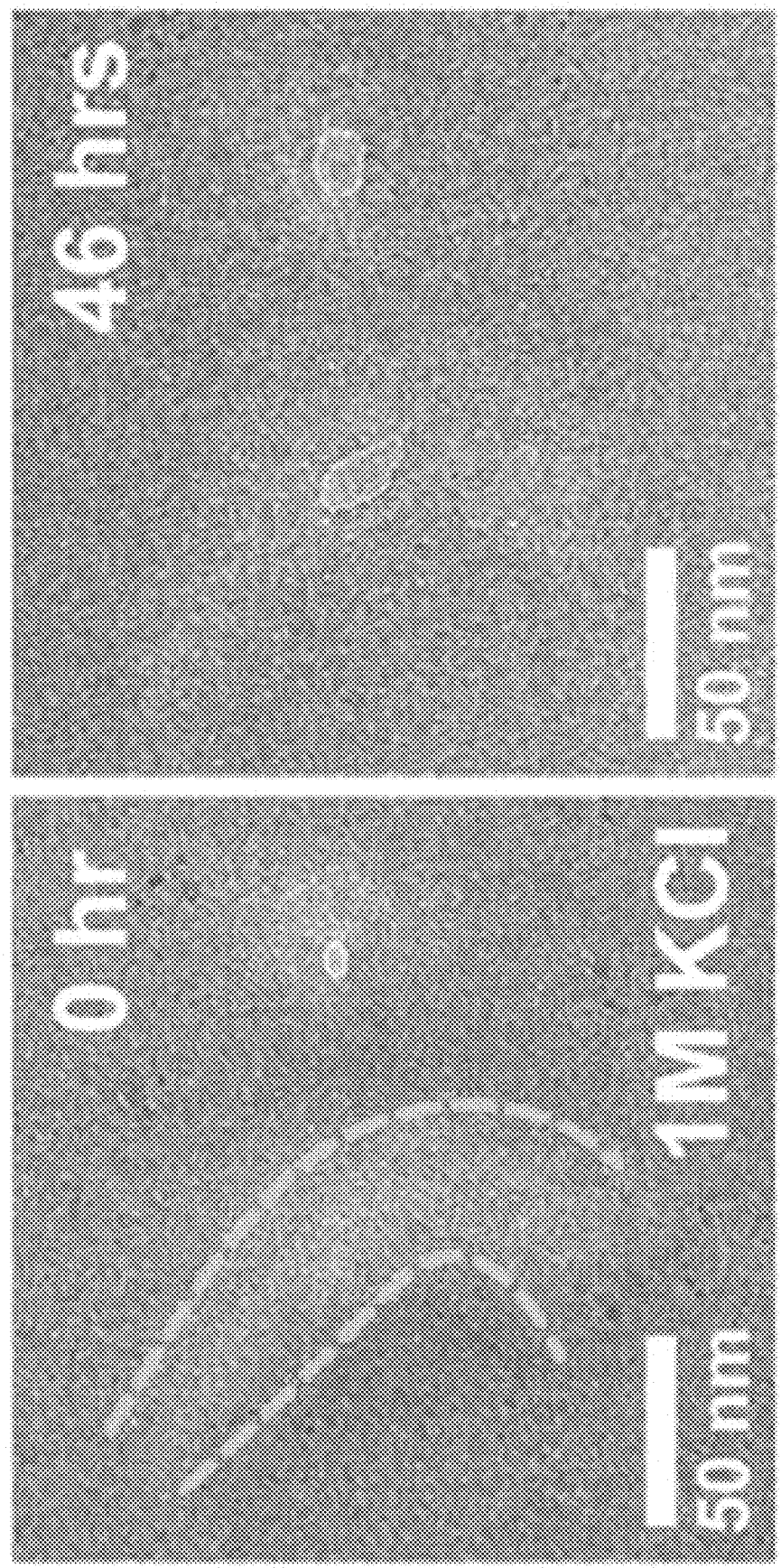

In our work, we further observe that an electron irradiated $SiN_x$ membrane region, which is Si-rich and N-deficient, slowly etches in salt solution over periods of hours and days, and the membrane thickness locally decreases. FIG. 5a shows a single nanopore forming in an electron irradiated $SiN_x$ region after about 2 days in 1 M KCl. The initial membrane here was $t_{mem}$=20 nm. The region outlined by green dashed lines shows where the beam irradiated a small area of this membrane. Next to the irradiated region, we also drilled a ~10-nm-diameter pore. After 46 hours in 1 M KCl, we imaged this region again and observed that a new pore emerged ($d_{TEM}$=11.8×23.0 nm), while the initial pore expanded as expected ($d_{TEM}$ increased from 10.4 to 13.8 nm).

Wet etching of selectively irradiated membranes can be a useful way to make pores, especially if it is not critical to have precise sizes and pore shapes like TEM fabrication allows. This empirical tweaking of experimental parameters resembles the "electroporation" or "membrane breaking" approach to make pores, where a relatively high voltage (~10 V) is used to break the membrane in salt solution in a few seconds or minutes, and where the salt type, concentration, pH, voltage magnitude and time are empirically tweaked for a desired effect.

Other recent reports of pore formation are variations on this theme, whereby additional optical and thermal excitation of the membrane was used to effectively thin it in salt solution. For example, laser illumination of 2D membranes in salt solution was found to create pores and expand them at a rate on the order of ~0.1 nm/second due to photo-oxidation of the material. One can think of this as "electroporation" aided by external parameters (such as presence of salt solution, temperature, illumination etc.), but at zero or small applied voltages, some reported pore formation due to localized $SiN_x$ heating while shining 532 nm laser light on a membrane in 4 M KCl along with a probing voltage of 0.01 V. Authors hypothesized that a photothermally-assisted etching process in solution results in pores equally thin (~1-3 nm) as electron-beam and RIE-thinned membranes. Others found that etching rates under laser illumination of amorphous $SiN_x$ membranes in salt solution can be attributed to photochemical reactions that are highly sensitive to the initial Si:N ratio in the membrane. This body of recent work, taken in totality with our EELS data and observations of slow etching at ambient conditions without any applied voltage, shows that etching occurs because of Si-rich regions, and helps establish a better mechanistic picture of $SiN_x$ pores and their behavior. In our case, membrane exposure to TEM and RIE increases the relative ratio of Si:N at nanopore edges and makes that region susceptible to faster etching by salt solution then the rest of it. One can vary $SiN_x$ stoichiometry and address pore formation and properties.

Surface Treatment and EELS Analysis of Hafnium-Oxide Coated Silicon Nitride Pores One advantage of $SiN_x$ pores for practical applications is that they show the highest signal-to-noise ratio for DNA measurements. Furthermore, silicon nitride membranes are easily manufacturable, well-studied, improved, and established in industry. It is therefore beneficial to seek alternatives to prevent the $SiN_x$ pore etching process and produce stable pores.

Figure 5B:
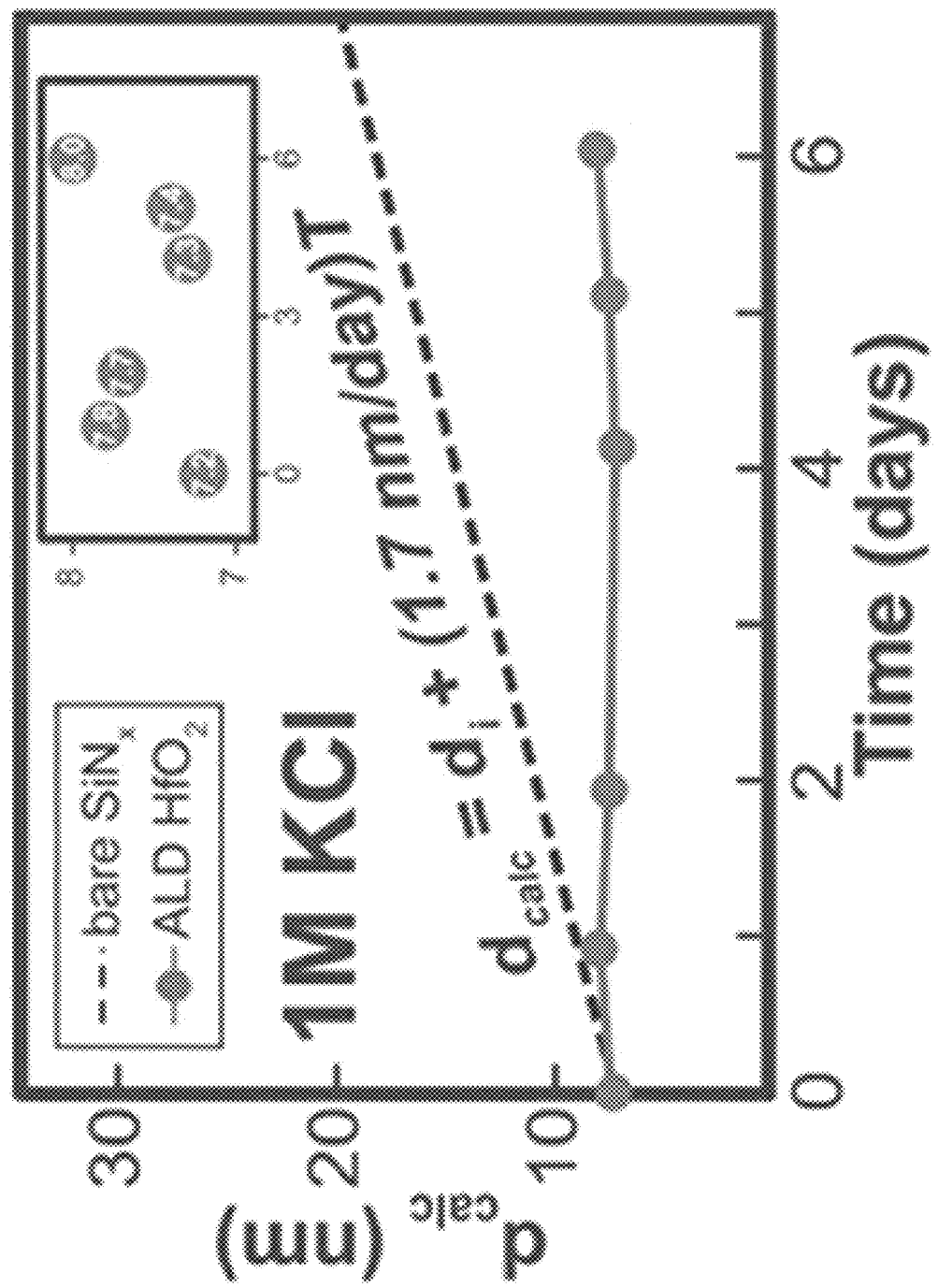

To this end, we have tested several surface modifications on the $SiN_x$ pores by coating them from both sides (cis and trans), including $Al_2O_3$ and Poly(ethylene glycol) (PEG). In brief, these coated pores still etched at similar or higher rates than the bare $SiN_x$ pores. However, we have discovered that when we coated the pores with a conformal 1-nm-thick layer of $HfO_2$ via atomic layer deposition, the coated pores remained stable in size in 1M KCl solution over days. This is consistent with recent observations reported by others, where a coating of $HfO_2$ inhibited pore expansion under laser illumination for 10 minutes at 60° C. In our measurements, a single nanopore was first drilled with $d_{TEM}$=3.6 nm, cleaned with a 10-minute piranha treatment, and then coated with 1-nm thick $HfO_2$, resulting in a total thickness of $t_{eff}$=12 nm. During the five acquired data points over the course of 6 days, the measured conductance fluctuated slightly in between 31.5±2.7 nS, corresponding to $d_{calc}$=7.6±0.4 nm, which remained virtually unchanged. In FIG. 5b, a flat d calc vs. time trend is shown, from which we extract a diameter etch rate of essentially zero, $\langle\varepsilon\rangle_{T=6\ days}$=0.4±0.3 nm/day, calculated from Eq. 1, for $t_{eff}$=12 nm. Note that this rate is calculated relative to the initial diameter, $d_{calc}$(t=0)=7.2 nm, and fails to reflect diameter increase and decrease between consecutive measurements (inset of FIG. 5b); if we averaged over consecutive positive and negative diameter etch rates between successive measurements, the calculated rate would be 0.1±0.3 nm/day.

These results demonstrate a stark difference compared to the much faster etching ($\langle\varepsilon\rangle_{T=15\ days}^{t_{eff}=10\ nm}$=1.7±0.2 nm/day from FIG. 2c) for bare $SiN_x$ pores under identical conditions. Dashed line in FIG. 5b indicates predicted $d_{calc}$ for 1M KCl. Thin $HfO_2$ coating therefore offers a practical solution towards prolonged nanopore lifetime and robust nanopore fabrication for biosensing operating purposes.

Assuming etching Model 1 (see FIG. 2d) we concluded from our experiments that an approximate, yet practical empirical equation can be used to predict the effective $SiN_x$ pore diameter, $d_{calc}$, after storage for time T (in days) in ionic solution:

$$d_{calc,final} = d_{calc,initial}(t=0) + \langle \varepsilon \rangle_T^T \quad \text{(Eq. 5),}$$

where $\langle \varepsilon \rangle$ is the time-averaged diameter etch rate in nm/day measured relative to the diameter at t=0 when the pore is immersed in salt solution, and $d_{calc,initial}$ and $d_{calc,final}$ are the initial (t=0) and final (t=T) diameters in nm. Table 1 summarizes all the time-averaged diameter etch rates over the indicated time periods, T, measured for different solutions, and the numbers of measurements (I-V and/or TEM) per sample. All results are for ambient conditions and pH 8.0. One can infer that these rates are likely to change for other parameters (pH, temperature, Si:N ratio in the membrane). Importantly, the calculated diameter etch rates are similar from both the ionic measurements and direct TEM imaging, providing an overall picture of etching and the range of the etching rates. The diameter etch rates for small ($d_{TEM}$<10 nm) and big ($d_{TEM}$>50 nm) pores are similar (for example, FIG. 3a and FIG. 4a), indicating that $\Delta d_{TEM}/\Delta t$ can be considered as approximately independent on the initial pore size.

FIG. 6 demonstrates the nanoscale effects of atomic layer deposition (ALD) on the structure and chemical composition of TEM-drilled pores. The annual dark field (ADF) image in FIG. 6a is a pore that was initially drilled in a 20-nm-thick $SiN_x$ membrane using TEM and then coated with 2.5 nm of $HfO_2$ via ALD. The 3D map of ADF intensity shown in FIG. 6b indicates that the ALD coating results in a localized increase in thickness around the pore edge. This is in stark contrast to the thinned regions surrounding non-ALD-coated pores (see FIGS. 3b and 3c). Core-loss EELS analysis reveals the differences in composition between the pore edge and bulk $SiN_x$ membrane. The blue EELS spectrum in FIG. 6c was acquired on the bulk $SiN_x$ membrane far (>100 nm) away from the pore. It exhibits the Si $L_{2,3}$, N K, and Si K edges at ~100, 400, and 1850 eV, respectively, expected for $SiN_x$. Also present are C K and O K edges at ~280 and 530 eV due to hydrocarbon contamination and native oxide formation, respectively. The Si and N edges are noticeably absent in EELS spectra acquired at the pore edge (yellow spectrum in FIG. 6c). The appearance of the O K edge at ~530 eV and Hf $M_4$ edge at ~1700 eV suggests that the ALD process causes $HfO_2$ deposition around the TEM-drilled pore, causing a reduction in diameter.

Figure 6A:
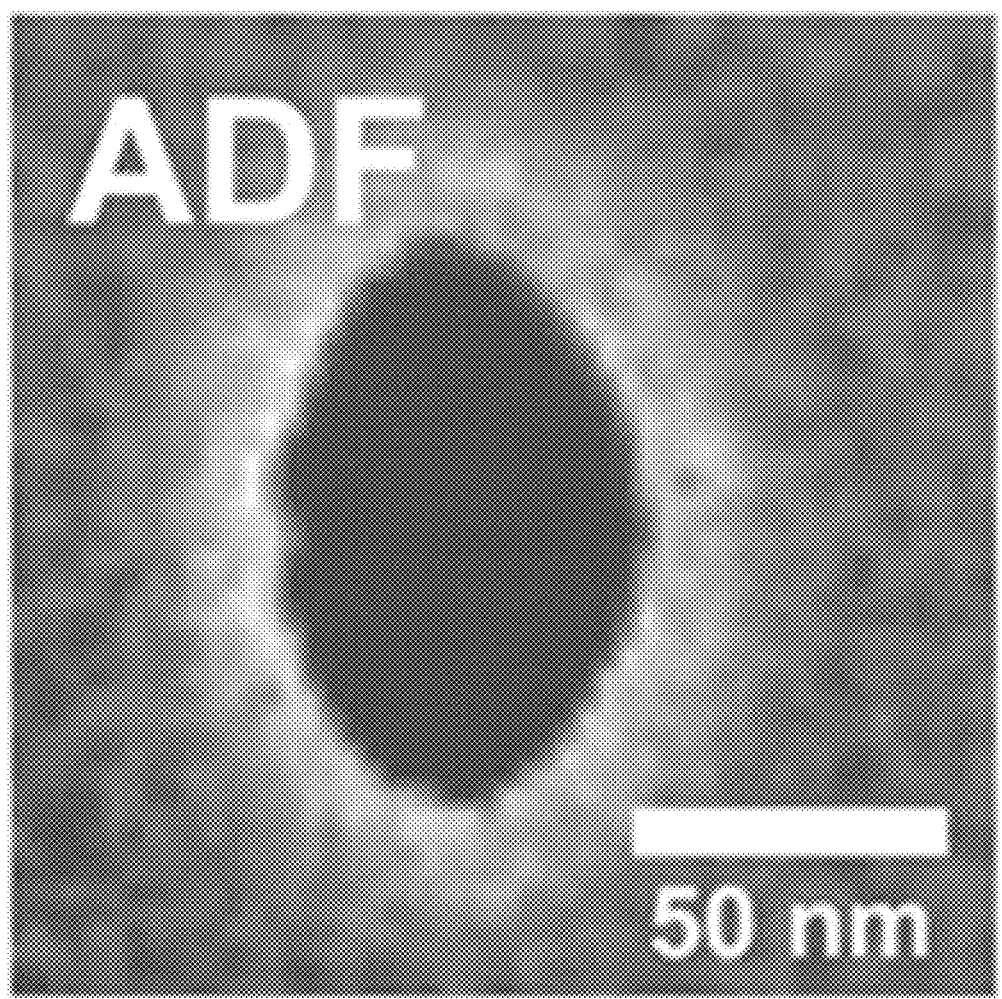
Figure 6B:
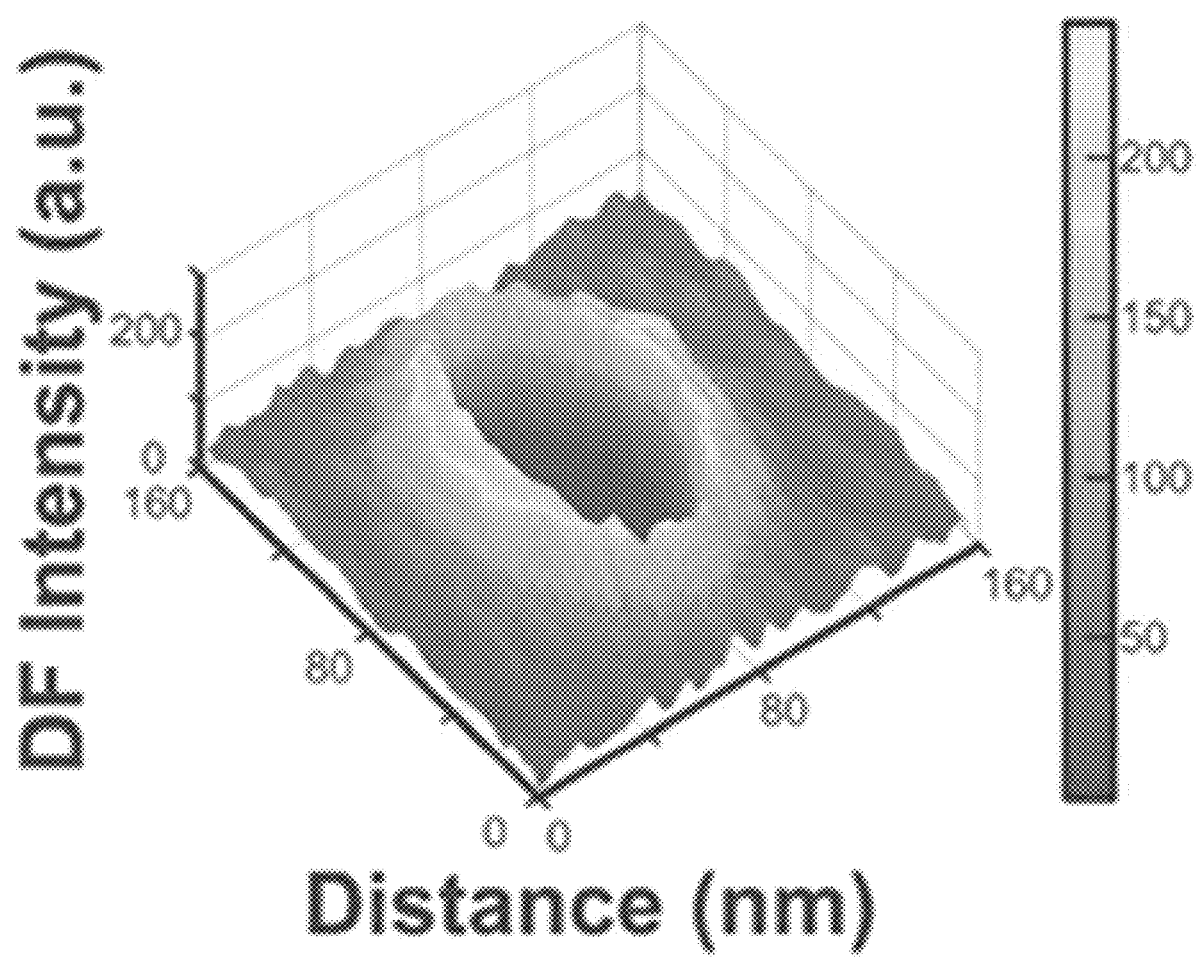
Figure 6C:
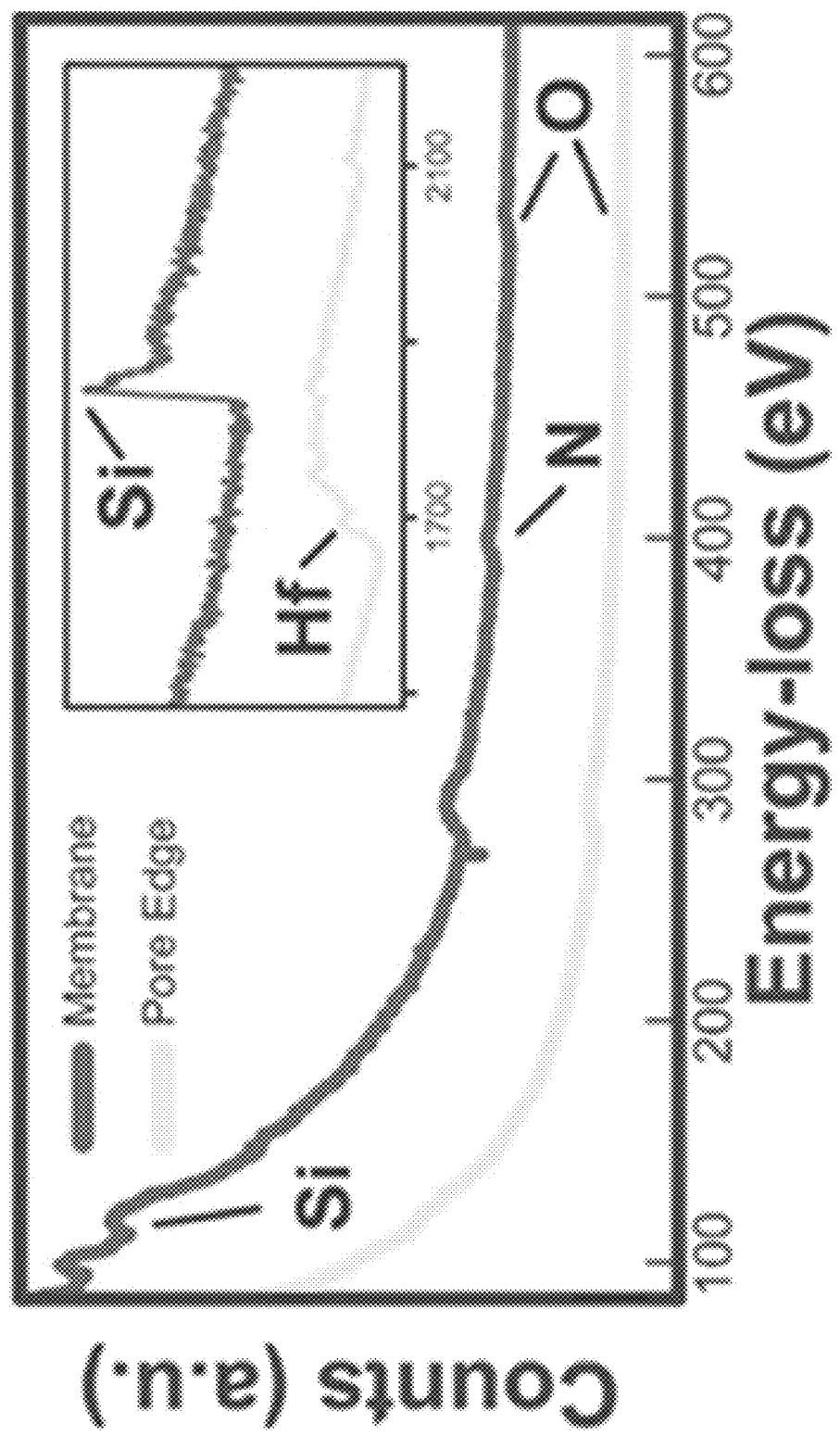
Figure 6D:
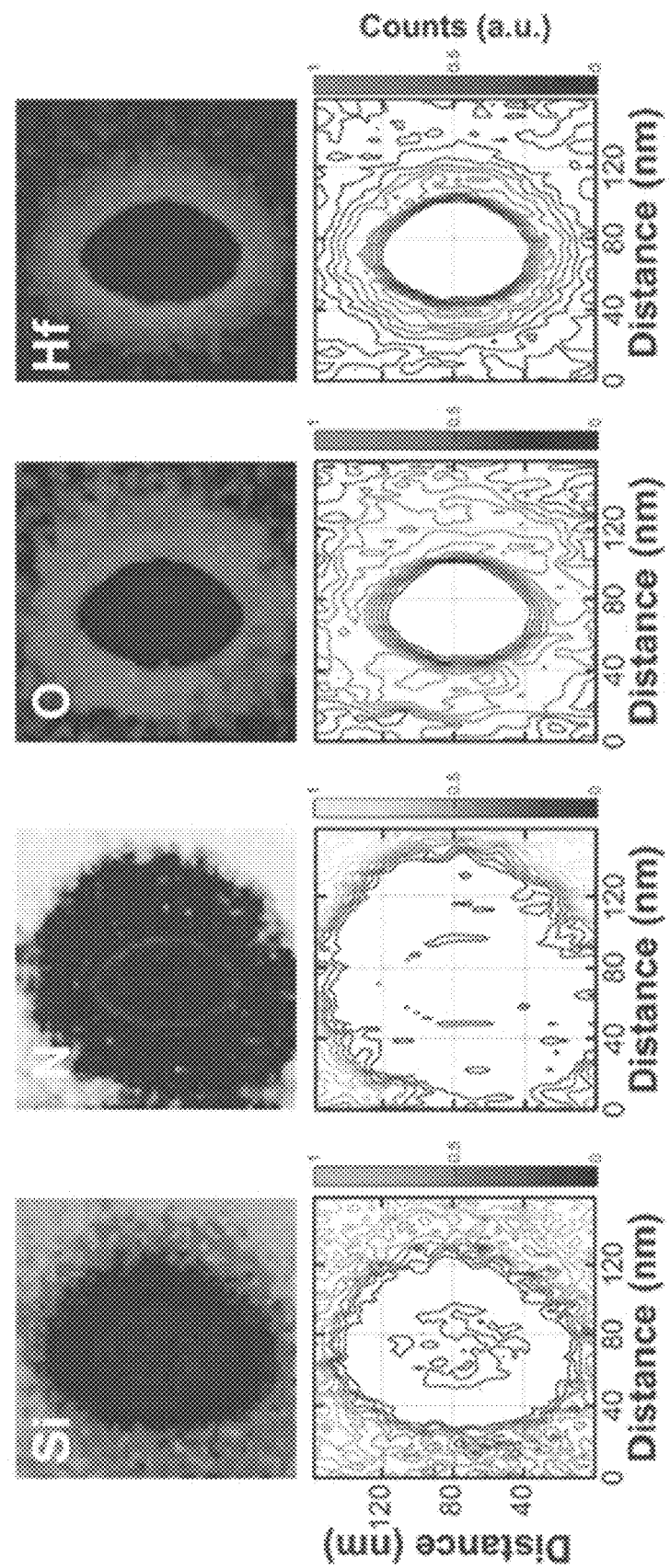

The four elemental EELS maps shown in FIG. 6d demonstrate the extent to which the TEM-drilled $SiN_x$ pore has been shrunk by the $HfO_2$ ALD coating. Maps of the Si K (green) and N K (yellow) signals in the first and second columns, respectively, of FIG. 6d reflect the original diameter of the TEM-drilled pore (i.e., before ALD) and indicate that the area surrounding the pore edge (see FIG. 6a) is largely free of $SiN_x$. As described previously to FIG. 3 for bare TEM-drilled pores, these maps also show the presence of a Si-rich, N-deficient region around the original TEM-drilled pore edge. Essentially, the O K (red) and Hf $M_4$ (purple) maps reveal a pore edge region after ALD that is entirely $HfO_2$ with a strongly localized Hf signal between the original edge of the TEM-drilled pore. This circular area has a diameter of ~20 nm and corresponds directly to the circular region of increased thickness around the pore shown in FIG. 6b. This indicates that ALD can be used to shrink the diameter of $SiN_x$ pores by introducing an $HfO_2$ passivation layer that is highly resilient to etching in salt solutions.

Conclusions

In conclusion, by performing consecutive ionic conductance measurements at low voltages (up to 0.1 V) to probe the pore size and/or by repeated TEM imaging over time, we characterized the changes in the $SiN_x$ nanopore size due to the effects of salt solutions at room temperature and ambient light. We found that the pores expand in typical electrolyte solutions and concentrations with rates varying from ~0.2 to 3 nm/day. Pore walls contain silicon oxide/silicon that can dissolve in salt solutions. This resembles chemical etching in ocean water where minerals such as silica ($SiO_2$) and silicates dissolve over long time scales. While details of diameter etch rates vary and depend on parameters such as salt type and concentration (summarized in Table 1), our observation of pore etching and expansion in ambient conditions without any voltage applied is valid for a large range of diameters (2-80 nm), thicknesses (10-100 nm) and two different pore fabrication methods. Based on previous works on laser illumination of $SiN_x$ membranes in salt solution, parameters such as the Si:N ratio in the membrane, pH, and temperature are expected to affect this process. We note that pores can be formed by simple chemical etching in salt solution, in electron-irradiated membrane regions and this phenomenon can be used as a practical pore-fabrication method, akin to electroporation, but without voltage application. We further determined that ethanol/water is useful for long-term nanopore storage purposes.

Without being bound to any theory or embodiment, Si-rich $SiN_x$ membrane regions are suitable for pore formation in salt solution (for example by irradiation and/or electroporation), but can be susceptible to pore etching and expansion. To avoid etching altogether, a few-nm-thick hafnium oxide coating, that can be as thin as 1 nm, provides a resistant layer that prevents long term etching in salt solutions over periods of days.

Materials and Methods

Nanopore Fabrication

Electron-transparent TEM windows are first fabricated in 5×5 mm² $Si/SiO_2$ chips coated with 100 nm of low-stress $SiN_x$ (at Cornell Nanofabrication Facility (CNF)) using microfabrication processes described elsewhere. The $SiN_x$ membrane is then thinned to a thickness of 10 nm using $CHF_3$ and $O_2$ reactive ion etching. Nanopores are drilled in situ at room temperature with a JEOL F200 TEM operating in high-resolution mode with an acceleration voltage of 200 kV. The probe with a current of 20 nA is momentarily condensed to the beam crossover point on the $SiN_x$ membrane for 5-10 seconds (total dose~$8.0 \times 10^{11}$ e⁻/nm²) to form a pore. Prior to ionic current measurements, pores are exposed to boiling piranha solution (1:3 v/v $H_2O_2$:$H_2SO_4$) for 10 minutes, which removes organic contaminants and aids in pore wetting. $HfO_2$ is deposited using Cambridge Nanotech S200 ALD system, with Tetrakis(dimethylamino) hafnium (HFDMA) and $H_2O$, at 150° C. Deposited thickness per cycle is calibrated at an average of 1.14 Å/cycle. The thickness of the resulting pore is later also confirmed from ionic conductance and the measured diameter, $d_{TEM}$.

Nanopore Array Fabrication

The $SiN_x$ membrane is first spin-coated with 1:2 dilution of ZEP520A: Anisole at 4000 rpm for 40 seconds, followed by a 2-minute baking at 180° C. Array patterning is exposed onto the resist layer using Elionix ELS-7500EX with a shot pitch of 100 nm and a dose of 18 μC/cm²; the resist is then developed in o-xylene for 70 seconds and isopropyl alcohol (IPA) for 30 seconds. Nanopore array is transferred into the $SiN_x$ membrane via RIE, as described above. To strip off the resist, the membrane is placed in heated N-Methyl-2-pyrrolidone (NMP) at 60° C. for 3 hours, then rinsed with IPA.

Ionic Solution Storage

Unbuffered ionic solutions were produced by dissolving KCl, $MgCl_2$, and LiCl pellets (Alfa Aesar) in ultrapure deionized (DI) water at discrete concentrations of 0.01, 0.1, 1, and 3 M. EtOH:$H_2O$ (v/v=1/1) solutions were produced by mixing equal amounts of HPLC grade ethanol (Fisher Chemical) and DI water. Individual nanopores and nanopore arrays were stored in solutions at room temperature (25° C.) and ambient light, for up to 40 days in sealed containers to minimize atmospheric gas dissolution. Prior to ionic current measurements and TEM inspection, samples were flushed with DI water to remove residue ionic solution from storage and dried with clean $N_2$ gas, respectively.

Ionic Current Measurements

Ionic measurements were acquired using a VC100 amplifier (Chimera Instruments, New York, NY) and bias voltage is applied via a set of two-terminal Ag/AgCl electrodes. All measurements are conducted in unbuffered 1M KCl (pH 8.0, $\sigma$=11.1 S/m). Conductance is estimated from the current changes given a fixed step size of voltage bias. Applied voltages were kept below 0.1 V to prevent pore expansion and/or dielectric breakdown and during the measurement period of less than 30 minutes the conductance remained constant.

TEM Image Analysis of "RIE Pores" in the Nanopore Array

Low-magnification TEM images of nanopore arrays were processed using ImageJ software. With particle analysis feature, enclosed nanopore area can be identified and obtained, owing to phase contrast difference between the pore region and the $SiN_x$ region. $d_{TEM}$ is then approximated from the total pore area equated to $\pi \times (d_{TEM}/2)^2$. A subset of 900 nanopores in FIG. 4e, out of an approximate number of 150,000 nanopores, were randomly chosen from each TEM image inspection session to determine the average nanopore diameter after each consecutive storage time in ionic solution.

ADF Imaging and EELS Measurements

Before imaging, samples exposed to salt solution were annealed at 300° C. for 90 minutes in $Ar/H_2$. Dark field images were acquired on a probe-corrected JEOL NEOARM operating at 200 kV with a high angle annular dark field (HAADF) detector. EELS spectra were acquired on a GIF Quantum Summit detector with a resolution of 0.5 eV. 80-90 square pixel EELS maps were acquired with an acquisition time of 0.2-0.5 s/pixel.

TABLE 1

Summary of average diameter etch rates measured for various salt solutions and devices discussed in the text, single nanopores and nanopore arrays included. For single nanopores data acquired from ionic measurements, errors are estimated using the average deviations from the mean values of $<\epsilon>_T^{teff}$, after measured conductance was fitted to Eq. 3. TEM imaging methods are employed for both some single nanopores and nanopore arrays. For nanopore arrays, errors are quoted as the standard deviations in the histograms of $d_{TEM}$ distributions over time (FIG. 4e.) Number of measurements (N) indicates the number of times when an inspection was performed via I-V and/or TEM. For $HfO_2$-coated pores, $t_{mem}$ was estimated as a sum of the $SiN_x$ membrane thickness and the deposition thickness.

| Storage Solution * | Measurement Methods | $t_{mem}$ (nm) | N (number of measurements) | Storage Duration, T (day) | $(E)_T^{teff=tmem/3}$ (Eq. 3) (nm/day) | $(E)_T^{teff=tmem/3}$ (Eq. 3) (nm/day) | $\Delta(d_{TEM})$ $\Delta t$ (nm/day) |
|---|---|---|---|---|---|---|---|
| 3M KCl | I-V | 10 | 4 | 9 | 2.6 ± 0.3 | 2.9 ± 03 | N/A |
| 1M KC | I-V | 10 | 5 | 78 | 1.4 ± 0.2 | 1.7 ± 02 | N/A |
|  | TEM | 20 | 6 | 1.9 | N/A | N/A | 1.9 ± 0.8 |
|  | TEM** | 20 | 10 | 1.9 | N/A | N/A | 1.9 ± 0.3 |
|  | TEM† | 100 | 5 | 12 | N/A | N/A | 1.7 ± 0.9 |
|  | TEM‡ | 20 | 6 | 2 | N/A | N/A | 2.1 ± 0.1 |
| 0.1M KCl | I-V | 10 | 3 | 5 | 0.9 ± 0.1 | 12 ± 0.1 | N/A |
| 1M LiCl | I-V | 10 | 7 | 15 | 0.9 ± 0.4 | 12 ± 0.1 | N/A |
|  | TEM | 20 | 18 | 0.8 | N/A | N/A | 1.4 ± 0.3 |
| 1M $MgCl_2$ | I*V/TEM | 10 | 5/2 | 11 | 0.6 ± 0.2 | 0.8 ± 0.2 | 0.5 ± 0.2 |
| 0.01M KCl | I-V | 10 | 4 | 8 | 0.14 ± 0.01 | 0.21 ± 0.01 | N/A |
| 1M KCl | I-V | 10 + 2 | 6 | 6 | 0.3 ± 0.2 | 0.4 ± 03 | N/A |
| (with $HfO_2$) | TEM | 20 + 5 | 4 | 6 | N/A | N/A | ≈const. |
| $EtOH/H_2O$ | I-V | 10 | 7 | 40 | 0.0 ± 0.1 | 0.0 ± 0.1 | N/A |

* Note: all samples are stored and measured under room temperature and ambient light (pH 8.0) unless further noted.
**$SiN_x$/Si chip.
†Nanopores are fabricated with reactive ion etching. Each measurement contains a randomly chosen subset of 900 pores on the chip.
‡Commercial $SiN_x$/Si chip from SPI supplies. Sample was stored for 2 days under room temperature and ambient light and for 1 hour under heated 1M KCl solution at 60° C..

TEM Imaging

About 18 single pores were imaged by TEM to directly measure their diameter. First, the pore was drilled in the "TEM mode" of the F200 JEOL high-resolution TEM and then imaged to obtain the initial $d_{TEM}$. The pore was then taken away from vacuum and clean with piranha, rinsed with DI water, and immersed in salt solution for some period of time, for example for ~2 days. The pores were then taken out of solution, rinsed with DI water, dried with $N_2$ gas, and imaged in the TEM vacuum chamber to obtain a second TEM image of the pore, from which the new diameter was measured. The error in diameter measurement from these images is about 0.1 nm. Except for pore vii in FIG. 3a, we did not perform conductance measurements on these pores to minimize chip handling in and out of salt solutions and possible chip failure modes.

TABLE 2

| Days | G (nS) | $d_{calc}^{teff=10\ nm/3\ nm}$ |
|---|---|---|
| 0 | 31.3 | 7.6/5.2 |
| 7 | 141.7 | 20.6/16.1 |
| 8.8 | 164.3 | 23.0/18.3 |
| 13.9 | 210.4 | 27.6/22.5 |
| 77.9 | 918.2 | 94.0/86.8 |

Recorded conductance, G, for the nanopore stored in 1M KCl shown in FIG. 2C. Corresponding $d_{calc}$ were obtained from Eq. 1 in the main text assuming $t_{eff} = t_{mem} = 10$ nm (case 1) and $t_{eff} = t_{mem}/3 \approx 3$ nm (case 2), respectively. The I-V characteristics of this nanopore were consecutively measured five times, up to 78 days.

FIG. 13 provides a cross-sectional view of a component 1300 according to the present disclosure. As shown, a component can comprise a first substrate 1304 (which can also be termed a membrane), which substrate has one or more pores (1310a, 1310b, and 1310c) formed therein. First substrate 1304 can be a silicon nitride, e.g., of the formular $SiN_x$.

First substrate 1304 can define a thickness in the range of from in the range of from about 0.5 nm to about 100 nm (and all intermediate values and ranges), e.g., from about 1 nm to about 90 nm, or from about 2 nm to about 85 nm, or from about 3 nm to about 80 nm, or from about 4 nm to about 70 nm, or from about 5 nm to about 60 nm, or from about 6 nm to about 60 nm, or from about 7 nm to about 50 nm, or from about 8 nm to about 40 nm, or from about 9 nm to about 30 nm, or from about 10 nm to about 20 nm.

The pores can be at least partially coated with coating 1306, which coating 1306 can be, e.g., $HfO_2$. The coating can be a monolayer; the coating can also define a thickness in the range of, e.g., from about 1 nm to about 20 nm, or from about 3 nm to about 17 nm, or from about 5 nm to about 15 nm, or from about 7 nm to about 13 nm, or from about 9 nm to about 11 nm. The coating can be present on (1) an inner surface of a pore, (2) an upper surface of a pore, (3) a lower surface of a pore, (4) an edge of a pore (i.e., the region that connects the upper surface of the pore and the inner surface of the pore) or any combination thereof. Without being bound to any particular theory or embodiment, coating present on an upper surface of a pore is considered especially suitable, as is coating present on an upper surface of a pore and an inner surface of the pore.

A pore of first substrate 1304 can define a width w1, which width can be, e.g., the diameter of the pore; for pores that include coating on an inner surface, the width w1 is the diameter defined by the coating. Width w1 can be, e.g., in the range of from about 0.5 nm to about 100 nm (and all intermediate values and ranges), e.g., from about 1 nm to about 90 nm, or from about 2 nm to about 85 nm, or from about 3 nm to about 80 nm, or from about 4 nm to about 70 nm, or from about 5 nm to about 60 nm, or from about 6 nm to about 60 nm, or from about 7 nm to about 50 nm, or from about 8 nm to about 40 nm, or from about 9 nm to about 30 nm, or from about 10 nm to about 20 nm. h1 can also range from about 1 nm to about 15 nm, from about 2 nm to about 14 nm, from about 3 nm to about 13 nm, from about 4 nm to about 12 nm, from about 5 nm to about 11 nm, from about 6 nm to about 10 nm, from about 7 nm to about 9 nm, or even about 8 nm.

A pore of first substrate 1304 can define a height h1. Height h1 (which includes the thickness of coating 1306, if present) can be in the range of from about 0.5 nm to about 100 nm (and all intermediate values and ranges), e.g., from about 1 nm to about 90 nm, or from about 2 nm to about 85 nm, or from about 3 nm to about 80 nm, or from about 4 nm to about 70 nm, or from about 5 nm to about 60 nm, or from about 6 nm to about 60 nm, or from about 7 nm to about 50 nm, or from about 8 nm to about 40 nm, or from about 9 nm to about 30 nm, or from about 10 nm to about 20 nm. h1 can also range from about 1 nm to about 15 nm, from about 2 nm to about 14 nm, from about 3 nm to about 13 nm, from about 4 nm to about 12 nm, from about 5 nm to about 11 nm, from about 6 nm to about 10 nm, from about 7 nm to about 9 nm, or even about 8 nm.

As shown, component 1300 can include second substrate 1308 (which can also be termed a membrane). Second substrate 1308 can be a silicon nitride, e.g., of the formular $SiN_x$.

Second substrate 1308 can define a thickness of from about 1 nm to about 100 nm, e.g., from about 1 nm to about 100 nm, from about 5 nm to about 90 nm, from about 7 nm to about 80 nm, from about 8 nm to about 70 nm, from about 10 nm to about 60 nm, from about 15 nm to about 50 nm, or even from about 20 nm to about 40 nm. The second substrate can have a thickness in the range of from about 10 nm or about 20 nm to about 100 nm, from about 30 nm to about 100 nm, from about 40 nm to about 100 nm, from about 50 nm to about 100 nm, from about 60 nm to about 100 nm, from about 70 nm to about 100 nm, from about 80 nm to about 100 nm, or even from about 90 nm to about 100 nm, and all intermediate values.

Second substrate can also define a thinned region 1314, which thinned region defines a height h2, which height h2 can be from about 5 nm to about 50 nm. The thinned region can also define a cross-sectional dimension w2, which can be in the range of from about 20 nm to about 1 micrometer, e.g., from about 20 nm to about 1000 nm, from about 30 nm to about 700 nm, from about 50 nm to about 600 nm, from about 70 nm to about 500 nm, from about 80 nm to about 400 nm, from about 100 nm to about 300 nm, or even from about 150 nm to about 250 nm. Thinned region 1314 can be circular in shape, but this is not a requirement, as the thinned region 1314 can also be polygonal in shape or even be irregular in shape.

A pore 1312 can be formed in the thinned region 1314 of second substrate 1308. Pore 1302 can define a width w3 of from 0.5 nm to about 20 nm (e.g., from about 0.5 nm to about 20 nm, from about 1 nm to about 18 nm, from about 2 nm to about 16 nm, from about 3 nm to about 15 nm, from about 4 nm to about 13 nm, from about 5 nm to about 12 nm, from about 6 nm to about 11 nm, from about 7 nm to about 10 nm, or from about 8 nm to about 9 nm.

Height h3 can be, e.g., from about 0.5 nm to about 100 nm (and all intermediate values and ranges), e.g., from about 1 nm to about 90 nm, or from about 2 nm to about 85 nm, or from about 3 nm to about 80 nm, or from about 4 nm to about 70 nm, or from about 5 nm to about 60 nm, or from about 6 nm to about 60 nm, or from about 7 nm to about 50 nm, or from about 8 nm to about 40 nm, or from about 9 nm to about 30 nm, or from about 10 nm to about 20 nm. h1 can also range from about 1 nm to about 15 nm, from about 2 nm to about 14 nm, from about 3 nm to about 13 nm, from about 4 nm to about 12 nm, from about 5 nm to about 11 nm, from about 6 nm to about 10 nm, from about 7 nm to about 9 nm, or even about 8 nm.

Height h3 can be from about 1% to about 99% of the thickness of membrane 1308, e.g., from about 1% to about 99%, from about 4% to about 90%, from about 7% to about 87%, from about 11% to about 77%, from about 15% to about 70%, from about 20% to about 70%, from about 25% to about 65%, from about 30% to about 60%, from about 37% to about 47%, or even about 30%.

Pore 1312 can comprise a coating (not shown) disposed thereon, e.g., on (1) an inner surface of the pore, (2) an upper surface of the pore, (3) a lower surface of the pore, (4) an edge of the pore (i.e., the region that connects the upper surface of the pore and the inner surface of the pore) or any combination thereof. Support 1310 (which can be, e.g., silicon, a silicon nitride, or a silicon oxide) can provide support to second substrate 1308.

Without being bound to any particular theory or embodiment, the ratio of w1 to w3 can be from about 1:10 to about 10:1, or from about 1:8 to about 8:1, or from about 1:6 to about 6:1, or from about 1:4 to about 4:1, or from about 1:3 to about 3:1, or from about 1:2 to about 2:1, or even about 1:1. The ratio of w1 to w3 can be from about 1:1.9 to about 1.9:1, or from about 1:1.8 to about 1.8:1, or from about 1:1.7 to about 1.7:1, or from about 1:1.6 to about 1.6:1, or from about 1:1.5 to about 1.5:1, or from about 1:1.4 to about 1.4:1, or from about 1:1.3 to about 1.3:1, or from about 1:1.2 to about 1.2:1, or from about 1:1.1 to about 1:1.1.

Also without being bound to any particular theory or embodiment, the ratio of h1 to h3 can be from about 1:10 to about 10:1, or from about 1:8 to about 8:1, or from about 1:6 to about 6:1, or from about 1:4 to about 4:1, or from about 1:3 to about 3:1, or from about 1:2 to about 2:1, or even about 1:1. The ratio of w1 to w3 can be from about 1:1.9 to about 1.9:1, or from about 1:1.8 to about 1.8:1, or from about 1:1.7 to about 1.7:1, or from about 1:1.6 to about 1.6:1, or from about 1:1.5 to about 1.5:1, or from about 1:1.4 to about 1.4:1, or from about 1:1.3 to about 1.3:1, or from about 1:1.2 to about 1.2:1, or from about 1:1.1 to about 1:1.1.

As shown in FIG. 14, a component 1300 can be used to linearize a macromolecule 1320. As shown, macromolecule (which can be, e.g., small RNA (shorter than 200 nt) and long RNA (longer than 200 nt). lncRNA and m mRNA are suitable, as are 5.8S ribosomal RNA (rRNA), 5S rRNA, transfer RNA (tRNA), microRNA (miRNA), small interfering RNA (siRNA), small nucleolar RNA (snoRNAs), Piwi-interacting RNA (piRNA), tRNA-derived small RNA (tsRNA), small rDNA-derived RNA (srRNA), dsRNA, dsDNA, and ssDNA) can first pass through pore 1310a formed in first substrate 1304—which passage can at least partially linearize or untangle macromolecule 1320) and then through pore 1312 formed in second substrate 1308. Without being bound to any particular theory or embodiment, one or more signals related to the passage through either or both of pores 1310a and 1312 can be collected. Such signals can be indicative of a structure of the macromolecule, e.g., a base or other monomer unit in the macromolecule.

As shown in FIG. 14, macromolecule 1320 passes first through pore 1310a, which pore 1310a is closest to being in register (or is in register) with pore 1312. This is not a requirement, however. As shown in FIG. 15, macromolecule 1320 can pass first through pore 1310b and then through pore 1312, even though pore 1310a is closest to being in register with pore 1312. First substrate 1304 and second substrate 1308 can be arranged such that one or more pores of first substrate 1304 are in register (or at least in partial register) with a pore of second substrate 1308. This is, however, not a requirement, as the pores of first substrate 1304 need not be in register with any pore of second substrate 1308.

FIG. 16 provides a view of an example component according to the present disclosure. As shown, a component can include, e.g., first substrate 1304, which substrate can have pores 1310a and 1310b formed therein. Coating 1306 can also be disposed on first substrate 1304; as described elsewhere herein, coating 1306 (which can be $HfO_2$) can be disposed e.g., on (1) an inner surface of a pore, (2) an upper surface of a pore, (3) a lower surface of the pore. (4) an edge of a pore (i.e., the region that connects the upper surface of the pore and the inner surface of the pore) or any combination thereof. Support material 1328 (which can be, e.g., silicon, silicon nitride, or silicon oxide) can support first substrate 1304, and a further support material 1330 (which can be, e.g., silicon, a silicon nitride, or a silicon oxide) can support the support material 1328. As shown, windows can be formed in support material 1328 and in the further support material 1330; such windows can be in register with the pores formed in first substrate 1304.

As shown, second substrate 1308 can have thinned region 1314 formed therein, with pore 1312 formed in thinned region 1314. A support material 1310 can support second substrate 1310, and further support material 1311 (which can be, e.g., silicon, a silicon nitride, or a silicon oxide) can support the support material 1310. As shown, windows can be formed in support material 1310 and in the further support material 1311; such windows can be in register with pores formed in first substrate 1308.

FIG. 17 provides exemplary results from the disclosed technology. As shown, the disclosed technology allows for, e.g., $HfO_2$ coating placed on a membrane, e.g., $SiN_x$. The coating can be placed on one or both sides of a pore formed in the membrane, and the coating can even be present along at least a portion of an interior wall of the pore. In one example fabrication, atomic layer deposition (ALD) and reactive ion etching (RIE) are used to form such a coated pore; the example pore shown in FIG. 17 has a thickness of 13 nm (10 nm of $SiN_x$ membrane and 3 nm of $HfO_2$).

FIG. 18 provides exemplary results from the disclosed technology. As shown in FIG. 18, in the area closest to the pore, the $HfO_2$ (green) is in crystalline form and in the area further from the pore the $HfO_2$ (red/pink) is in amorphous form. Without being bound by any particular theory or embodiment, the fabrication process can in some cases give rise to a crystalline region of $HfO_2$ closer to the pore, with amorphous $HfO_2$ persisting further away from the pore. In some embodiments, a device can include a region of crystalline $HfO_2$ close to the pore, with a region free of $HfO_2$ further away from the pore, and then a region of amorphous $HfO_2$ still further away from the pore. Thus, one can have a pore at least partially encircled by a region of crystalline $HfO_2$, with the region of crystalline $HfO_2$ at least partially encircled by an area free of $HfO_2$, with that area in turn at least partially encircled by an area of amorphous $HfO_2$.

FIG. 19 provides further exemplary results from the disclosed technology. As shown, in the boxed area (shown by the white box), the $HfO_2$ is crystalline in form and that the $HfO_2$ is amorphous further away from the pore.

Aspects

The following Aspects are illustrative only and do not serve to limit the scope of the present disclosure or the appended claims.

Aspect 1. An etch-resistant nanopore component, comprising: a membrane, the membrane having a pore extending therethrough, the pore defining an edge and defining an inner wall; and a coating of hafnium oxide surmounting at least a portion of the edge and the inner wall of the pore, the pore having, inclusive of the coating of hafnium oxide, a narrowest cross-sectional dimension of from about 1 nm to about 100 nm.

It should be understood that a membrane can include a pore that is at least partially coated with hafnium oxide and a pore that is not coated with hafnium oxide. Such pore can be adjacent to one another, e.g., a hafnium-oxide coated pore adjacent to a pore that is not coated with hafnium oxide.

Without being bound to any particular theory or embodiment, the disclosed etch-resistant (or "stable") components can be such that the diameter of a nanopore of the component remains essentially unchanged (e.g., increases by 12-15% or less, or increases by less than about 1 nm/day, less than 0.7 nm/day, less than 0.6 nm/day, less than 0.5 nm/day, less than 0.4 nm/day, less than 0.3 nm/day, less than 0.2 nm/day, or even less than 0.1 nm/day) after prolonged exposure to an etchant, e.g., 1 M KCl for 6 days. The diameter increase can be, e.g., from about 0.01 to about 1 nm/day, or even from about 0.01 to about 0.5 nm/day, or even 0.01 to about 0.1 nm/day.

Again without being bound to any particular theory or embodiment, by comparison, uncoated (e.g., bare SiN)

nanopores exhibit diameter increase (i.e., are unstable) when exposed to comparable salt solution conditions as hafnium oxide-coated nanopores.

The narrowest cross-sectional dimension (e.g., in the case of a round pore, the diameter) can be, e.g., from about 1 nm to about 100 nm (including all intermediate values and ranges), from about 2 nm to about 75 nm, from about 3 nm to about 75 nm, from about 4 nm to about 65 nm, from about 5 nm to about 50 nm, from about 6 nm to about 40 nm, or even from about 7 nm to about 35 nm. Dimensions in the range of from about 1 nm to about 15 nm (e.g., from about 2 to about 10 nm) are considered especially suitable.

Aspect 2. The component of Aspect 1, wherein the membrane comprises silicon nitride.

Aspect 3. The component of any one of Aspects 1-2, wherein the coating of hafnium oxide defines a thickness, at a location along the coating, in the range of from about 0.1 nm to about 2.0 nm. As shown elsewhere herein, the hafnium oxide coating can be conformal, such that the coating does not completely occlude the pore.

Aspect 4. The component of any one of Aspects 1-3, wherein the pore is characterized as an hourglass in configuration.

Aspect 5. The component of any one of Aspects 1-3, wherein the pore is characterized as essentially cylindrical in configuration. A pore can have an essentially constant cross-sectional dimension (e.g., diameter), but the cross-sectional dimension can vary along the length of the pore. As an example, a pore can be flared at the top, bottom, or both. A pore can be funnel-shaped, as one example.

Aspect 6. The component of any one of Aspects 1-5, wherein the component contacts a salt solution.

Aspect 7. The component of any one of Aspects 1-6, wherein the first membrane comprises a electron-beam irradiated thinned region through which the pore extends.

Aspect 8. The component of any one of Aspects 1-7, wherein the first membrane comprises a plurality of pores extended therethrough, each of the plurality of pores defining an edge and an inner wall, and each of the edges and inner walls being surmounted by the coating of hafnium oxide.

Aspect 9. The component of any one of Aspects 1-8, wherein the first membrane defines a thickness of from about 1 nm to about 100 nm.

Aspect 10. The component of any one of Aspects 1-9, wherein the narrowest cross-sectional dimension of the pore remains essentially constant upon exposure to 1 M KCl for about 6 days. An example is shown in non-limiting FIG. 5(*b*), which FIG. shows that the diameter of a hafnium-oxide coated pore remains essentially unchanged over the course of a 6-day exposure to 1 M KCl. (By comparison, an uncoated or "bare" SiN pore experiences a diameter increase of about 1.7 nm per day during the same 6-day course of exposure to 1 M KCl.) A hafnium oxide-coated pore can retain essentially the same diameter for 1, 2, 3, 4, 5, 6, 7, 8, 9, or even 10 days under exposure to 1 M KCl.

Aspect 11. The component of any one of Aspects 1-10, wherein the first membrane is supported by a silicon oxide layer. The pore can extend through the silicon oxide layer. Alternatively, the silicon oxide layer can include an opening that is in at least partial register with the pore.

Aspect 12. The component of Aspect 11, wherein the silicon oxide layer defines a thickness of about 5 micrometers.

Aspect 13. The component of Aspect 11, wherein the silicon oxide first membrane is further supported by a silicon platform. The pore can extend through the silicon platform layer. Alternatively, the silicon platform can include an opening that is in at least partial register with the pore.

Aspect 14. A method, comprising: translocating a macromolecule through the pore of a component according to any one of Aspects 1-13. Example macromolecules include polymers, e.g., single- and/or double-stranded RNA, DNA, and the like.

As but some examples, the macromolecule can include, e.g., small RNA (shorter than 200 nt) and long RNA (longer than 200 nt). lncRNA and m mRNA are suitable, as are 5.8S ribosomal RNA (rRNA), 5S IRNA, transfer RNA (IRNA), microRNA (miRNA), small interfering RNA (siRNA), small nucleolar RNA (snoRNAs), Piwi-interacting RNA (piRNA), IRNA-derived small RNA (tsRNA), small rDNA-derived RNA (srRNA), dsRNA, dsDNA, and ssDNA.

Aspect 15. The method of Aspect 14, further comprising applying a gradient to effect the translocation. Such a gradient can be, e.g., an electric field, a magnetic field, a pressure gradient, and the like.

Aspect 16. The method of any one of Aspects 14-15, further comprising collecting one or more signals evolved during the translocating. A signal can be, e.g., a current, a resistance, a voltage, and the like. One can, for example, monitor a current at the pore and monitor changes in the current as a molecule is translocated through the pore. In the case of ssDNA, each base of the ssDNA can give rise to a different signal as the base translocates through the pore. A user can then correlate the signals to the base that evolved the signal (e.g., by comparing a collected signal with a signal standard or calibration), and thus derive the order of bases in the macromolecule that was translocated through the pore.

Aspect 17. The method of Aspect 16, further comprising correlating the one or more signals to one or more structural characteristics of the macromolecule. Such a characteristic can be, e.g., the presence of a base in ssDNA, the order of bases in ssDNA, and the like.

Aspect 18. The method of any one of Aspects 14-17, wherein the macromolecule is an oligonucleotide or a polynucleotide.

Aspect 19. A method, comprising: forming a pore extending through a first membrane, the pore defining an edge and an inner wall; and applying a hafnium oxide coating so as to surmount at least a portion of the edge and at least a portion of the inner wall, the pore having, inclusive of the coating of hafnium oxide, a narrowest cross-sectional dimension of from about 1 nm to about 100 nm. As described elsewhere herein, the hafnium oxide can be applied such that the hafnium oxide does not completely occlude the pore.

Aspect 20. The method of Aspect 19, further comprising forming a thinned region in the first membrane and forming the pore such that the pore extends through the thinned region of the first membrane. The thinned region can be formed by, e.g., ions, electrons, lasers, chemical etching, and the like. Electron beam thinning is considered especially suitable.

Aspect 21. A method, comprising: measuring a first ionic conductance value measured across a nanopore to an estimated diameter of the nanopore and correlating the first ionic conductance value to a first estimated diameter of the nanopore.

Aspect 22. The method of Aspect 21, wherein the ionic conductance value is measured at a first time, measuring a second ionic conductance value at a second time, correlating the second ionic conductance value to a second estimated diameter of the nanopore, and determining a change in nanopore diameter as a matter of time.

Aspect 23. A method, comprising: forming a pore extending through a first membrane, the pore defining an edge and an inner wall and the pore further defining a narrowest cross-sectional dimension; contacting the first membrane with a salt solution under conditions sufficient to effect an etching of the pore that increases the narrowest cross-sectional dimension; and applying a hafnium oxide coating so as to surmount at least a portion of the edge and at least a portion of the inner wall.

Forming the pore can be by, e.g., ion beam, electron beam, chemical etching (including, but not limited to, application of KCl or other salt solution, to the first membrane, especially to a thinned region of the first membrane), and the like.

Aspect 24. The method of Aspect 23, wherein the applying is performed when the narrowest cross-sectional dimension of the pore reaches a predetermined value of from about 1 nm to about 10 nm.

Aspect 25. The method of any one of Aspects 23-24, wherein the hafnium oxide coating defines a thickness, the thickness at its narrowest point being from about 0.1 nm to about 2.0 nm.

Aspect 26. The component of any one of Aspects 1-13, further comprising: a second membrane defining a thickness, the second membrane having a pore extending there through, the pore of the second membrane defining an edge and defining an inner wall, and the first membrane and the second membrane being arranged such a line can be drawn so as to extend through the thickness of the first membrane and the second membrane.

Aspect 27. The component of Aspect 26, wherein the second membrane comprises a thinned region through which the pore of the second membrane extends.

Aspect 28. The component of any one of Aspects 26-27, wherein the pore of the first membrane is at least partially in register with the pore of the second membrane.

Aspect 29. The component of any one of Aspects 26-27, wherein the first membrane defines a plurality of pores formed therein.

Aspect 30. The component of Aspect 29, wherein at least one pore of the first membrane is at least partially in register with the pore of the second membrane.

Aspect 31. The component of any one of Aspects 26-30, further comprising a coating of hafnium oxide surmounting at least a portion of the edge and the inner wall of the pore of the second membrane.

Aspect 32. The component of any one of Aspects 26-31, wherein the pore (of the second membrane) is characterized as an hourglass in configuration.

Aspect 33. The component of any one of Aspects 26-31, wherein the pore (of the second membrane) is characterized as essentially cylindrical in configuration.

Aspect 34. A component, comprising: a first membrane, the first membrane defining one or more pores formed therein, an amount of hafnium oxide surmounting at least a portion of the one or more pores of the first membrane; a second membrane, the second membrane defining a thinned region and defining a pore formed through the thinned region, the first membrane and the second membrane being arranged such that a line can be drawn so as to extend through the thickness of the first membrane and the thickness of the second membrane.

Aspect 35. The component of Aspect 34, wherein at least one pore of the first membrane is at least in partial register with the pore of the second membrane.

Aspect 36. A method, comprising: translocating a macromolecule through the pore of a component according to any one of Aspect 34-35.

Aspect 37. The method of Aspect 36, further comprising applying a gradient to effect the translocation.

Aspect 38. The method of any one of Aspects 36-37, further comprising collecting one or more signals evolved during the translocating.

Aspect 39. The method of Aspect 38, further comprising correlating the one or more signals to one or more structural characteristics of the macromolecule.

Aspect 40. The method of any one of Aspect 36-39, wherein the macromolecule is an oligonucleotide or a polynucleotide.

What is claimed:

1. An etch-resistant nanopore component, comprising:
   a first membrane,
   the membrane having a pore extending therethrough,
   the pore having an inner wall defined by the membrane; and
   a coating of hafnium oxide conforming to and surmounting at least a portion of the inner wall, and
   the pore having, inclusive of the coating of hafnium oxide, a narrowest cross-sectional dimension of from about 1 nm to about 100 nm.

2. The component of claim 1, wherein the membrane comprises silicon nitride.

3. The component of claim 1, wherein the coating of hafnium oxide defines a thickness, at a location along the coating, in the range of from about 0.1 nm to about 2 nm.

4. The component of claim 1, wherein the pore is characterized as an hourglass in configuration.

5. The component of claim 1, wherein the pore is characterized as essentially cylindrical in configuration.

6. The component of claim 1, wherein the membrane comprises a thinned region through which the pore extends.

7. The component of claim 1, wherein the membrane comprises a plurality of pores extended therethrough, each of the plurality of pores defining an edge and an inner wall, and each of the edges and inner walls being surmounted by the coating of hafnium oxide.

8. The component of claim 1, wherein the membrane defines a thickness of from about 1 nm to about 100 nm.

9. The component of claim 1, wherein the narrowest cross-sectional dimension of the pore remains essentially constant upon exposure to 1 M KCl for about 6 hours.

10. The component of claim 1, wherein the membrane is supported by a silicon oxide layer.

11. A method, comprising: translocating a macromolecule through the pore of a component according to claim 1.

12. The method of claim 11, further comprising applying a gradient to effect the translocation.

13. The method of claim 11, further comprising collecting one or more signals evolved during the translocating.

14. The method of claim 13, further comprising correlating the one or more signals to one or more structural characteristics of the macromolecule.

15. The method of claim 11, wherein the macromolecule is an oligonucleotide or a polynucleotide.

16. The component of claim 1, further comprising:
    a second membrane defining a thickness,
    the second membrane having a pore extending there through,
    the pore of the second membrane defining an edge and defining an inner wall, and
    the first membrane and the second membrane being arranged such a line can be drawn so as to extend through the thickness of the first membrane and the thickness of the second membrane.

17. The component of claim 16, wherein the second membrane comprises a thinned region through which the pore of the second membrane extends.

18. The component of claim 16, wherein the pore of the first membrane is at least partially in register with the pore of the second membrane.

19. The component of claim 16, wherein the first membrane defines a plurality of pores formed therein.

20. The component of claim 19, wherein at least one pore of the first membrane is at least partially in register with the pore of the second membrane.

21. The component of claim 16, further comprising a coating of hafnium oxide surmounting at least a portion of the edge and the inner wall of the pore of the second membrane.

22. A method, comprising:
   forming a pore extending through a membrane,
   the pore having an edge and having an inner wall defined by the membrane; and
   applying a hafnium oxide coating so as to conform to and surmount at least a portion of the inner wall,
   the pore having, inclusive of the coating of hafnium oxide, a narrowest cross-sectional dimension of from about 1 nm to about 100 nm.

23. The method of claim 22, further comprising forming a thinned region in the membrane and forming the pore such that the pore extends through the thinned region of the membrane.

\* \* \* \* \*

UNITED STATES PATENT AND TRADEMARK OFFICE
CERTIFICATE OF CORRECTION

PATENT NO. : 12,222,346 B2
APPLICATION NO. : 17/218365
DATED : February 11, 2025
INVENTOR(S) : Marija Drndic et al.

Page 1 of 4

It is certified that error appears in the above-identified patent and that said Letters Patent is hereby corrected as shown below:

On the Title Page

In Other Publications,

Under Column no. 2, Line no. 1, Item (56) Replace:
"Blocked lonic Current"
With:
--Blocked Ionic Current--

Under Column no. 2, Page 2, Line no. 18, Item (56) Replace:
"of lon Transport"
With:
--of Ion Transport--

In the Specification

Under Column no. 3, Line no. 12, Replace:
"with (G)=5.6"
With:
--with ⟨G⟩=5.6--

Under Column no. 4, Line no. 43, Replace:
"$d_{EELS}$~30 nm."
With:
--$d_{EELS} \approx 30$ nm--

Under Column no. 4, Line no. 61, Replace:
"be A $(d_{TEM})/\Delta t$"
With:
--be $\Delta(d_{TEM})/\Delta t$--

Signed and Sealed this
First Day of April, 2025

Coke Morgan Stewart
*Acting Director of the United States Patent and Trademark Office*

CERTIFICATE OF CORRECTION (continued)
U.S. Pat. No. 12,222,346 B2

Under Column no. 5, Line no. 13, Replace:
"be, $(d_{TEM})=54.8$"
With:
--be, $\langle d_{TEM}\rangle=54.8$--

Under Column no. 8, Line no. 32, Replace:
"Si:N~3:4"
With:
--Si:N≈3:4--

Under Column no. 8, Line no. 32, Replace:
"(x=1.3)."
With:
--(x≈1.3).--

Under Column no. 9, Line no. 28, Replace:
"where/is the"
With:
--where I is the--

Under Column no. 9, Line no. 45, Replace:
"to +20 V)"
With:
--to ±20 V)--

Under Column no. 9, Line no. 57, Replace:
"corresponding d calc increased"
With:
--corresponding $d_{calc}$ increased--

Under Column no. 9, Line no. 61, Replace:
"rate, Adcalc/Δt="
With:
--rate, $\Delta d_{calc}/\Delta t=$--

Under Column no. 10, Line no. 1, Replace:
"(assuming $t_{eff}$-3 nm"
With:
--(assuming $t_{eff}=3$ nm)--

Under Column no. 10, Line no. 31, Replace:
"rates, ε1 to"
With:
--rates, $\varepsilon_1$ to--

CERTIFICATE OF CORRECTION (continued)
U.S. Pat. No. 12,222,346 B2

Under Column no. 11, Line no. 14, Replace:
"coefficients, $\gamma_{Cl^-}^2$, for"
With:
--coefficients, $\gamma_{Cl^-}$, for--

Under Column no. 11, Line no. 31, Replace:
"with (G)=5.6"
With:
--with $\langle G \rangle$=5.6--

Under Column no. 11, Line no. 50, Replace:
"$t_{mem}$~3 nm,"
With:
--$t_{mem} \approx$ 3 nm,--

Under Column no. 11, Line no. 63, Replace:
"f(t)=n ($d_o$"
With:
--f(t)=$\sqcap$ ($d_o$--

Under Column no. 11, Line no. 65, Replace:
"with $\langle\varepsilon\rangle$T=15 days~1.6 nm/day,"
With:
--with $\langle\varepsilon\rangle_{T=15\ days} \approx$ 1.6 nm/day,--

Under Column no. 12, Line no. 45, Replace:
"vs. 1, and"
With:
--vs. t, and--

Under Column no. 12, Line no. 45, Replace:
"dependent at) (Model"
With:
--dependent $\varepsilon$(t) (Model--

Under Column no. 15, Line no. 11, Replace:
" $\langle\varepsilon\rangle_{T=15\ days}^{t_{eff}=10\ nm}$ "
With:
-- $\langle\varepsilon\rangle_{T=15\ days}^{t_{eff}=10\ nm}$ --

Under Column no. 16, Line no. 53, Replace:
"flat d calc VS."
With:
--flat $d_{calc}$ VS.--

Under Column no. 17, Line no. 9, Replace:
"where ⟨ε⟩ is"
With:
--where ⟨ε⟩$_T$ is--

Under Column no. 19, Line no. 15, Replace:
"8.0, 0=11.1"
With:
--8.0, σ=11.1--

Under Column no. 20, Line no. 59, Replace:
"1M KCl"
With:
--1M KCl--

Under Column no. 23, Line no. 53, Replace:
"the pore. (4)"
With:
--the pore, (4)--

Under Column no. 26, Line no. 11, Replace:
"5S IRNA, transfer"
With:
--5S rRNA, transfer--

Under Column no. 26, Line no. 11, Replace:
"RNA (IRNA), microRNA"
With:
--RNA (tRNA), microRNA--

Under Column no. 26, Line no. 14, Replace:
"(piRNA), IRNA-derived"
With:
--(piRNA), tRNA-derived--